United States Patent
Damask et al.

(10) Patent No.: US 12,264,366 B2
(45) Date of Patent: Apr. 1, 2025

(54) GENOME-BASED METHODS FOR REDUCING CARDIOVASCULAR RISK

(71) Applicant: Regeneron Pharmaceuticals, Inc., Tarrytown, NY (US)

(72) Inventors: Amy Damask, Tarrytown, NY (US); Charles Paulding, Tarrytown, NY (US); Aris Baras, Tarrytown, NY (US); Goncalo Abecasis, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 824 days.

(21) Appl. No.: 16/876,030

(22) Filed: May 16, 2020

(65) Prior Publication Data

US 2021/0002724 A1 Jan. 7, 2021

Related U.S. Application Data

(60) Provisional application No. 62/933,181, filed on Nov. 8, 2019, provisional application No. 62/849,670, filed on May 17, 2019.

(51) Int. Cl.
*C12Q 1/6883* (2018.01)
*A61K 39/00* (2006.01)
*C07K 16/40* (2006.01)
*G16B 20/00* (2019.01)
*G16B 40/20* (2019.01)

(52) U.S. Cl.
CPC ............ *C12Q 1/6883* (2013.01); *C07K 16/40* (2013.01); *G16B 20/00* (2019.02); *G16B 40/20* (2019.02); *A61K 2039/505* (2013.01); *C07K 2317/21* (2013.01); *C07K 2317/76* (2013.01); *C12Q 2600/118* (2013.01); *C12Q 2600/156* (2013.01)

(58) Field of Classification Search
CPC ............ C12Q 1/6883; C12Q 2600/118; C12Q 2600/156; C07K 16/40; C07K 2317/21; C07K 2317/76; G16B 20/00; G16B 40/20; A61K 2039/505; A61K 39/3955; A61P 3/06; A61P 43/00
See application file for complete search history.

(56) References Cited

U.S. PATENT DOCUMENTS

| 2018/0195122 | A1 | 7/2018 | Kornman et al. | |
| 2019/0017119 | A1* | 1/2019 | Khera | C12Q 1/6886 |

FOREIGN PATENT DOCUMENTS

| WO | 2008140793 | 11/2008 |
| WO | 2009129454 | 10/2009 |
| WO | 2013120114 | 8/2013 |
| WO | 2014031764 | 2/2014 |

OTHER PUBLICATIONS

Gaudet et al. Am J. Cardiol. 2017, 119, 40-46. (Year: 2017).*
O'Donoghue et al. Circulation, Mar. 19, 2019, 139, 1483-1492. (Year: 2019).*
ClinicalTrials.gov NCT01968967 final report published Jul. 31, 2018 (Year: 2017).*
Ridker et al. New Engl. J. Med., 376:1527-39, (Year: Mar. 17, 2017).*
Ridker et al, J Clin Lipidol., 12(4):958-965, (Year: Apr. 3, 2018).*
Samani et al., N.Engl.J. Med. 357:443-453, (Year: 2007).*
Benes et al., "The Role of Genetics in Cardiovascular Risk Reduction: Findings From a Single Lipid Clinic and Review of the Literature", Cardiovascular Revascularization Medicine, 2019, 21(2), pp. 200-204.
D'Agostino et al., "Primary and subsequent coronary risk appraisal: New results from The Framingham Study", American Heart Journal, 2000, 139, pp. 272-281.
Goldstein et al., "Simple, standardized incorporation of genetic risk into non-genetic risk prediction tools for complex traits: coronary heart disease as an example", Frontiers in Genetics, 2014, 5, pp. 1-9.
Khera et al., "Genome-wide polygenic scores for common diseases identify individuals with risk equivalent to monogenic mutations", Nature Genetics, 2018, 50, pp. 1219-1224.
Lloyd-Jones et al, "Improved polygenic prediction by Bayesian multiple regression on summary statistics", Nature Communications, 2019, 10(5086), pp. 1-11.
Nikpay et al., "A comprehensive 1000 Genomes-based genome-wide association meta-analysis of coronary artery disease", Nat Genet, 2015, 47(10), pp. 1121-1130.
Purcell et al., "Common polygenic variation contributes to risk of schizophrenia that overlaps with bipolar disorder", Nature, 2009, 460(7256), pp. 748-752.
Roberts, "Genetics—Current and Future Role in the Prevention and Management of Coronary Artery Disease", Current Atherosclerosis Reports, 2016, 18(12), pp. 1-8.
Roe et al., "Risk Categorization Using New American College of Cardiology/American Heart Association Guidelines for Cholesterol Management and Its Relation to Alirocumab Treatment Following Acute Coronary Syndromes", Circulation, 2019, 140, pp. 1578-1589.
Sabatine et al., "Clinical Benefit of Evolocumab by Severity and Extent of Coronary Artery Disease: Analysis From Fourier", Circulation, 2018, 138(8), pp. 756-766.
Vilhjalmsson et al., "Modeling Linkage Disequilibrium Increases Accuracy of Polygenic Risk Scores", Am J Human Genetics, 2015, 97, pp. 576-592.
Yang et al., "Conditional and joint multiple-SNP analysis of GWAS summary statistics identifies additional variants influencing complex traits", Nat Genet, 2013, 44(4), pp. 369-375.
International Search Report and Written Opinion dated Sep. 2, 2020 for PCT Application PCT/US2020/033315.

* cited by examiner

*Primary Examiner* — Kimberly Ballard
*Assistant Examiner* — Stacey N Macfarlane
(74) *Attorney, Agent, or Firm* — Armstrong Teasdale LLP

(57) ABSTRACT

The present disclosure provides methods of reducing cardiovascular risk by administration of a PCSK9 inhibitor to patients having a genetic profile associated with response to PCSK9 inhibitor therapy.

7 Claims, 75 Drawing Sheets

Specification includes a Sequence Listing.

| Characteristic | ODSSEY OUTCOMES (N=18942) | ODYSSEY Genetic Subgroup (N=11953) | Lower Genetic Risk Group (N=10756) |
|---|---|---|---|
| Age — y[2] | 58.6 ± 9.3 | 58.7 ± 9.3 | 58.9 ± 9.3 |
| Female sex — no. (%) | 4762 (25.2) | 3039 (25.4) | 2695 (25.1) |
| Self-identified Race — no. (%) | | | |
| White | 15024 (79.4) | 10210 (85.4) | 9178 (85.3) |
| Asian | 2498 (13.2) | 834 (7.0) | 751 (7.0) |
| Black | 473 (2.5) | 323 (2.7) | 304 (2.8) |
| Other | 929 (4.9) | 586 (4.9) | 523 (4.9) |
| *Lipids and other biomarkers — median (IQR)* | | | |
| Total Cholesterol (mg/dL) | 159.8 (142.0 - 182.0) | 159.8 (142.9 - 182.0) | 159.0 (142.5 - 181.6) |
| LDL-C (mg/dL) | 86.5 (73.0 - 104.0) | 86.5 (73.4 - 103.5) | 86.1 (73.0 - 103.0) |
| HDL-C (mg/dL) | 42.5 (36.3 - 50.2) | 43.0 (36.7 - 50.6) | 43.0 (36.7 - 50.6) |
| non-HDL-C (mg/dL) | 115.0 (99.2 - 137.0) | 114.7 (99.2 - 135.9) | 114.3 (99.0 - 135.5) |
| Triglycerides (mg/dL) | 129.2 (94.0 - 182.0) | 127.4 (92.9 - 180.5) | 127.0 (92.9 - 181.4) |
| Lipoprotein-(a) (mg/dL) | 21.1 (6.7 - 59.9) | 21.6 (6.7 - 61.5) | 19.9 (6.3 - 57.5) |
| Apo-A1 (mg/dL) | 131.0 (118.0 - 147.0) | 132.0 (118.0 - 149.0) | 132.0 (118.0 - 149.0) |
| Apo-B (mg/dL) | 79.0 (69.0 - 93.0) | 79.0 (69.0 - 92.0) | 79.0 (69.0 - 92.0) |
| hs-CRP (mg/L) | 0.2 (0.1 - 0.4) | 0.2 (0.1 - 0.4) | 0.2 (0.1 - 0.4) |
| HbA1C (mmol/mol) | 5.8 (5.5 - 6.3) | 5.8 (5.5 - 6.3) | 5.8 (5.5 - 6.3) |

[1] Lower genetic risk is defined as a polygenic risk score (PRS) ≤ 90th percentile. High genetic risk is defined as a PRS > 90th percentile.
[2] Plus-minus values are means ± SD.

Figure 1

| Characteristic | High Genetic Risk Group (N=1197) | Lower v. High Genetic Risk P-value |
|---|---|---|
| Age — yr[2] | 57.1 ± 9.1 | 1.5 x 10⁻¹⁰ |
| Female sex — no. (%) | 344 (28.7) | 0.006 |
| *Self-identified Race — no. (%)* | | |
| White | 1032 (86.2) | |
| Asian | 83 (6.9) | |
| Black | 19 (1.6) | 0.087 |
| Other | 63 (5.3) | |
| *Lipids and other biomarkers — median (IQR)* | | |
| Total Cholesterol (mg/dL) | 164.0 (144.8 - 188.0) | 0.005 |
| LDL-C (mg/dL) | 88.4 (74.9 - 108.1) | 6.2 x 10⁻⁴⁴ |
| HDL-C (mg/dL) | 42.9 (37.0 - 51.0) | 0.558 |
| non-HDL-C (mg/dL) | 118.1 (101.2 - 140.0) | 0.004 |
| Triglycerides (mg/dL) | 128.3 (94.7 - 175.0) | 0.28 |
| Lipoprotein-(a) (mg/dL) | 49.4 (12.5 - 94.2) | 3.5 x 10⁻⁶⁶ |
| Apo-A1 (mg/dL) | 132.0 (118.0 - 149.0) | 0.498 |
| Apo-B (mg/dL) | 81.0 (70.0 - 95.0) | 0.001 |
| hs-CRP (mg/L) | 0.2 (0.1 - 0.4) | 0.988 |
| HbA1C (mmol/mol) | 5.8 (5.5 - 6.2) | 0.097 |

[1] Lower genetic risk is defined as a polygenic risk score (PRS) ≤ 90th percentile. High genetic risk is defined as a PRS > 90th percentile.
[2] Plus-minus values are means ± SD.

Figure 1 (cont.)

| Characteristic | ODYSSEY OUTCOMES (N=18942) | ODYSSEY Genetic Subgroup (N=11953) | Lower Genetic Risk Group (N=10756) |
|---|---|---|---|
| Medical history before index acute coronary syndrome — no. (%) | | | |
| Hypertension | 12249 (64.7) | 7805 (65.3) | 7020 (65.3) |
| Diabetes mellitus | 5444 (28.8) | 3279 (27.4) | 2959 (27.5) |
| Current tobacco smoker | 4560 (24.1) | 2915 (24.4) | 2632 (24.5) |
| Family history of premature coronary heart disease | 6773 (35.8) | 4781 (40.0) | 4243 (39.4) |
| Myocardial infarction | 3633 (19.2) | 2371 (19.8) | 2095 (19.5) |
| Percutaneous coronary intervention | 3241 (17.1) | 2174 (18.2) | 1931 (18.0) |
| Coronary-artery bypass grafting | 1047 (5.5) | 720 (6.0) | 615 (5.7) |
| Stroke | 611 (3.2) | 358 (3.0) | 328 (3.0) |
| Peripheral artery disease | 759 (4.0) | 534 (4.5) | 484 (4.5) |
| Congestive heart failure | 2815 (14.9) | 1758 (14.7) | 1550 (14.4) |

[1] Lower genetic risk is defined as a polygenic risk score (PRS) ≤ 90th percentile. High genetic risk is defined as a PRS > 90th percentile.
[2] Plus-minus values are means ± SD.

Figure 1 (cont.)

| Characteristic | High Genetic Risk Group (N=1197) | Lower v. High Genetic Risk p-value |
|---|---|---|
| *Medical history before index acute coronary syndrome — no. (%)* | | |
| Hypertension | 785 (65.6) | 0.853 |
| Diabetes mellitus | 320 (26.7) | 0.591 |
| Current tobacco smoker | 283 (23.6) | 0.55 |
| Family history of premature coronary heart disease | 538 (44.9) | $2.6 \times 10^{-04}$ |
| Myocardial infarction | 276 (23.1) | 0.004 |
| Percutaneous coronary intervention | 243 (20.3) | 0.05 |
| Coronary-artery bypass grafting | 105 (8.8) | $3.3 \times 10^{-06}$ |
| Stroke | 30 (2.5) | 0.339 |
| Peripheral artery disease | 50 (4.2) | 0.661 |
| Congestive heart failure | 208 (17.4) | 0.007 |

Figure 1 (cont.)

1Lower genetic risk is defined as a polygenic risk score (PRS) ≤ 90th percentile. High genetic risk is defined as a PRS > 90th percentile.
2Plus-minus values are means ± SD.

| End point | Alirocumab (N=5383) | Placebo (N=5373) | Hazard Ratio (95% CI) | P-value |
|---|---|---|---|---|
| Major adverse cardiovascular event (MACE): Composite of death from coronary heart disease, nonfatal myocardial infarction, fatal or non-fatal ischemic stroke, or unstable angina requiring hospitalization | 535 (9.9) | 612 (11.4) | 0.87 (0.78 - 0.98) | 0.022 |
| Secondary Endpoints[2] | | | | |
| Any cardiovascular event[3] | 771 (14.3) | 855 (15.9) | 0.90 (0.81 - 0.99) | 0.030 |
| Any coronary heart disease event[4] | 712 (13.2) | 783 (14.6) | 0.91 (0.82 - 1.00) | 0.055 |
| Composite of death from any cause, nonfatal myocardial infarction, or nonfatal ischemic stroke | 573 (10.6) | 651 (12.1) | 0.88 (0.79 - 0.98) | 0.026 |
| Major coronary heart disease event[5] | 472 (8.8) | 531 (9.9) | 0.89 (0.79 - 1.01) | 0.065 |

Lower Genetic Risk Group

Figure 5

| End point | High Genetic Risk Group | | | | Treatment-by-Genetic Risk Interaction p-value |
|---|---|---|---|---|---|
| | Alirocumab (N=584) | Placebo (N=613) | Hazard Ratio (95% CI) | p-value | |
| Major adverse cardiovascular event (MACE): Composite of death from coronary heart disease, nonfatal myocardial infarction, fatal or non-fatal ischemic stroke, or unstable angina requiring hospitalization | 64 (11.0) | 104 (17.0) | 0.63 (0.46 - 0.86) | 0.004 | 0.04 |
| Secondary Endpoints[2] | | | | | |
| Any cardiovascular event[3] | 92 (15.8) | 133 (21.7) | 0.68 (0.52 - 0.89) | 0.005 | 0.07 |
| Any coronary heart disease event[4] | 88 (15.1) | 125 (20.4) | 0.71 (0.54 - 0.93) | 0.014 | 0.09 |
| Composite of death from any cause, nonfatal myocardial infarction, or nonfatal ischemic stroke | 68 (11.6) | 106 (17.3) | 0.64 (0.47 - 0.87) | 0.005 | 0.05 |
| Major coronary heart disease event[5] | 59 (10.1) | 89 (14.5) | 0.69 (0.49 - 0.96) | 0.029 | 0.12 |

Figure 5 (cont.)

¹Lower genetic risk is defined as a polygenic risk score (PRS) ≤ 90th percentile. High genetic risk is defined as a PRS > 90th percentile. The estimated hazard ratios and p-values were calculated from a Cox proportional hazards model, which was adjusted for ancestry, baseline LDL-C, Lp(a), age, sex, family history of premature coronary heart disease, and the following medical characteristics prior to index ACS: myocardial infarction; percutaneous coronary intervention; coronary artery bypass grafting; and congestive heart failure.
²The p-values and widths of the confidence intervals for the secondary endpoints were not adjusted for multiple comparisons and should not be used to infer definitive treatment effects.
³This end point includes any death from cardiovascular causes, nonfatal myocardial infarction, unstable angina requiring hospitalization, an ischemia-driven coronary revascularization procedure, or nonfatal ischemic stroke (definitions can be found in the Supplementary Appendix of 10.1056/NEJMoa1801174).
⁴Includes death from coronary heart disease, nonfatal myocardial infarction, unstable angina requiring hospitalization, and an ischemia-driven coronary revascularization procedure.
⁵Includes death from coronary heart disease and nonfatal myocardial infarction.

Figure 5 (cont.)

| Characteristic | ODYSSEY OUTCOMES (N=18042) | ODYSSEY Genetic Subgroup (N=11953) | Lower Genetic Risk Group (N=10738) |
|---|---|---|---|
| Region — no. (%) | | | |
| Central and Eastern Europe | 5157 (28.7) | 3166 (26.5) | 2790 (25.9) |
| Western Europe | 4175 (23.1) | 3225 (27.0) | 2895 (26.9) |
| Canada or United States | 2871 (15.9) | 2158 (18.1) | 1957 (18.5) |
| Latin America | 2586 (13.7) | 1592 (13.3) | 1469 (13.5) |
| Asia | 2293 (12.1) | 683 (5.8) | 620 (5.9) |
| Rest of World | 1360 (8.2) | 1129 (9.3) | 1005 (9.5) |
| Genetically-determined Ancestry — no. (%) | | | |
| African | | 880 (4.9) | 531 (4.9) |
| Ad Mixed American | | 1034 (8.7) | 930 (8.8) |
| East Asian | | 987 (8.2) | 889 (8.2) |
| South Asian | | 682 (5.6) | 585 (5.5) |
| European | | 9280 (77.7) | 8361 (77.7) |

*Lower genetic risk is defined as a polygenic risk score (PRS) ≤ 90th percentile. High genetic risk is defined as a PRS > 90th percentile.
Plus-minus values are means ±SD
†Body-mass index is equal to weight (kilograms) divided by the square of the height (meters).

Figure 8

| Characteristic | High Genetic Risk Group (N=1197) | Lower v. High Genetic Risk P-value |
|---|---|---|
| Region — no. (%) | | |
| Central and Eastern Europe | 370 (31.4) | 5.1 × 10⁻⁴ |
| Western Europe | 320 (27.0) | |
| Canada or United States | 181 (15.1) | |
| Latin America | 143 (11.9) | |
| Asia | 63 (5.3) | |
| Rest of World | 104 (8.7) | |
| Genetically-determined Ancestry — no. (%) | | |
| African | 59 (4.9) | 1.000 |
| All Mixed Americans | 104 (8.7) | |
| East Asian | 38 (3.2) | |
| South Asian | 67 (5.6) | |
| European | 929 (77.6) | |

*Lower genetic risk is defined as a polygenic risk score (PRS) ≤ 90th percentile. High genetic risk is defined as a PRS > 90th percentile. Plus-minus values are means ±SD
†Body-mass index is equal to weight (kilograms) divided by the square of the height (meters).

Figure 8 (cont.)

| Characteristic | ODYSSEY OUTCOMES (N=18942) | ODYSSEY Genetic Subgroup (N=11953) | Lower Genetic Risk Group (N=10756) |
|---|---|---|---|
| Index acute coronary syndrome — no. (%) | | | |
| Non-ST-segment elevation myocardial infarction | 9175 (48.5) | 5824 (60.4) | 5499 (60.5) |
| ST-segment elevation myocardial infarction | 6536 (34.5) | 4258 (35.4) | 3798 (35.3) |
| Unstable angina | 3182 (16.8) | 1670 (14.0) | 1507 (14.0) |
| Missing data | 31 (0.2) | 21 (0.2) | 21 (0.2) |
| Percutaneous coronary intervention or coronary-artery bypass grafting for index acute coronary syndrome — no. (%) | 13675 (72.3) | 8771 (73.4) | 7883 (73.1) |
| Mean time from index acute coronary syndrome to randomization — mo | 3.4 ± 2.7 | 3.3 ± 2.6 | 3.4 ± 2.6 |
| Body-mass index† | 28.5 ± 4.9 | 28.8 ± 4.9 | 28.8 ± 4.9 |
| Lipids — mean (± SD) | | | |
| Total Cholesterol (mg/dL) | 166.5 ± 37.0 | 166.3 ± 36.0 | 166.0 ± 36.0 |
| LDL-C (mg/dL) | 92.4 ± 31.0 | 92.1 ± 29.7 | 91.8 ± 29.7 |
| HDL-C (mg/dL) | 44.3 ± 11.4 | 44.6 ± 11.4 | 44.6 ± 11.3 |
| non-HDL-C (mg/dL) | 122.3 ± 33.3 | 121.6 ± 33.1 | 121.5 ± 33.1 |
| Triglycerides (mg/dL) | 149.6 ± 84.9 | 148.1 ± 85.6 | 146.2 ± 84.2 |
| Lipoprotein-(a) (mg/dL) | 39.0 ± 43.3 | 39.7 ± 43.9 | 37.4 ± 41.9 |
| Apo-A1 (mg/dL) | 133.9 ± 23.7 | 134.8 ± 24.0 | 134.7 ± 23.8 |
| Apo-B (mg/dL) | 83.1 ± 21.4 | 82.7 ± 20.9 | 82.6 ± 20.9 |

*Lower genetic risk is defined as a polygenic risk score (PRS) ≤ 90th percentile. High genetic risk is defined as a PRS > 90th percentile. Plus-minus values are means ±SD
†Body-mass index is equal to weight (kilograms) divided by the square of the height (meters).

Figure 8 (cont.)

| Characteristic | High Genetic Risk Group (N=1197) | Lower v. High Genetic Risk P-value |
|---|---|---|
| Index acute coronary syndrome — no. (%) | | |
| Non-ST-segment elevation myocardial infarction | 594 (49.6) | 0.480 |
| ST-segment elevation myocardial infarction | 435 (36.3) | |
| Unstable angina | 168 (14.0) | |
| Missing data | 0 (0.0) | |
| Percutaneous coronary interventions or coronary-artery bypass grafting for index acute coronary syndrome — no. (%) | 908 (75.9) | 0.044 |
| Mean time from index acute coronary syndrome to randomization — mo | 3.2 ± 2.5 | 0.087 |
| Body-mass index† | 28.7 ± 4.9 | 0.458 |
| Lipids — mean (± SD) | | |
| Total Cholesterol (mg/dL) | 169.1 ± 36.1 | 0.865 |
| LDL-C (mg/dL) | 94.4 ± 29.0 | 6.2 × 10⁻⁰⁶ |
| HDL-C (mg/dL) | 46.0 ± 12.1 | 0.595 |
| non-HDL-C (mg/dL) | 124.2 ± 33.8 | 0.981 |
| Triglycerides (mg/dL) | 147.3 ± 79.9 | 0.290 |
| Lipoprotein-(a) (mg/dL) | 60.4 ± 56.0 | 3.5 × 10⁻⁵⁶ |
| Apo-A1 (mg/dL) | 135.4 ± 25.2 | 0.498 |
| Apo-B (mg/dL) | 84.3 ± 21.0 | 0.001 |

*Lower genetic risk is defined as a polygenic risk score (PRS) ≤ 90th percentile. High genetic risk is defined as a PRS > 90th percentile.
Plus-minus values are means ±SD
†Body-mass index is equal to weight (kilograms) divided by the square of the height (meters).

Figure 8 (cont.)

|  | Overall | | High Risk Genetic Group | |
| --- | --- | --- | --- | --- |
| Ancestry | Alirocumab (N=5,907) | Placebo (N=5,986) | Alirocumab (N=584) | Placebo (N=613) |
| All | 10.0 (590/5907) | 12.0 (716/5986) | 11.0 (64/584) | 17.0 (104/613) |
| Ad Mixed American | 11.0 (56/510) | 11.3 (59/524) | 13.3 (6/45) | 16.0 (10/59) |
| African | 13.5 (39/288) | 10.5 (39/302) | 15.6 (5/32) | 29.6 (8/27) |
| East Asian | 9.1 (17/187) | 10.0 (19/190) | 0.0 (0/19) | 15.8 (3/19) |
| European | 9.6 (457/4640) | 11.7 (542/4644) | 11.0 (50/455) | 16.5 (78/474) |
| South Asian | 8.9 (30/336) | 11.3 (37/326) | 9.1 (3/33) | 14.7 (5/34) |

*Major adverse cardiovascular events (MACE) is composite end point of death from coronary heart disease, nonfatal myocardial infarction, fatal or non-fatal ischemic stroke, or unstable angina requiring hospitalization. Lower genetic risk is defined as a polygenic risk score (PRS) ≤90th percentile. High genetic risk is defined as a PRS > 90th percentile. Descriptive statistics shown are Percent (N with event/Total N) by ancestral group.

Figure 12

| Lipid | Alirocumab | | |
|---|---|---|---|
| | Overall (N=5007) | Lower Risk Genetic Group (N=5383) | High Risk Genetic Group (N=584) |
| Total Cholesterol (mg/dL) | -57.1 (-76.4 : -39.0) | -57.0 (-76.0 : -39.4) | -58.7 (-79.0 : -37.5) |
| LDL-C (mg/dL) | -55.2 (-71.0 : -40.2) | -55.0 (-70.7 : -40.2) | -56.0 (-72.5 : -39.0) |
| HDL-C (mg/dL) | 3.1 (-0.8 : 7.7) | 3.1 (-0.8 : 7.7) | 3.1 (-0.7 : 7.7) |
| non-HDL-C (mg/dL) | -61.0 (-79.0 : -43.6) | -60.6 (-79.0 : -43.6) | -62.9 (-82.0 : -43.6) |
| Triglycerides (mg/dL) | -16.8 (-47.1 : 10.0) | -16.8 (-47.8 : 10.0) | -16.8 (-45.4 : 9.0) |
| Lipoprotein-(a) (mg/dL) | -5.3 (-14.0 : 0.0) | -5.1 (-13.3 : 0.0) | -8.2 (-21.1 : -0.9) |
| Apo-A1 (mg/dL) | 7.0 (-4.0 : 18.0) | 7.0 (-4.0 : 18.0) | 6.0 (-6.0 : 18.0) |
| Apo-B (mg/dL) | -45.0 (-57.5 : -31.0) | -45.0 (-57.5 : -31.0) | -46.0 (-57.0 : -30.0) |

*Lower genetic risk is defined as a polygenic risk score (PRS) ≤ 90th percentile. High genetic risk is defined as a PRS > 90th percentile. Values shown are median (IQR).

Figure 25

| Lipid | Placebo Overall (N=5986) | Placebo Lower Risk Genetic Group (N=5373) | Placebo High Risk Genetic Group (N=613) |
|---|---|---|---|
| Total Cholesterol (mg/dL) | 2.7 (-12.4 : 18.0) | 2.7 (-12.0 : 18.0) | 2.3 (-13.3 : 17.9) |
| LDL-C (mg/dL) | 0.8 (-11.6 : 13.9) | 0.8 (-11.2 : 13.5) | 0.4 (-12.1 : 14.1) |
| HDL-C (mg/dL) | 1.0 (-3.0 : 5.0) | 1.0 (-3.0 : 5.0) | 1.2 (-2.7 : 5.0) |
| non-HDL-C (mg/dL) | 1.0 (-13.0 : 15.4) | 1.0 (-13.0 : 15.1) | 0.4 (-14.8 : 16.0) |
| Triglycerides (mg/dL) | 0.9 (-26.3 : 30.0) | 0.0 (-28.3 : 29.9) | -0.8 (-20.5 : 35.3) |
| Lipoprotein-(a) (mg/dL) | 0.0 (-4.8 : 2.3) | 0.0 (-4.7 : 2.4) | 0.0 (-6.4 : 3.6) |
| Apo-A1 (mg/dL) | 2.0 (-9.0 : 12.1) | 2.0 (-9.0 : 12.0) | 2.0 (-8.0 : 14.0) |
| Apo-B (mg/dL) | 0.0 (-8.0 : 10.0) | 0.0 (-8.0 : 9.0) | 1.0 (-9.0 : 10.8) |

*Lower genetic risk is defined as a polygenic risk score (PRS) ≤ 90th percentile. High genetic risk is defined as a PRS > 90th percentile. Values shown are median (IQR).

Figure 25 (cont.)

| Decile | Alirocumab HR Genetic Risk Median (Q1 - Q3) | Placebo HR Genetic Risk Median (Q1 - Q3) | Alirocumab % with end point Median (Q1 - Q3) | Placebo % with end point Median (Q1 - Q3) | Treatment Difference HR Alirocumab v. Placebo Median (Q1 - Q3) |
|---|---|---|---|---|---|
| 1 | 0.99 (0.95 - 1.05) | 0.98 (0.94 - 1.03) | 9.9 (9.4 - 10.4) | 11.8 (11.4 - 12.4) | 0.80 (0.74 - 0.90) |
| 2 | 0.99 (0.95 - 1.03) | 0.93 (0.85 - 1.00) | 9.6 (9.0 - 10.6) | 11.3 (10.2 - 12.2) | 0.82 (0.81 - 0.91) |
| 3 | 0.99 (0.96 - 1.07) | 0.92 (0.83 - 1.00) | 9.9 (8.8 - 10.6) | 11.1 (10.2 - 12.7) | 0.86 (0.76 - 0.99) |
| 4 | 0.91 (0.85 - 1.00) | 0.92 (0.87 - 1.01) | 9.3 (8.7 - 10.3) | 11.3 (10.7 - 12.2) | 0.82 (0.76 - 0.91) |
| 5 | 0.97 (0.88 - 1.11) | 0.94 (0.88 - 1.08) | 9.8 (9.0 - 10.9) | 11.4 (10.8 - 12.0) | 0.83 (0.74 - 0.93) |
| 6 | 1.00 (0.95 - 1.14) | 0.97 (0.90 - 1.06) | 10.4 (9.6 - 11.2) | 11.6 (11.0 - 12.5) | 0.89 (0.78 - 0.96) |
| 7 | 1.01 (0.91 - 1.09) | 1.02 (0.91 - 1.09) | 10.4 (9.5 - 10.8) | 12.1 (11.1 - 13.1) | 0.81 (0.71 - 0.95) |
| 8 | 1.03 (0.95 - 1.12) | 1.00 (0.95 - 1.09) | 10.5 (9.6 - 11.2) | 11.9 (11.4 - 12.9) | 0.82 (0.74 - 0.96) |
| 9 | 1.07 (0.96 - 1.14) | 1.03 (0.96 - 1.09) | 10.6 (9.9 - 11.1) | 11.9 (11.6 - 12.9) | 0.87 (0.73 - 0.99) |
| 10 | 1.09 (1.05 - 1.13) | 1.24 (1.18 - 1.29) | 10.6 (10.1 - 11.0) | 14.4 (13.2 - 14.9) | 0.70 (0.65 - 0.76) |

* Across all columns, the median, first quartile (Q1), and third quartile (Q3) estimates from all 36 PRS generation algorithms are shown. In the alirocumab and placebo HR genetic risk columns, the hazard ratio (HR) reflects the comparison of that genetic risk decile to all other deciles in that treatment arm. In the alirocumab and placebo % with endpoint columns, the percent of patients with an event in that decile is shown. In the HR treatment difference column, the estimate reflects the comparison of alirocumab and placebo event rates in that decile.

Figure 29

GENOME-BASED METHODS FOR REDUCING CARDIOVASCULAR RISK

FIELD

The present disclosure relates to the field of therapeutic treatments of diseases and disorders that are associated with elevated levels of lipids and lipoproteins. More specifically, the disclosure relates to the methods of increasing the efficacy of Proprotein Convertase Subtilisin-Kexin Type 9 (PCSK9) inhibitors therapy in high cardiovascular risk patients through identification of patients that are likely to respond to PCSK9 inhibitors.

BACKGROUND

Despite modern therapy including prompt coronary revascularization, dual antiplatelet therapy, and intensive statin treatment, major adverse cardiovascular events (MACE) occur with high frequency following in patients who previously had a MACE. Registry data indicates cardiovascular mortality as high as 13% at 5 years, with an overwhelming majority occurring after initial discharge from the hospital. Patients with recent MACE are at very high risk for suffering recurrent MACE in the near term. In approximately 10% of patients who previously had a MACE, cardiovascular death, recurrent myocardial infarction, or stroke occurs within 1 year.

PCSK9 is a serine protease involved in regulating the levels of the low-density lipoprotein receptor (LDLR) protein. In vitro experiments have shown that adding PCSK9 to HepG2 cells lowers the levels of cell surface LDLR. Experiments with mice have shown that increasing PCSK9 protein levels decreases levels of LDLR protein in the liver, while PCSK9 knockout mice have increased levels of LDLR in the liver. Additionally, various human PCSK9 mutations that result in either increased or decreased levels of plasma LDL have been identified. PCSK9 has been shown to directly interact with the LDLR protein, be endocytosed along with the LDLR, and co-immunofluorescence with the LDLR throughout the endosomal pathway. Degradation of the LDLR by PCSK9 has not been observed and the mechanism through which it lowers extracellular LDLR protein levels is uncertain.

The establishment of a link between PCSK9 and cholesterol metabolism was rapidly followed by the discovery that selected mutations in the PCSK9 gene caused autosomal dominant hypercholesterolemia, suggesting that the mutations confer a gain-of-function by increasing the normal activity of PCSK9. Conversely, loss-of-function PCSK9 mutations and inhibition of PCSK9 function have been shown to significantly reduce LDL levels and the frequency of MACE.

PCSK9 inhibition decreases the risk for MACE in both in primary and secondary intervention settings, but not all patients respond equally well to PCSK9 inhibition treatment. Cardiovascular disease etiology is complex and may be influenced by genetics, environment, and a variety of additional risk factors including dyslipidemia, age, gender, hypertension, diabetes, obesity, and smoking. Genome-wide association studies (GWAS) have identified genetic variants associated broadly with coronary disease, but there is a need to harness genomic data to identify patients likely to benefit specifically from PCSK9 inhibition therapy, with the aim of preventing or reducing the likelihood of MACE.

SUMMARY

The present disclosure provides methods of treating a patient at risk for a MACE, comprising: determining the patient's coronary artery disease polygenic risk score (CAD-PRS), wherein the CAD-PRS comprises a weighted sum of a plurality of genetic variants associated with coronary artery disease; identifying a patient as at increased risk of a MACE if the patient has a CAD-PRS greater than a threshold CAD-PRS determined from a reference population; and if the patient is identified as at increased risk of a MACE, administering a PCSK9 inhibitor to the patient.

The present disclosure also provides methods for lowering the level of serum LDL in a patient at increased risk of a MACE, comprising: determining the patient's CAD-PRS, wherein the CAD-PRS comprises a weighted sum of a plurality of genetic variants associated with coronary artery disease; identifying a patient as at increased risk of a MACE if the patient has a CAD-PRS greater than a threshold CAD-PRS determined from a reference population; and if the patient is identified as at increased risk of a MACE, administering a PCSK9 inhibitor to the subject in an amount effective to lower the patient's level of serum LDL.

The present disclosure also provides methods for lowering the level of serum LDL in a patient at increased risk of a MACE, comprising: determining the patient's CAD-PRS, wherein the CAD-PRS comprises a weighted sum of a plurality of genetic variants associated with coronary artery disease; identifying a patient as at increased risk of a MACE if the patient has a CAD-PRS greater than a threshold CAD-PRS determined from a reference population; and when the patient is identified as at increased risk of a MACE, administering a PCSK9 inhibitor to the subject in an amount effective to lower the patient's level of serum LDL.

The present disclosure also provides methods of screening a candidate subject for inclusion in a clinical trial for the treatment of a cardiovascular condition, the method comprising: determining the candidate subject's CAD-PRS, wherein the CAD-PRS comprises a weighted sum of a plurality of genetic variants associated with coronary artery disease; and when the candidate subject has a CAD-PRS greater than a threshold CAD-PRS determined from a reference population, then including the candidate subject in the clinical trial; or when the candidate subject has a CAD-PRS lower than a threshold CAD-PRS determined from a reference population, then excluding the candidate subject from the clinical trial.

These and other objects and features of the present disclosure will be better understood and appreciated from the following detailed description of one embodiment thereof, selected for purposes of illustration and shown in the accompanying drawings.

BRIEF DESCRIPTION OF THE DRAWINGS

FIG. 1 shows a table listing demographic and baseline characteristics of patients in the pharmacogenomic analysis, with a comparison of high and lower risk genetic groups and generalizability to ODYSSEY OUTCOMES.

FIG. 5 shows a table listing primary and secondary endpoints across lower and high risk genetic risk groups.

FIG. 8 shows a table listing additional demographic and baseline characteristics of the patients in the pharmacogenomic analysis.

FIG. 12 shows a table listing incidence of MACE by ancestral group.

FIG. 25 shows a table listing median change in Lipids and associated proteins from baseline at month 4.

FIG. 29 shows a table listing risk by genetic decile, summarized across PRS generation algorithms.

DESCRIPTION OF EMBODIMENTS

Figure 2:
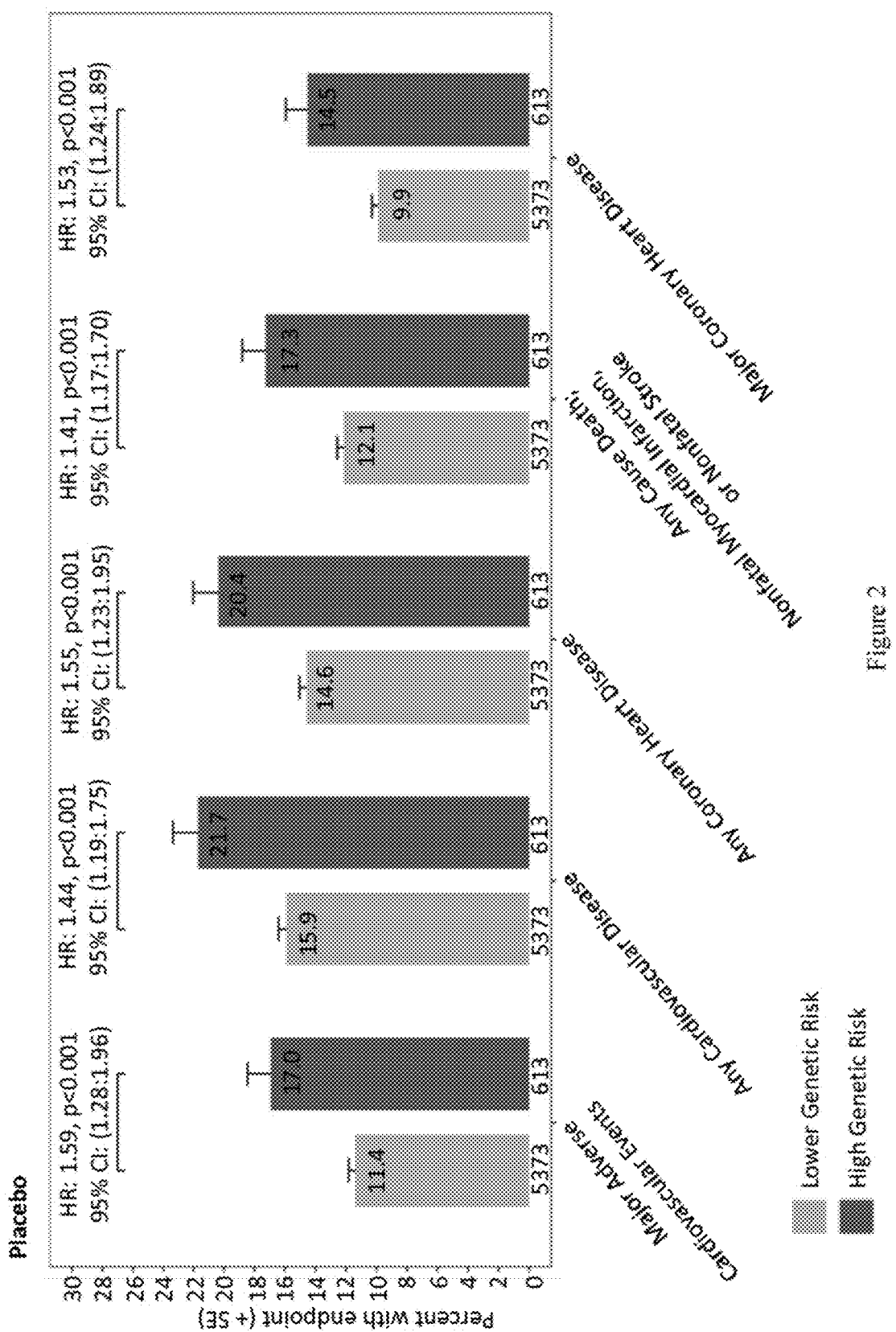
FIG. 2 shows incidence of MACE and secondary end points in the placebo arm in lower genetic risk group (polygenic risk score (PRS) ≤90th percentile) and high genetic risk group (PRS >90th percentile). Shown is the overall incidence of MACE (a composite of death from coronary heart disease, nonfatal myocardial infarction, fatal or nonfatal ischemic stroke, or unstable angina requiring hospitalization) and key secondary endpoints in patients of all ancestries, stratified by genetic risk. The numbers at the bottom of each panel are the number of patients in each group and the number inside each bar is the percent with MACE in each group. The hazard ratios and p-values were calculated from a cox proportional hazards model, which was adjusted for ancestry, baseline LDL-C, Lp(a), age, sex, family history of premature coronary heart disease, and the following medical characteristics prior to index ACS: myocardial infarction; percutaneous coronary intervention; coronary artery bypass grafting; and congestive heart failure.

Genetic factors can play an important role in risk for developing disease, and potentially influence how individuals respond to drug treatment. PRS combine information from a large number of genetic variants, derived from disease association studies, to create a single composite quantitative measure for each individual which reflects his or her genetically-derived disease risk. An individual with a larger number of risk alleles for a given disease will have a higher PRS than an individual with fewer alleles. Risk can be evaluated at several thresholds, such as percentiles or standard deviation units of the population distribution. The present disclosure relates generally to the unexpected finding that stratification of subjects by CAD-PRS is useful in identification of subjects likely to benefit from treatment with a PCSK9 inhibitor, independent of traditional clinical criteria such as LDL cholesterol levels.

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the terms "subject" and "patient" are used interchangeably. A subject may include any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human.

As used herein, "major adverse cardiovascular events" or "MACE" refers to one or more of: death from coronary heart disease (CHD death), coronary artery disease (CAD), non-fatal myocardial infarction (MI), unstable angina requiring hospitalization, fatal or non-fatal ischemic stroke, ischemia-driven coronary revascularization, arrhythmias, cardiovascular death, heart valve disease, cardiomyopathy, or congestive heart failure.

As used herein, "MACE risk patient" or "risk patient" refers to a patient with hypercholesterolemia and/or elevated levels of at least one atherogenic lipoprotein. In some embodiments, a MACE risk patient has hypercholesterolemia and/or elevated levels of at least one atherogenic lipoprotein. In some embodiments, a MACE risk patient is a patient that previously had a MACE.

The term "ischemia-driven coronary revascularization" refers to percutaneous coronary intervention (PCI) or coronary artery bypass graft (CABG). For the clinical studies disclosed herein, coronary revascularization procedures performed solely for restenosis at prior PCI site were excluded from this definition. In some embodiments, ischemia-driven coronary revascularization must be driven by one of the following: a) acute ischemia, b) new or progressive symptoms (angina or equivalent), or 3) new or progressive functional testing abnormalities (e.g., stress testing or imaging).

As used herein, "coronary heart disease death," "CHD death," and "death due to coronary heart disease" are used interchangeably to refer to the subset of cardiovascular deaths for which there is a clear relationship to underlying coronary heart disease, including death secondary to acute myocardial infarction (MI), sudden death, heart failure, complication of a coronary revascularization procedure performed for symptoms, coronary disease progression, or new myocardial ischemia where the cause of death is clearly related to the procedure, unobserved and unexpected death, and other death that cannot definitely be attributed to a nonvascular cause.

As used herein, the terms "cardiovascular event" or "CV event" refer to any non-fatal coronary heart disease event, any cardiovascular death, and any non-fatal ischemic stroke. Exemplary CV events include, but are not limited to, myocardial infarction, stroke, unstable angina requiring hospitalization, heart failure requiring hospitalization, and an ischemia-driven coronary revascularization procedure.

As used herein, the terms "cardiovascular death", "CV death", and "cardiovascular mortality" are used interchangeably to refer to death resulting from an acute myocardial infarction, sudden cardiac death, death due to heart failure, death due to stroke, and death due to other cardiovascular causes. In some embodiments, the CV death is CHD death. In other embodiments the CV death is selected from the group consisting of heart failure or cardiogenic shock, stroke, ischemic cardiovascular causes, or a cardiovascular cause other than ischemia.

As used herein, the term "non-fatal cardiovascular event" refers to any CV event that does not result in death. In some embodiments, non-fatal CV events may occur consecutively in time wherein an initial (e.g., first) CV event is followed by a subsequent (e.g., second, third or fourth) event.

As used herein, "non-cardiovascular death" and "non-CV death" are used interchangeably to refer to any death that is not thought to be a cardiovascular death. Examples of non-cardiovascular death include but are not limited to pulmonary infection, pulmonary malignancy, gastrointestinal/hepatobiliary/pancreatic infection, gastrointestinal/hepatobiliary/pancreatic malignancy, hemorrhage, neurological process that is not a stroke/hemorrhage, suicide, a non-cardiovascular procedure or surgery, accident or trauma, renal infection, renal malignancy other non-cardiovascular infection, and other non-cardiovascular malignancy.

As used herein, "non-fatal myocardial infarction" is defined and sub-classified in accordance with ACC/AHA/ESC Universal Definition of Myocardial Infarction (see, Thygesen et al., J. Amer. Coll. Cardiol., 2012, 60, 1581-98).

As used herein, "coronary artery bypass grafting (CABG)" refers to a procedure in which autologous arteries or veins are used as grafts to bypass coronary arteries that are partially or completely obstructed by atherosclerotic plaques (see, Alexander & Smith, New Eng. J. Med, 2016, 374, 1954-64).

As used herein, the terms "unstable angina requiring hospitalization" and "hospitalization for unstable angina" are used interchangeably to refer to: admission to hospital or emergency department with symptoms of myocardial ischemia with an accelerating tempo in the prior 48 hours and/or rest chest discomfort ≥20 min, requiring in addition both of the following: a) new or presumed new ischemic ECG changes, defined by ST depression >0.5 mm in 2 contiguous leads; T-wave inversion >1 mm in 2 contiguous leads with prominent R-wave or R/S>1; ST elevation in >2 contiguous leads >0.2 mV in V2 or V3 in men, >0.15 mV in V2 or V3 in women, or >0.1 mV in other leads; or LBBB; and b) definite contemporary evidence of coronary obstruction by need for coronary revascularization procedure or at least one epicardial stenosis ≥70%. For the clinical trials disclosed herein, coronary revascularization procedures or stenoses due only to restenosis at prior PCI site were excluded.

As used herein, "ischemic stroke" refers to: 1) an acute episode of focal cerebral, spinal, or retinal dysfunction caused by infarction, defined by at least one of the following: a) pathological, imaging, or other objective evidence of acute, focal cerebral, spinal, or retinal ischemic injury in a defined vascular distribution; or b) symptoms of acute cerebral, spinal, or retinal ischemic injury persisting 24 hours or until death, with other etiologies excluded; 2) hemorrhagic infarction, but not stroke caused by intracerebral or subarachnoid hemorrhage; or 3) strokes not otherwise sub-classified.

As used herein, "high intensity statin therapy" and "high-dose atorvastatin/rosuvastatin" are used interchangeably to refer to administration of 40-80 mg of atorvastatin daily, or 20-40 mg of rosuvastatin daily.

As used herein, "maximally tolerated statin therapy" or "maximum tolerated dose of statin therapy" are used interchangeably to mean a therapeutic regimen comprising the administration of a daily dose of a statin that is the highest dose of statin that can be administered to a particular patient without causing unacceptable adverse side effects in the patient. Maximally tolerated statin therapy includes, but is not limited to, high intensity statin therapy.

As used herein, a patient is regarded as "statin intolerant" or "intolerant to statins" if the patient has a history of experiencing one or more adverse reactions that began or increased while on a daily statin therapeutic regimen and stopped when statin therapy was discontinued. In some embodiments, the adverse reactions are musculoskeletal in nature, such as skeletal muscle pain, aches, weakness or cramping (e.g., myalgia, myopathy, rhabdomyolysis, etc.). Such adverse reactions are often intensified following exercise or exertion. Statin-related adverse reactions also include hepatic, gastrointestinal and psychiatric symptoms that correlate with statin administration. In some embodiments, a patient is deemed "statin intolerant" or "intolerant to statins" if, for example, any of the following applies to the patient: (1) has a history of skeletal muscle-related symptoms associated with at least two different and separate daily statin therapeutic regimens; (2) exhibits one or more statin-related adverse reaction(s) to the lowest approved daily doses of one or more statins; (3) unable to tolerate a cumulative weekly statin dose of seven times the lowest approved tablet size; (4) able to tolerate a low dose statin therapy but develops symptoms when the dose is increased (e.g., to achieve a targeted LDL-C level); or (5) statins are contraindicated for the patient.

As used herein, "not adequately controlled", in reference to hypercholesterolemia, means that the patient's serum low-density lipoprotein cholesterol (LDL-C) concentration, total cholesterol concentration, and/or triglyceride concentration is not reduced to a recognized, medically-acceptable level (taking into account the patient's relative risk of coronary heart disease) after at least 4 weeks on a therapeutic regimen comprising a stable daily dose of a statin. For example, a patient with hypercholesterolemia that is not adequately controlled by a statin includes a patient or patients with a serum LDL-C concentration of greater than or equal to about 70 mg/dL, greater than or equal to about 80 mg/dL, greater than or equal to about 90 mg/dL, greater than or equal to about 100 mg/dL, greater than or equal to about 110 mg/dL, greater than or equal to about 120 mg/dL, greater than or equal to about 130 mg/dL, greater than or equal to about 140 mg/dL, or more (depending on the patient's underlying risk of heart disease) after the patient has been on a stable daily statin regimen for at least 4 weeks.

As used herein, the expression "not adequately controlled", in reference to atherogenic lipoproteins, means that the patient's serum low-density lipoprotein cholesterol (LDL-C) concentration, non-high-density lipoprotein cholesterol, and/or apolipoprotein B concentration are not reduced to a recognized, medically-acceptable level (taking into account the patient's relative risk of coronary heart disease) after at least 4 weeks on a therapeutic regimen comprising a stable daily dose of a statin. For example, a patient with elevated levels of atherogenic lipoproteins that are not adequately controlled by a statin includes a patient or patients with a serum LDL-C concentration of greater than or equal to about 70 mg/dL, greater than or equal to about 80 mg/dL, greater than or equal to about 90 mg/dL, greater than or equal to about 100 mg/dL, greater than or equal to about 110 mg/dL, greater than or equal to about 120 mg/dL, greater than or equal to about 130 mg/dL, greater than or equal to about 140 mg/dL, or more (depending on the patient's underlying risk of heart disease); a non-high-density lipoprotein cholesterol concentration of greater than or equal to about 100 mg/dL; or an apolipoprotein B concentration of greater than or equal to about 80 mg/dL after the patient has been on a stable daily statin regimen for at least 4 weeks.

The present disclosure relates generally to methods and compositions for treating a patient at increased risk of a MACE. In some embodiments, a patient at increased risk of a MACE who is treatable by the methods of the present disclosure has hypercholesterolemia (e.g., a serum LDL-C concentration of greater than or equal to 70 mg/dL, or serum lipoprotein(a) (LPA or LP(a)) level of at least about 30 mg/dL). In some embodiments, a patient at increased risk of a MACE who is treatable by the methods of the present disclosure has received or is currently receiving a high dose of a statin.

The present disclosure also relates generally to methods and compositions for treating a patient at increased risk of a MACE who have elevated levels of atherogenic lipoproteins. In some embodiments, the patient at increased risk of a MACE who is treatable by the methods of the present disclosure has elevated levels of atherogenic lipoproteins (e.g., a serum LDL-C concentration of greater than or equal to 70 mg/dL, or serum lipoprotein(a) (LPA or Lp(a)) level of at least about 30 mg/dL). In some embodiments, a patient at increased risk of a MACE who is treatable by the methods of the present disclosure has received or is currently receiving a high dose of a statin.

The present disclosure relates generally to methods and compositions for lowering the level of serum LDL and lipoprotein(a) in a patient at increased risk of a MACE. In some embodiments, a patient at increased risk of a MACE who is treatable by the methods of the present disclosure has hypercholesterolemia (e.g., a serum LDL-C concentration of greater than or equal to 70 mg/dL, or serum lipoprotein(a) (LPA or LP(a)) level of at least about 50 mg/dL). In some embodiments, a patient at increased risk of a MACE who is treatable by the methods of the present disclosure has received or is currently receiving a high dose of a statin.

The present disclosure also includes methods for treating a patient at increased risk of a MACE with hypercholesterolemia and elevated levels of atherogenic lipoproteins that are not adequately controlled by a maximum tolerated dose of statin therapy. In some embodiments, maximum tolerated dose of statin therapy includes daily administration of statins such as cerivastatin, pitavastatin, fluvastatin, lovastatin, and pravastatin.

Without being limited by any particular theory it is believed that the CAD-PRS calculated according to the methods presented herein allow for identification of MACE risk patients that are most likely to respond to PCSK9 inhibitor therapy. Furthermore, surprisingly and unexpectedly, the CAD-PRS is also predictive of patient response to PCSK9 inhibitor therapy in patients who do not have elevated levels of lipoprotein(a) (LPA or LP(a)) or LDL-C.

In some embodiments, a patient at increased risk of a MACE who is treatable by the methods of the present disclosure has had a MACE within the past 1, 2, 3, 4, 5, 6, 7, 8, 9, 10, 11, 12, 13, 14, 15, 16, 17, or 18 months. The high cardiovascular risk patients who are treatable by the methods of the present disclosure include those patients hospitalized for a MACE.

In some embodiments, the patient at increased risk of a MACE may be selected on the basis of a CAD-PRS, wherein the CAD-PRS comprises a weighted sum of a plurality of genetic variants associated with coronary artery disease and is calculated using at least about 2, at least about 3, at least about 4, at least about 5, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, or at least about 1,000 genetic variants, and if the patient has a CAD-PRS above a threshold score, administering a PCSK9 inhibitor to the subject in an amount effective to lower the level of serum LDL and lipoprotein(a).

Risk assessments using large numbers of genetic variants offers the advantage of increased predictive power. In some embodiments, one or more of the genetic variants is a single nucleotide polymorphism (SNP). In some embodiments, one or more of the genetic variants is an insertion. In some embodiments, one or more of the genetic variants is a deletion. In some embodiments, one or more of the genetic variants is a structural variant. In some embodiments, one or more of the genetic variants is a copy-number variation.

In some embodiments, the disclosure includes in the risk assessment large numbers of alleles, for example, at least about 500,000 genetic variants, at least about 1,000,000 genetic variants, at least about 2,000,000 genetic variants, at least about 3,000,000 genetic variants, at least about 4,000,000 genetic variants, at least about 5,000,000 genetic variants, or at least about 6,000,000 genetic variants, or at least about 6,500,000 genetic variants, or at least about 7,000,000 genetic variants, or at least about 8,000,000 genetic variants, or at least about 9,000,000 genetic variants, or at least about 10,000,000 genetic variants from one or more genetic variant databases, such as, for example, the genetic variant database described in Nikpay et al., Nat Genet., 2015, 47, 1121-1130 ("the Database"), and available at the world wide web at "cardiogramplusc4d.org/media/cardiogramplusc4d-consortium/data-downloads/cad.additive.Oct2015.pub.zip." In some embodiments, risk assessment may comprise assessing all of the genetic variants listed in the Database.

In some embodiments, the present disclosure provides to a method of determining a CAD-PRS in a subject, the method comprising identifying whether at least about 2 genetic variants, at least about 5 genetic variants, at least about 10 genetic variants, at least about genetic variants, at least about 20 genetic variants, at least about 30 genetic variants, at least about 40 genetic variants, at least about 50 genetic variants, at least about 60 genetic variants, at least about 70 genetic variants, at least about 100 genetic variants, at least about 200 genetic variants, at least about 500 genetic variants, at least about 1000 genetic variants, at least about 2000 genetic variants, at least about 5000 genetic variants, at least about 10,000 genetic variants, at least about 20,000 genetic variants, at least about 50,000 genetic variants, at least about 75,000 genetic variants, at least about 100,000 genetic variants, at least about 500,000 genetic variants, at least about 1,000,000 genetic variants, at least about 2,000, 000 genetic variants, at least about 3,000,000 genetic variants, at least about 4,000,000 genetic variants, at least about 5,000,000 genetic variants, or at least about 6,000,000 genetic variants from the Database are present in a biological sample from the subject; wherein the presence of a risk allele increases CAD-PRS, and wherein the presence of an alternative allele decreases CAD-PRS.

In some embodiments, the disclosure provides a method of determining a risk of a MACE in a subject comprising identifying whether the genetic variants from the Database are present in a biological sample from the subject and calculating a CAD-PRS for the subject based on the identified genetic variants, wherein the CAD-PRS is calculated by summing the weighted risk score associated with each genetic variant identified. The number of identified genetic variants can be at least about 2 genetic variants, at least about 5 genetic variants, at least about 10 genetic variants, at least about 15 genetic variants, at least about 20 genetic variants, at least about 30 genetic variants, at least about 40 genetic variants, at least about 50 genetic variants, at least about 95 genetic variants, at least about 100 genetic variants, at least about 200 genetic variants, at least about 500 genetic variants, at least about 1000 genetic variants, at least about 2000 genetic variants, at least about 5000 genetic variants, at least about 10,000 genetic variants, at least about 20,000 genetic variants, at least about 50,000 genetic variants, at least about 75,000 genetic variants, at least about 100,000 genetic variants, at least about 500,000 genetic variants, at least about 1,000,000 genetic variants, at least about 2,000,000 genetic variants, at least about 3,000,000 genetic variants, at least about 4,000,000 genetic variants, at least about 5,000,000 genetic variants, or at least about 6,000,000 genetic variants, or at least about 6,500,000 genetic variants, or at least about 7,000,000 genetic variants, or at least about 8,000,000 genetic variants, or at least about 9,000,000 genetic variants, or at least about 10,000,000 genetic variants.

In some embodiments, the disclosure provides a method of determining a risk of a MACE in a subject comprising identifying whether the genetic variants from the Database are present in a biological sample from the subject, wherein identifying comprises measuring the presence of the at least about 50 genetic variants, at least about 95 genetic variants, at least about 100 genetic variants, at least about 200 genetic variants, at least about 500 genetic variants, at least about 1000 genetic variants, at least about 2000 genetic variants, at least about 5000 genetic variants, at least about 10,000 genetic variants, at least about 20,000 genetic variants, at least about 50,000 genetic variants, at least about 75,000 genetic variants, at least about 100,000 genetic variants, at least about 500,000 genetic variants, at least about 1,000,000 genetic variants, at least about 2,000,000 genetic variants, at least about 3,000,000 genetic variants, at least about 4,000,000 genetic variants, at least about 5,000,000 genetic variants, or at least about 6,000,000 genetic variants, or at least about 6,500,000 genetic variants, or at least about 7,000,000 genetic variants, or at least about 8,000,000 genetic variants, or at least about 9,000,000 genetic variants, or at least about 10,000,000 genetic variants.

In some embodiments, the disclosure provides a method of determining a risk of a MACE in a subject comprising selecting at least about 50 genetic variants, at least about 95 genetic variants, at least about 100 genetic variants, at least about 200 genetic variants, at least about 500 genetic variants, at least about 1000 genetic variants, at least about 2000 genetic variants, at least about 5000 genetic variants, at least about 10,000 genetic variants, at least about 20,000 genetic variants, at least about 50,000 genetic variants, at least about 75,000 genetic variants, at least about 100,000 genetic variants, at least about 500,000 genetic variants, at least about 1,000,000 genetic variants, at least about 2,000,000 genetic variants, at least about 3,000,000 genetic variants, at least about 4,000,000 genetic variants, at least about 5,000,000 genetic variants, or at least about 6,000,000 genetic variants, or at least about 6,500,000 genetic variants, or at least about 7,000,000 genetic variants, or at least about 8,000,000 genetic variants, or at least about 9,000,000 genetic variants, or at least about 10,000,000 genetic variants from the Database; identifying whether the genetic variants are present in a biological sample from the subject; and calculating the PRS based on the presence of the genetic variants.

In some embodiments, the disclosure provides a method of determining a risk of a MACE in a subject comprising identifying whether the genetic variants from the Database are present in a biological sample from the subject, calculating a CAD-PRS for the subject based on the identified genetic variants, and assigning the subject to a risk group based on the CAD-PRS. The CAD-PRS may be divided into quintiles, e.g., top quintile, intermediate quintile, and bottom quintile, wherein the top quintile of polygenic scores correspond the highest genetic risk group and the bottom quintile of polygenic scores correspond to the lowest genetic risk group. The number of identified genetic variants can be at least about 50 genetic variants, at least about 95 genetic variants, at least about 100 genetic variants, at least about 200 genetic variants, at least about 500 genetic variants, at least about 1000 genetic variants, at least about 2000 genetic variants, at least about 5000 genetic variants, at least about 10,000 genetic variants, at least about 20,000 genetic variants, at least about 50,000 genetic variants, at least about 75,000 genetic variants, at least about 100,000 genetic variants, at least about 500,000 genetic variants, at least about 1,000,000 genetic variants, at least about 2,000,000 genetic variants, at least about 3,000,000 genetic variants, at least about 4,000,000 genetic variants, at least about 5,000,000 genetic variants, or at least about 6,000,000 genetic variants, or at least about 6,500,000 genetic variants, or at least about 7,000,000 genetic variants, or at least about 8,000,000 genetic variants, or at least about 9,000,000 genetic variants, or at least about 10,000,000 genetic variants.

In some embodiments, the disclosure provides a method for selecting subjects or candidates with a risk for developing a MACE comprising identifying whether at least about 50 genetic variants, at least about 95 genetic variants, at least about 100 genetic variants, at least about 200 genetic variants, at least about 500 genetic variants, at least about 1000 genetic variants, at least about 2000 genetic variants, at least about 5000 genetic variants, at least about 10,000 genetic variants, at least about 20,000 genetic variants, at least about 50,000 genetic variants, at least about 75,000 genetic variants, at least about 100,000 genetic variants, at least about 500,000 genetic variants, at least about 1,000,000 genetic variants, at least about 2,000,000 genetic variants, at least about 3,000,000 genetic variants, at least about 4,000,000 genetic variants, at least about 5,000,000 genetic variants, or at least about 6,000,000 genetic variants, or at least about 6,500,000 genetic variants, or at least about 7,000,000 genetic variants, or at least about 8,000,000 genetic variants, or at least about 9,000,000 genetic variants, or at least about 10,000,000 genetic variants from the Database are present in a biological sample from each subject or candidate; calculating a polygenic risk score CAD-PRS for each subject or candidate based on the identified genetic variants; and selecting the subjects or candidates with a desired risk group.

For all MACE risk assessments, incorporation of large numbers of genetic variants offers the advantage of increased predictive power. The disclosure further provides risk assessments outlined above incorporating for example, at least 500,000, at least 1,000,000, at least 2,000,000, at least 3,000,000, at least 4,000,000, at least 5,000,000, or at least 6,000,000 genetic variants, or at least 6,500,000 genetic variants, or at least 7,000,000 genetic variants, or at least 8,000,000 genetic variants, or at least 9,000,000 genetic variants, or at least 10,000,000 genetic variants from the Database.

In some embodiments, the disclosure provides a method for selecting a population of subjects or candidates with a high risk for MACE comprising identifying whether at least 50 genetic variants, at least 95 genetic variants, at least 100 genetic variants, at least 200 genetic variants, at least 500 genetic variants, at least 1000 genetic variants, at least 2000 genetic variants, at least 5000 genetic variants, at least 10,000 genetic variants, at least 20,000 genetic variants, at least 50,000 genetic variants, at least 75,000 genetic variants, at least 100,000 genetic variants, at least 500,000 genetic variants, at least 1,000,000 genetic variants, at least 2,000,000 genetic variants, at least 3,000,000 genetic variants, at least 4,000,000 genetic variants, at least 5,000,000 genetic variants, or at least 6,000,000 genetic variants, or at least 6,500,000 genetic variants, or at least 7,000,000 genetic variants, or at least 8,000,000 genetic variants, or at least 9,000,000 genetic variants, or at least 10,000,000 genetic variants from the Database are present in a biological sample from each subject or candidate; calculating a CAD-PRS for each subject or candidate based on the identified genetic variants; and selecting the subjects or candidates in the high risk group.

In some embodiments, the number of identified genetic variants is at least 20 genetic variants. In some embodiments, the number of identified genetic variants is at least 30 genetic variants. In some embodiments, the number of identified genetic variants is at least 40 genetic variants. In some embodiments, the number of identified genetic variants is at least 50 genetic variants. In some embodiments, the number of identified genetic variants is at least 70 genetic variants. In some embodiments, the number of identified genetic variants is at least 100 genetic variants. In some embodiments, the number of identified genetic variants is at least 500 genetic variants. In some embodiments, the number of identified genetic variants is at least 1,000 genetic variants. In some embodiments, the number of identified genetic variants is at least 2,000 genetic variants. In some embodiments, the number of identified genetic variants is at least 5,000 genetic variants. In some embodiments, the number of identified genetic variants is at least 10,000 genetic variants. In some embodiments, the number of identified genetic variants is at least 20,000 genetic variants. In some embodiments, the number of identified genetic variants is at least 50,000 genetic variants. In some embodiments, the number of identified genetic variants is at least 75,000 genetic variants. In some embodiments, the number of identified genetic variants is at least 100,000 genetic variants. In some embodiments, the number of identified genetic variants is at least 500,000 genetic variants. In some embodiments, the number of identified genetic variants is at least 1,000,000 genetic variants. In some embodiments, the number of identified genetic variants is at least 2,000,000 genetic variants. In some embodiments, the number of identified genetic variants is at least 3,000,000 genetic variants. In some embodiments, the number of identified genetic variants is at least 4,000,000 genetic variants. In some embodiments, the number of identified genetic variants is at least 5,000,000 genetic variants. In some embodiments, the number of identified genetic variants is at least 6,000,000 genetic variants. In some embodiments, the number of identified genetic variants is at least 6,500,000 genetic variants. In some embodiments, the number of identified genetic variants is at least 7,000,000 genetic variants. In some embodiments, the number of identified genetic variants is at least 8,000,000 genetic variants. In some embodiments, the number of identified genetic variants is at least 9,000,000 genetic variants. In some embodiments, the number of identified genetic variants is at least 10,000,000 genetic variants.

In some embodiments of the disclosure, risk assessments comprise the highest weighted CAD-PRS scores, including, but not limited to the top 50%, 55%, 60%, 70%, 80%, 90%, or 95% of CAD-PRS scores from a patient population.

In some embodiments, the identified genetic variants comprise the highest risk genetic variants or genetic variants with a weighted risk score in the top 10%, top 20%, top 30%, top 40%, or top 50% in the Database.

In some embodiments, the identified genetic variants comprise the genetic variants having association with MACE in the top 10%, top 20%, top 30%, top 40%, or top 50% of p-value range in the Database. In some embodiments, each of the identified genetic variants comprise the genetic variants having association with MACE with a p-value of not larger than about $10^{-1}$, about $10^{-2}$, about $10^{-3}$, about $10^{-4}$, about $10^{-5}$, about $10^{-6}$, about $10^{-7}$ $10^{-8}$, about $10^{-9}$, about $10^{-10}$, about $10^{-11}$, about $10^{-12}$, about $10^{-13}$, about $10^{-14}$, about or $10^{-15}$ in the Database. In some embodiments, the identified genetic variants comprise the genetic variants having association with MACE with p-value of less than $5 \times 10^{-8}$ in the Database.

In some embodiments, the identified genetic variants comprise genetic variants having association with MACE in high-risk patients as compared to the rest of the reference population with odds ratio (OR) of about 1.0 or greater, about 1.5 or greater, about 1.75 or greater, about 2.0 or greater, or about 2.25 or greater for the top up to 50% of the distribution; or about 1.5 or greater, about 1.75 or greater, about 2.0 or greater, about 2.25 or greater, about 2.5 or greater, or about 2.75 or greater. In some embodiments, the odds ratio (OR) may range from about 1.0 to about 1.5, from about 1.5 to about 2.0, from about 2.0 to about 2.5, from about 2.5 to about 3.0, from about 3.0 to about 3.5, from about 3.5 to about 4.0, from about 4.0 to about 4.5, from about 4.5 to about 5.0, from about 5.0 to about 5.5, from about 5.5 to about 6.0, from about 6.0 to about 6.5, or from about 6.5 to about 7.0. In some embodiments, high-risk patients comprise patients having CAD-PRS scores in the top decile, quintile, or tertile in a reference population.

In some embodiments, the identified genetic variants comprise the genetic variants having the highest genetic variant performance in the reference population. In some embodiments, genetic variant performance is calculated with respect to coronary artery disease risk based on statistical significance, strength of association, and/or a probability distribution.

In some embodiments, genetic variant scores are calculated using PRS calculation methodologies, such as the LDPred method (or variations and/or versions thereof), which is a Bayesian approach to calculate a posterior mean effect for all variants based on a prior (effect size in the prior GWAS) and subsequent shrinkage based on linkage disequilibrium. LDPred creates a PRS using genome-wide variation with weights derived from a set of GWAS summary statistics. See, Vilhjálmsson et al., Am. J. Hum. Genet., 2015, 97, 576-92. In some embodiments, alternate approaches for calculating genetic variant scores may be used, including SBayesR (Lloyd-Jones, L R, world wide web at "biorxiv.org/content/biorxiv/early/2019/01/17/522961.full.pdf"), Pruning and Thresholding (P&T) (Purcell, Nature, 2009, 460, 748-752), and COJO (Yang et al., Nat. Genet., 2012, 44, 369-375). SBayesR is a Bayesian approach is similar to LDPred but allows for more flexibility in the posterior mean effects. Pruning and Thresholding requires that a minimum p-value threshold (p-value associated with the variant from the source data file) and $r^2$ threshold (measure of LD) between variants be specified. P&T identifies the variant with the smallest p-value in each region and then "clumps" under that variant all other variants in the region with an $r^2$ value that is larger than the specified $r^2$. In the PRS, the index variant represents all the variants in the clump (only the index variant is included in the PRS, all other variants are excluded). COJO, or conditional and joint association analysis, is similar conceptually to P&T but incorporates additional variants in a given LD block into the score if they demonstrate independent contribution to disease risk after conditioning on the index variant.

In some embodiments, genetic variant performance is calculated using the LDPred method, wherein the p value is from about 0.0001 to about 0.5. In some embodiments, genetic variant performance is calculated using the LDPred method, wherein the ρ value is about 0.5. In some embodiments, genetic variant performance is calculated using the LDPred method, wherein the ρ value is about 0.1. In some embodiments, genetic variant performance is calculated using the LDPred method, wherein the ρ value is about 0.05. In some embodiments, genetic variant performance is calculated using the LDPred method, wherein the ρ value is about 0.01. In some embodiments, genetic variant performance is calculated using the LDPred method, wherein the ρ value is about 0.005. In some embodiments, genetic variant performance is calculated using the LDpred method, wherein the ρ value is about 0.001. In some embodiments, genetic variant performance is calculated using the LDPred method, wherein the ρ value is about 0.0005. In some embodiments, genetic variant performance is calculated using the LDPred method, wherein the ρ value is about 0.0001.

In some embodiments, the method further comprises an initial step of obtaining a biological sample from the subject.

As used herein, a "biological sample" may contain whole cells and/or live cells and/or cell debris. The biological sample may contain (or be derived from) a "bodily fluid". The present disclosure encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

In some embodiments, the method is used to select a population of subjects or candidates for clinical trials, e.g., a clinical trial to determine whether a particular treatment or treatment plan is effective against a MACE or a recurring MACE. In some embodiments, the selected candidates or subjects are divided into subgroups based on the identified genetic variants for each subject or candidate, and the method is used to determine whether a particular treatment or treatment plan is effective against a particular genetic variant or a particular group of genetic variants. In other word, the method can be employed to determine susceptibility of a population of subjects to a particular treatment or treatment plan, wherein the population of subjects is selected based on the genetic variants identified in the subjects.

In some embodiments, the method is used to select a population of subjects or candidates for clinical trials, e.g., a clinical trial to determine whether a particular treatment or treatment plan is effective against a MACE or recurring MACE. In some embodiments, the desired risk group is a population comprising high risk subjects or candidates. In some embodiments, the selected population of subjects or candidates are responders, i.e., the subjects or candidates are responsive to the treatment or treatment plan.

In some embodiments the subjects are selected based on CAD-PRS alone. For example, if a patient or a candidate subject that have CAD-PRS above a pre-determined threshold, the patient is selected for initiating treatment or a candidate subject is included in the clinical trial. In some embodiments, the threshold for treatment initiation or clinical trial inclusion is determined in relative terms. For example, in some embodiments the threshold CAD-PRS score is top 50% within a reference population. In some embodiments, embodiments the threshold CAD-PRS score is top 40% within a reference population. In some embodiments, embodiments the threshold CAD-PRS score is top 30% within a reference population. In some embodiments, embodiments the threshold CAD-PRS score is top 25% within a reference population. In some embodiments, embodiments the threshold CAD-PRS score is top 20% within a reference population. In some embodiments, embodiments the threshold CAD-PRS score is top 15% within a reference population. In some embodiments, embodiments the threshold CAD-PRS score is top 10% (decile) within a reference population. In some embodiments, embodiments the threshold CAD-PRS score is top 5% within a reference population.

In some embodiments, the reference population for determination of relative CAD-PRS score is at least about 100 patients. In some embodiments, the reference population for determination of relative CAD-PRS score is at least about 200 patients. In some embodiments, the reference population for determination of relative CAD-PRS score is at least about 500 patients. In some embodiments, the reference population for determination of relative CAD-PRS score is at least about 1,000 patients. In some embodiments, the reference population for determination of relative CAD-PRS score is at least about 3,000 patients. In some embodiments, the reference population for determination of relative CAD-PRS score is at least about 5,000 patients. In some embodiments, the reference population for determination of relative CAD-PRS score is at least about 7,500 patients. In some embodiments, the reference population for determination of relative CAD-PRS score is at least about 10,000 patients. In some embodiments, the reference population for determination of relative CAD-PRS score is at least about 12,000 patients. In some embodiments, the reference population for determination of relative CAD-PRS score is at least about 15,000 patients. In some embodiments, the reference population for determination of relative CAD-PRS score is at least about 20,000 patients. In some embodiments, the reference population for determination of relative CAD-PRS score is at least about 30,000 patients. In some embodiments, the reference population for determination of relative CAD-PRS score is at least about 50,000 patients. In some embodiments, the reference population for determination of relative CAD-PRS score is at least about 70,000 patients. In some embodiments, the reference population for determination of relative CAD-PRS score is at least about 100,000 patients.

In some embodiments, the reference population is enriched for members of an ancestry group. In some embodiments, the ancestry group is self-reported. In some embodiments, the ancestry group is derived from a principal component analysis of ancestry. In some embodiments the ancestry group is European. In some embodiments the ancestry group is African. In some embodiments the ancestry group is Ad mixed American. In some embodiments the ancestry group is East Asian. In some embodiments the ancestry group is South Asian. In some embodiments the ancestry group is any mixture of any two or more of the European, African, Ad mixed American, East Asian, and South Asian populations.

In some embodiments, the method further comprises determining a composite risk score comprising the CAD-PRS and the level of low-density lipoprotein (LDL) in a biological sample obtained from the patient. For example, if a patient or a candidate subject that have both CAD-PRS and LDL level in a biological sample obtained from the patient or a test subject above a pre-determined threshold, the patient is selected for initiating treatment or a candidate subject is included in the clinical trial. In some embodiments, the biological sample comprises blood serum. In some embodiments, the threshold serum LDL level is at least about 100 mg/dL. In some embodiments, the threshold serum LDL level is at least about 120 mg/dL. In some embodiments, the threshold serum LDL level is at least about 140 mg/dL. In some embodiments, the threshold serum LDL level is at least about 160 mg/dL. In some embodiments, the threshold serum LDL level is at least about 180 mg/dL. In some embodiments, the threshold serum LDL level is at least about 200 mg/dL.

In some embodiments, the method further comprises determining a composite risk score comprising the CAD-PRS and the level of lipoprotein(a) (LPA or LP(a)) in a biological sample obtained from the patient. For example, if a patient or a candidate subject that have both CAD-PRS and LPA level in a biological sample obtained from the patient or a test subject above a pre-determined threshold, the patient is selected for initiating treatment or a candidate subject is included in the clinical trial. In some embodiments, the biological sample comprises blood serum. In some embodiments, the threshold serum LPA level is at least about 30 mg/dL. In some embodiments, the threshold serum LPA level is at least about 40 mg/dL. In some embodiments, the threshold serum LPA level is at least about 50 mg/dL. In some embodiments, the threshold serum LPA level is at least about 120 mg/dL. In some embodiments, the threshold serum LPA level is at least about 60 mg/dL. In some embodiments, the threshold serum LPA level is at least about 70 mg/dL. In some embodiments, the threshold serum LPA level is at least about 80 mg/dL. In some embodiments, the threshold serum LPA level is at least about 100 mg/dL. In some embodiments, the threshold serum LPA level is at least about 120 mg/dL. In some embodiments, the threshold serum LPA level is at least about 140 mg/dL.

In some embodiments, the method further comprises determining a composite risk score comprising the CAD-PRS, the level of LPA, and the level of LDL-C in a biological sample obtained from the patient. For example, if a patient or a candidate subject that have CAD-PRS and both LDL and LPA levels in a biological sample obtained from the patient or a test subject above a pre-determined threshold, the patient is selected for initiating treatment or a candidate subject is included in the clinical trial.

In some embodiments, the method further comprises determining a composite risk score comprising the CAD-PRS and the level of LPA in a biological sample obtained from the patient. In some embodiments, the method further comprises determining a composite risk score comprising the CAD-PRS, the level of LDL, and the level of LPA in a biological sample obtained from the patient. In some embodiments, the method further comprises determining a composite risk score comprising the CAD-PRS and the Framingham (FHS) recurrent risk score (see, D'Agostino et al., Am. Heart J., 2000, 139, 272-281) in a biological sample obtained from the patient. In some embodiments, the method further comprises determining a composite risk score comprising the CAD-PRS and the very high risk (VHR) groups (Roe et al., Circulation, 2019, 140, 1578-1589) in a biological sample obtained from the patient. Thus, in some embodiments, the composite risk score can comprise the CAD-PRS and any one or more of the level of LPA, the level of LDL, the Framingham (FHS) recurrent risk score, and the VHR groups in a biological sample obtained from the patient. In some embodiments, the biological sample comprises blood.

In some embodiments, the method further comprises initiating a treatment to the subject. The treatment can comprise statins, ezetimibe, beta-blocking agents, angiotensin-converting-enzyme inhibitors, aspirin, anticoagulants, antiplatelet agents, angiotensin II receptor blockers, angiotensin receptor neprilysin inhibitors, calcium channel blockers, cholesterol-lowering medications, vasodilators, antidiuretics, renin-angiotensin system agents, lipid-modifying medicines, anti-inflammatory agents, nitrates, antiarrhythmic medicines, steroidal or non-steroidal anti-inflammatory drugs, DNA methyltransferase inhibitors and/or histone deacetylase inhibitors. The DNA methyltransferase inhibitors can be any DNA methyltransferase known in the art, e.g., 5-aza-2'-deoxycytidine or 5-azacytidine. The histone deacetylase inhibitors can be any histone deacetylase inhibitors known in the art, e.g., varinostat, romidepsin, panobinostat, belinostat or entinostat. The statins can be any statins known in the art, e.g., atorvastatin, fluvastatin, lovastatin, pravastatin, rosuvastatin, and simvastatin. The lipid-modifying medicines can be any lipid-modifying compounds known in the art, e.g., an inhibitor of PCSK9, an antisense oligonucleotide targeting apolipoprotein C-Ill, and an antisense oligonucleotide to lower lipoprotein(a).

Initiating a treatment can include devising a treatment plan based on the risk group, which corresponds to the CAD-PRS calculated for the patient. In some embodiments, CAD-PRS is predictive of treatment efficacy or of patient's response to a therapeutic regimen. In some embodiments the composite risk score (CAD-PRS combined with LDL levels, LPA levels, or both) is predictive of treatment efficacy of patient's response to a therapeutic regimen. Accordingly, the treatment can be determined or adjusted according to the CAD-PRS.

In some embodiments, the treatment initiation comprises modifying dosage or regimen of a treatment that a MACE risk or hypercholesterolemia patient already receives (e.g. treatment with statins that does not adequately control hypercholesterolemia) based on CAD-PRS calculated for the patient. In some embodiments, the treatment initiation comprises substitution of one therapeutic agent with another based on CAD-PRS calculated for the MACE risk or hypercholesterolemia patient, for example if patient is intolerant to statin. In some embodiments, the treatment initiation comprises starting a regimen of a therapeutic agent in addition to a therapeutic agent a patient already receives, for example starting a PCSK9 inhibitor regimen in a MACE risk or hypercholesterolemia patient receiving a statins treatment, such as high intensity statin therapy or maximally tolerated statin therapy. In some embodiments, the treatment initiation comprises starting administration of a therapeutic regimen to a previously untreated MACE risk or hypercholesterolemia patient.

In some embodiments, the therapeutic agent is an inhibitor of human PCSK9. In some embodiments, CAD-PRS is predictive of treatment efficacy or of a patient's response to PCSK9 inhibition treatment. In some embodiments the composite risk score (CAD-PRS combined with LDL levels, LPA levels, or both) is predictive of a patient's response to PCSK9 inhibitor treatment. Accordingly, the PCSK9 inhibitor treatment can be determined or adjusted according to the CAD-PRS calculated for the patient.

The term "proprotein convertase subtilisin-kexin type 9" or "PCSK9", as used herein, refers to human PCSK9 having the nucleic acid sequence shown in

```
SEQ. ID NO: 1:
GTCCGATGGGGCTCTGGTGGCGTGATCTGCGCGCCCCAGGCGTCAAGCAC
CCACACCCTAGAAGGTTTCCGCAGCGACGTCGAGGCGCTCATGGTTGCAG
GCGGGCGCCGCCGTTCAGTTCAGGGTCTGAGCCTGGAGGAGTGAGCCAGG
CAGTGAGACTGGCTCGGGCGGGCCGGGACGCGTCGTTGCAGCAGCGGCTC
CCAGCTCCCAGCCAGGATTCCGCGCGCCCCTTCACGCGCCCTGCTCCTGA
ACTTCAGCTCCTGCACAGTCCTCCCCACCGCAAGGCTCAAGGCGCCGCCG
GCGTGGACCGCGCACGGCCTCTAGGTCTCCTCGCCAGGACAGCAACCTCT
CCCCTGGCCCTCATGGGCACCGTCAGCTCCAGGCGGTCCTGGTGGCCGCT
GCCACTGCTGCTGCTGCTGCTGCTGCTCCTGGGTCCCGCGGGCGCCCGTG
CGCAGGAGGACGAGGACGGCGACTACGAGGAGCTGGTGCTAGCCTTGCGT
TCCGAGGAGGACGGCCTGGCCGAAGCACCCGAGCACGGAACCACAGCCAC
CTTCCACCGCTGCGCCAAGGATCCGTGGAGGTTGCCTGGCACCTACGTGG
TGGTGCTGAAGGAGGAGACCCACCTCTCGCAGTCAGAGCGCACTGCCCGC
CGCCTGCAGGCCCAGGCTGCCCGCCGGGGATACCTCACCAAGATCCTGCA
TGTCTTCCATGGCCTTCTTCCTGGCTTCCTGGTGAAGATGAGTGGCGACC
TGCTGGAGCTGGCCTTGAAGTTGCCCCATGTCGACTACATCGAGGAGGAC
TCCTCTGTCTTTGCCCAGAGCATCCGTGGAACCTGGAGCGGATTACCCC
TCCACGGTACCGGGCGGATGAATACCAGCCCCCCGACGGAGGCAGCCTGG
TGGAGGTGTATCTCCTAGACACCAGCATACAGAGTGACCACCGGGAAATC
GAGGGCAGGGTCATGGTCACCGACTTCGAGAATGTGCCCGAGGAGGACGG
GACCCGCTTCCACAGACAGGCCAGCAAGTGTGACAGTCATGGCACCCACC
```

```
-continued
TGGCAGGGGTGGTCAGCGGCCGGGATGCCGGCGTGGCCAAGGGTGCCAGC
ATGCGCAGCCTGCGCGTGCTCAACTGCCAAGGGAAGGGCACGGTTAGCGG
CACCCTCATAGGCCTGGAGTTTATTCGGAAAAGCCAGCTGGTCCAGCCTG
TGGGGCCACTGGTGGTGCTGCTGCCCCTGGCGGGTGGGTACAGCCGCGTC
CTCAACGCCGCCTGCCAGCGCCTGGCGAGGGCTGGGGTCGTGCTGGTCAC
CGCTGCCGGCAACTTCCGGGACGATGCCTGCCTCTACTCCCCAGCCTCAG
CTCCCGAGGTCATCACAGTTGGGGCCACCAATGCCCAAGACCAGCCGGTG
ACCCTGGGGACTTTGGGGACCAACTTTGGCCGCTGTGTGGACCTCTTTGC
CCCAGGGGAGGACATCATTGGTGCCTCCAGCGACTGCAGCACCTGCTTTG
TGTCACAGAGTGGGACATCACAGGCTGCTGCCCACGTGGCTGGCATTGCA
GCCATGATGCTGTCTGCCGAGCCGGAGCTCACCCTGGCCGAGTTGAGGCA
GAGACTGATCCACTTCTCTGCCAAAGATGTCATCAATGAGGCCTGGTTCC
CTGAGGACCAGCGGGTACTGACCCCCAACCTGGTGGCCGCCCTGCCCCCC
AGCACCCATGGGCAGGTTGGCAGCTGTTTTGCAGGACTGTATGGTCAGC
ACACTCGGGGCCTACACGGATGGCCACAGCCGTCGCCCGCTGCGCCCCAG
ATGAGGAGCTGCTGAGCTGCTCCAGTTTCTCCAGGAGTGGGAAGCGGCGG
GGCGAGCGCATGGAGGCCCAAGGGGGCAAGCTGGTCTGCCGGGCCCACAA
CGCTTTTGGGGGTGAGGGTGTCTACGCCATTGCCAGGTGCTGCCTGCTAC
CCCAGGCCAACTGCAGCGTCCACACAGCTCCACCAGCTGAGGCCAGCATG
GGGACCCGTGTCCACTGCCACCAACAGGGCCACGTCCTCACAGGCTGCAG
CTCCCACTGGGAGGTGGAGGACCTTGGCACCCACAAGCCGCCTGTGCTGA
GGCCACGAGGTCAGCCCAACCAGTGCGTGGGCCACAGGGAGGCCAGCATC
CACGCTTCCTGCTGCCATGCCCCAGGTCTGGAATGCAAAGTCAAGGAGCA
TGGAATCCCGGCCCCTCAGGAGCAGGTGACCGTGGCCTGCGAGGAGGGCT
GGACCCTGACTGGCTGCAGTGCCCTCCCTGGGACCTCCCACGTCCTGGGG
GCCTACGCCGTAGACAACACGTGTGTAGTCAGGAGCCGGGACGTCAGCAC
TACAGGCAGCACCAGCGAAGGGGCCGTGACAGCCGTTGCCATCTGCTGCC
GGAGCCGGCACCTGGCGCAGGCCTCCCAGGAGCTCCAGTGACAGCCCCAT
CCCAGGATGGGTGTCTGGGGAGGGTCAAGGGCTGGGGCTGAGCTTTAAAA
TGGTTCCGACTTGTCCCTCTCTCAGCCCTCCATGGCCTGGCACGAGGGGA
TGGGGATGCTTCCGCCTTTCCGGGGCTGCTGGCCTGGCCCTTGAGTGGGG
CAGCCTCCTTGCCTGGAACTCACTCACTCTGGGTGCCTCCTCCCCAGGTG
GAGGTGCCAGGAAGCTCCCTCCCTCACTGTGGGGCATTTCACCATTCAAA
CAGGTCGAGCTGTGCTCGGGTGCTGCCAGCTGCTCCCAATGTGCCGATGT
CCGTGGGCAGAATGACTTTTATTGAGCTCTTGTTCCGTGCCAGGCATTCA
ATCCTCAGGTCTCCACCAAGGAGGCAGGATTCTTCCCATGGATAGGGGAG
GGGGCGGTAGGGGCTGCAGGGACAAACATCGTTGGGGGGTGAGTGTGAAA
GGTGCTGATGGCCCTCATCTCCAGCTAACTGTGGAGAAGCCCCTGGGGGC
TCCCTGATTAATGGAGGCTTAGCTTTCTGGATGGCATCTAGCCAGAGGCT
GGAGACAGGTGCGCCCCTGGTGGTCACAGGCTGTGCCTTGGTTTCCTGAG
CCACCTTTACTCTGCTCTATGCCAGGCTGTGCTAGCAACACCCAAAGGTG
```

-continued

```
GCCTGCGGGGAGCCATCACCTAGGACTGACTCGGCAGTGTGCAGTGGTGC

ATGCACTGTCTCAGCCAACCCGCTCCACTACCCGGCAGGGTACACATTCG

CACCCCTACTTCACAGAGGAAGAAACCTGGAACCAGAGGGGCGTGCCTG

CCAAGCTCACACAGCAGGAACTGAGCCAGAAACGCAGATTGGGCTGGCTC

TGAAGCCAAGCCTCTTCTTACTTCACCCGGCTGGGCTCCTCATTTTTACG

GGTAACAGTGAGGCTGGGAAGGGGAACACAGACCAGGAAGCTCGGTGAGT

GATGGCAGAACGATGCCTGCAGGCATGGAACTTTTTCCGTTATCACCCAG

GCCTGATTCACTGGCCTGGCGGAGATGCTTCTAAGGCATGGTCGGGGAG

AGGGCCAACAACTGTCCCTCCTTGAGCACCAGCCCCACCCAAGCAAGCAG

ACATTTATCTTTTGGGTCTGTCCTCTCTGTTGCCTTTTTACAGCCAACTT

TTCTAGACCTGTTTTGCTTTTGTAACTTGAAGATATTTATTCTGGGTTTT

GTAGCATTTTTATTAATATGGTGACTTTTTAAAATAAAAACAAACAAACG

TTGTCCTAACAAAAAAAAAAAAAAAAAAAAA;
and the amino acid sequence of SEQ. ID NO: 2:
MGTVSSRRSWWPLPLLLLLLLLLGPAGARAQEDEDGDYEELVLALRSEED

GLAEAPEHGTTATFHRCAKDPWRLPGTYVVVLKEETHLSQSERTARRLQA

QAARRGYLTKILHVFHGLLPGFLVKMSGDLLELALKLPHVDYIEEDSSVF

AQSIPWNLERITPPRYRADEYQPPDGGSLVEVYLLDTSIQSDHREIEGRV

MVTDFENVPEEDGTRFHRQASKCDSHGTHLAGVVSGRDAGVAKGASMRSL

RVLNCQGKGTVSGTLIGLEFIRKSQLVQPVGPLVVLLPLAGGYSRVLNAA

CQRLARAGVVLVTAAGNFRDDACLYSPASAPEVITVGATNAQDQPVTLGT

LGTNFGRCVDLFAPGEDIIGASSDCSTCFVSQSGTSQAAAHVAGIAAMML

SAEPELTLAELRQRLIHFSAKDVINEAWFPEDQRVLTPNLVAALPPSTHG

AGWQLFCRTVWSAHSGPTRMATAVARCAPDEELLSCSSFSRSGKRRGERM

EAQGGKLVCRAHNAFGGEGVYAIARCCLLPQANCSVHTAPPAEASMGTRV

HCHQQGHVLTGCSSHWEVEDLGTHKPPVLRPRGQPNQCVGHREASIHASC

CHAPGLECKVKEHGIPAPQEQVTVACEEGWTLTGC,
``` or a biologically active fragment thereof.

As used herein, the term "inhibitor" means either that a given compound is capable of inhibiting the activity of the respective protein or other substance in the cell at least to a certain amount. This can be achieved by a direct interaction of the compound with the given protein or substance ("direct inhibition") or by an interaction of the compound with other proteins or other substances in or outside the cell which leads to an at least partial inhibition of the activity of the protein or substance ("indirect inhibition"). Inhibition of protein activity can also be achieved through suppressing the expression of a target protein. Techniques of inhibiting protein expression include, but not limited to, antisense inhibition, siRNA-mediated inhibition, miRNA mediated inhibition, rybozyme-mediated inhibition, DNA-directed RNA interference (DdRNAi), RNA-directed DNA methylation, transcription activator-like effector nucleases (TALEN)-mediated inhibition, zinc finger nuclease-mediated inhibition, aptamer-mediated inhibition, and CRISPR-mediated inhibition.

As used herein, "antisense inhibition" means reduction of target nucleic acid levels in the presence of an oligonucleotide complementary to a target nucleic acid compared to target nucleic acid levels in the absence of the oligonucleotide.

In some embodiments, the PCSK9 inhibitor is a small molecule. Numerous small molecule inhibitors of PCSK9 are described, for example, in U.S. Pat. No. 10,131,637.

In some embodiments, the PCSK9 inhibitor is an siRNA. An exemplary siRNA includes, but is not limited to inclisiran (see, Ray et al., Circulation, 2018, 138, 1304-1316). In some embodiments, the PCSK9 inhibitor is an anti-PCSK9 antibody or an antigen binding portion thereof. The term "antibody," as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the anti-PCSK9 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Anti-PCSK9 antibodies include, but are not limited to, evolocumab, alirocumab, and bococizumab. Additional anti-PCSK9 antibodies are described, for example, in U.S. Pat. Nos. 10,259,885, 10,023,654, 9,266,961, 9,561,155, 9,550, 837, 9,540,449, 9,029,515, 8,951,523, 8,859,741, 8,530,414, 8,829,165, 8,802,827, 8,710,192, 8,344,114, and 8,188,233. Additional anti-PCSK9 antibodies include antibodies that comprise the $V_H$, $V_L$, and/or CDRs of evolocumab, alirocumab, or bococizumab.

In the context of the methods, additional therapeutically active component(s), e.g., any of the agents listed above or derivatives thereof, may be administered just prior to, concurrent with, or shortly after the administration of a PCSK9 inhibitor; (for purposes of the present disclosure, such administration regimens are considered the administration of a PCSK9 inhibitor "in combination with" an additional therapeutically active component). The present methods include pharmaceutical compositions and methods of use thereof in which a PCSK9 inhibitor is co-formulated with one or more of the additional therapeutically active component(s) as described elsewhere herein.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: ODYSSEY OUTCOMES Clinical Trial

The ODYSSEY OUTCOMES trial was a randomized, double-blind comparison of alirocumab or placebo in 18,924 patients with a recent hospitalization (1 to 12 months prior) for ACS (myocardial infarction or unstable angina). Qualifying patients had an LDL-C cholesterol level of ≥70 mg per deciliter, an apolipoprotein B level of 80 mg per deciliter, or a non-HDL cholesterol level of ≥100 mg per deciliter despite high-intensity or maximum-tolerated statin treatment. Patients were allocated in a 1:1 ratio to either alirocumab or matching placebo every two weeks. The primary endpoint, MACE, was a composite of death from coronary heart disease, nonfatal myocardial infarction, ischemic stroke, or unstable angina requiring hospitalization. Median follow-up was 2.8 years. MACE occurred in 1052 patients (11.1%) in the placebo group and 903 patients (9.5%) in the alirocumab group (hazard ratio (HR), 0.85; 95% confidence interval (CI), 0.78 to 0.93; P-value<0.001).

Generation of Genetic Data

DNA samples were available from 12,118 trial participants who provided written informed consent to participate in the pharmacogenomics study. Samples were genotyped on the Illumina Global Screening Array (GSA), v1.0. Additional genetic data were imputed using the program Minimac3. Reference populations for imputation were obtained from 1000 Genomes phase 3 version 5 data. Of the 12,118 samples, 11,953 (98%) met the quality control procedures for genetic data.

Genetic variants and summary statistics used for the development of the PRS were obtained from a genome-wide meta-analysis of coronary artery disease in 60,801 cases and 123,504 controls. These variants (up to n=6,579,025) and their corresponding disease association effect sizes (odds ratios) were used in developing the genome-wide PRS using the Pruning and Threshold (P&T) approach and LDPred algorithm. For comparison to previous publications of CAD PRS in statin response, 27- and 57-variant models were also evaluated. PRS were calculated for each patient by taking the product of the number of patient risk alleles and respective variant weights (log odds ratio or LDPred-adjusted log odds ratio) for each variant and summing across all variants. These scores were tested and validated using two large and independent databases DiscovEHR (n=84,243), and UK Biobank (n=446,208). ODYSSEY OUTCOMES trial patients were assigned to one of five ancestral groups (African, Ad Mixed American, East Asian, European, or South Asian). Ancestral population classification was made based on the similarity between each patient's genotypes and publicly available genetic data from the International HapMap project. The population structure was assessed using principal components analysis with plink software. The subsequent risk score calculations were stratified by ancestry. Within each ancestral group, PRS were standardized to a mean of zero and standard deviation of 1 and datasets were combined to allow for cross-ancestry comparisons. High genetic risk was defined as patients within the top decile of the distribution of the PRS (>90th PRS percentile). Those below the top decile were defined as lower genetic risk (≤90th PRS percentile). This threshold was selected in a post hoc analysis that evaluated high genetic risk thresholds ranging from 50% to 90%, in 10% increments. The PRS as a continuous measure was also evaluated.

Genetic Data Processing

Genotyping Methodology.

The Illumina Global Screening Array (GSA), v1.0 (GSA-24v1-0_A1) was used to generate microarray genotypes for the genome-wide association study (GWAS). This array contains about 660,000 markers, with an average marker spacing of 4.2 kb.

Illumina Microarray Genotyping Data QC.

Individual samples with a call rate <90% and genetic variants with a call rate <90% or Hardy-Weinberg Equilibrium p-value <1×10$^{-6}$ were removed from the analysis. In paired samples with IBD≥0.25, the sample with the lower call rate was removed. Samples were also removed if gender discordance was detected between X-chromosome inferred gender and the gender reported in the clinical database.

Principal Component Analysis (PCA).

The population structure was assessed using PCA within plink version 1.9. Two sets of analyses were performed: 1) Assignment of ancestral groups; and 2) Generation of ancestry-specific PCs. The ancestral population assignment is based on the similarity between each patient's genotypes and publicly available genetic data from the International HapMap project. PCA was performed in a merged dataset of ODYSSEY CVOT and HapMap samples. The likelihood of each sample belonging to one of five HapMap super populations/ancestral groups (African (AFR); Ad Mixed American (AMR), East Asian (EAS), European (EUR), or South Asian (SAS)) was calculated and used to classify the sample. PCA was performed in the overall PGx population and within ancestry group to generate ancestry-specific PCs. The top 4-12 PCs (depending on ancestry) were used as covariates in analyses.

Imputation.

Genotype imputation was conducted with Minimac3. Reference populations for imputation were obtained from 1000 Genomes phase 3 version 5. Post-QC variants were restricted to those with INFO score >0.3. Similar thresholds with respect to missingness and HWE were applied. For imputed variants, allele dosages were used in calculating the PRS.

Generation of Polygenic Risk Scores

Datasets.

The primary data source for the polygenic risk score comes from a GWAS of CAD risk comprising 9.4 million variants from a meta-analysis of 60,801 CAD cases and 123,504 controls. A set of PRS algorithm tuning parameters was evaluated based on their performance in two datasets, UK Biobank (UKB) and DiscovEHR. A composite cardiovascular endpoint of myocardial infarction, unstable angina, and ischemic stroke (as defined by ICD-10 codes I21*, I22*, I23*, I24.1, I25.2, I2.0, I63.0), along with self-report codes 20002* (UKB) was used to define case and control status.

PRS Algorithm Selection.

Three approaches for generating polygenic risk scores were tested; candidate SNP models from previous work on PRS benefit in statins, comprising 27 and 57 variants, Pruning and Thresholding (P&T), and LDPred. P&T identifies the variant with the smallest p-value in each region and then "clumps" under that variant all other variants in the region with an $r^2$ value that is larger than the specified $r^2$. In the PRS, the index variant represents all the variants in the clump (only the index variant is included in the PRS, all other variants are excluded). LDPred is a Bayesian approach to PRS development that calculates a posterior mean effect (adjusted effect size) for all variants based on a prior and LD information from a reference panel. Heuristically, the effect sizes generated from LDPred differs from P&T in that LDPred jointly models the effect size and variance of each marker, incorporating the LD structure when shrinking the effect sizes. Adjustment or shrinkage of variant weights is based not only on magnitude of variant association with disease but also linkage disequilibrium (LD) between variants. For both P&T and LDPred approaches, 1000 Genomes phase 3 version 5 data was used for the LD reference panel.

PRS Calculation.

From either the LDPred or P&T approach, a set of variants and their respective weights were generated. In the case of P&T, the weights were the log odds ratio from the meta-analysis source data. In the case of LDPred, the variant weights are the adjusted log odds ratio (posterior mean). After generation of weights, the process for calculating and normalizing scores is identical. For a set of i=1, . . . , M variants in j=1, . . . N patients, the PRS for patient j is calculated by:

$$PRS_{ij} = \sum_{i=1}^{M} (B_i x_{ij}),$$

where $B_i$ is the log odds ratio for variant i and $x_{ij}$ is the number of risk alleles carried by patient j at variant i (for imputed variants, the allele dosage for variant i). Scores were standardized to ~N(0,1) by subtracting the mean PRS and dividing by the PRS standard deviation within each ancestry group.

Testing and Validating PRS Algorithms.

Figure 9:
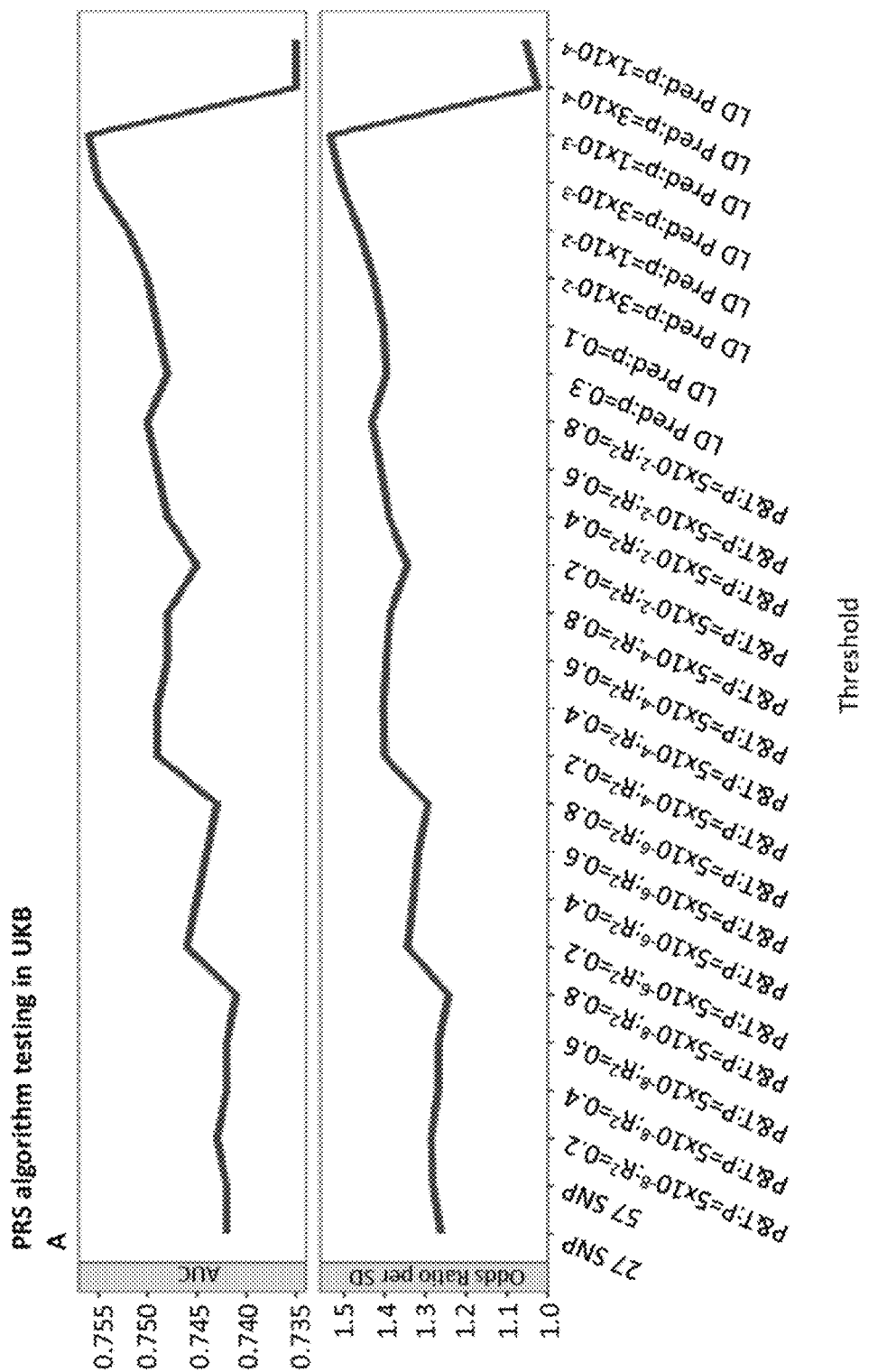
FIG. 9 shows candidate SNP (27-57), pruning and thresholding (P&T), and LDPred results in UK Biobank (UKB) testing data set. Results are shown for the composite endpoint of myocardial infarction, angina, or ischemic stroke. Panel A shows the area under the curve (AUC) and odds ratio per SD for each candidate SNP list or set of algorithm tuning parameters. Panel B displays the number of markers used to generate the genetic risk score for each tuning parameter.
Figure 9:
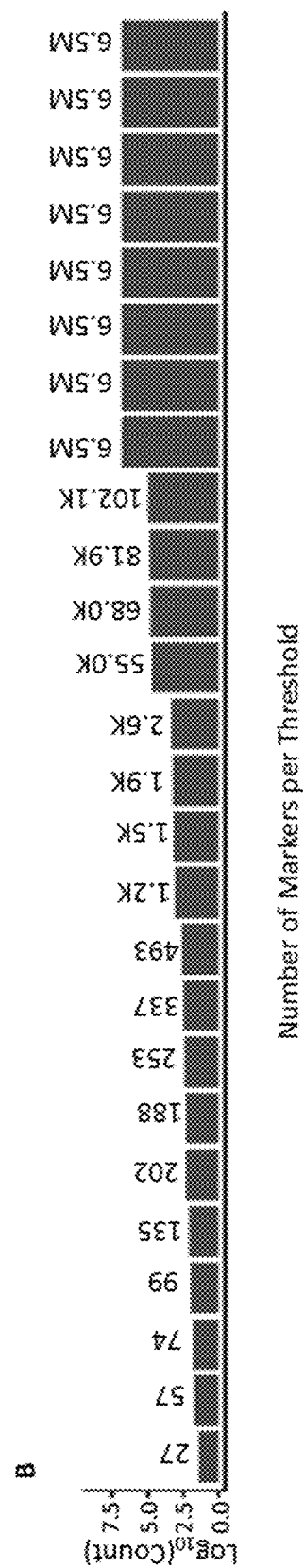
Figure 10:
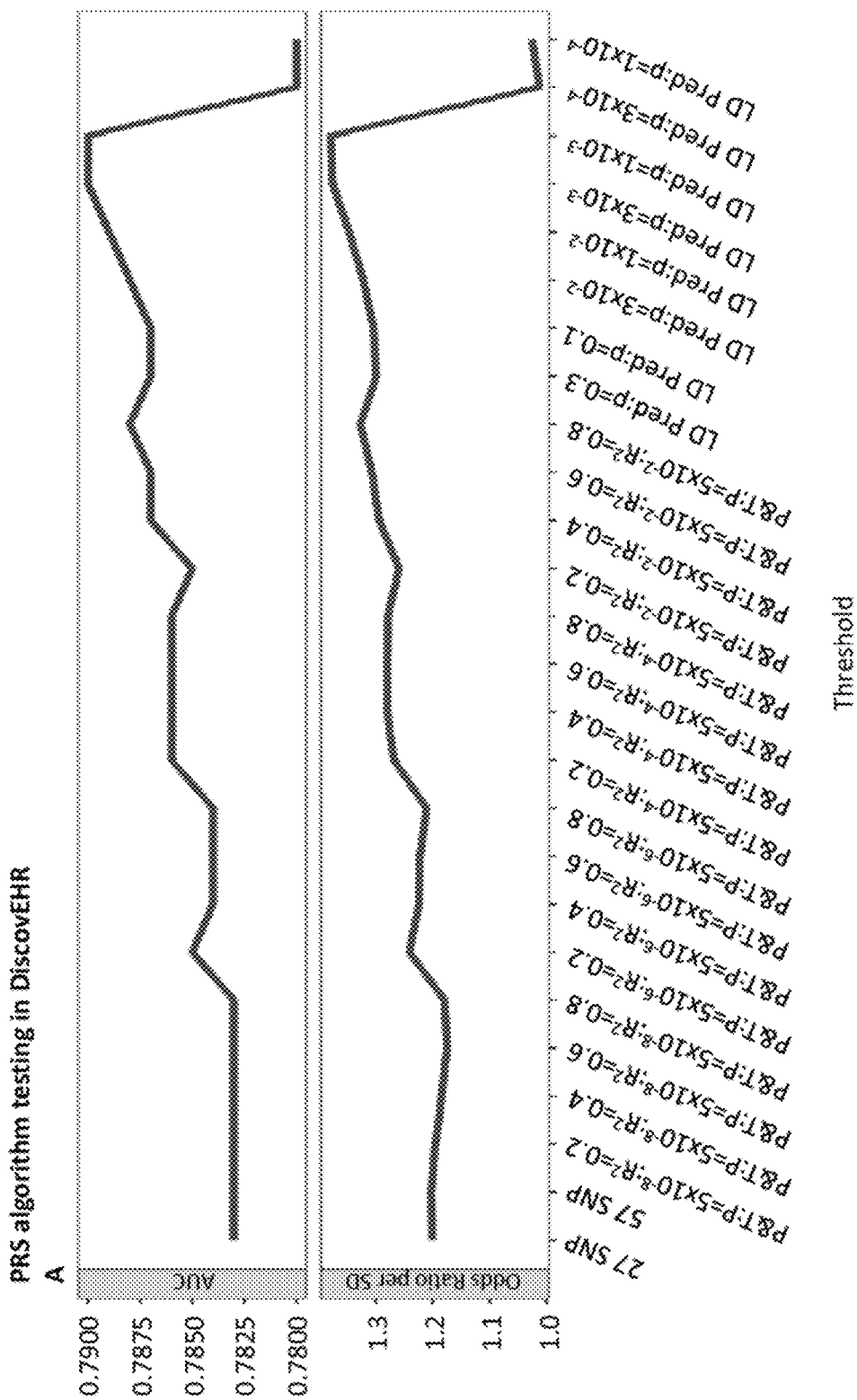
FIG. 10 shows candidate SNP (27-57), pruning and thresholding (P&T), and LDPred results in the DiscovEHR testing data set. Results are shown for the composite endpoint of myocardial infarction, angina, or ischemic stroke. Panel A shows the AUC and odds ratio per SD for each candidate SNP list or set of algorithm tuning parameters. Panel B displays the number of markers used to generate the genetic risk score for each tuning parameter.
Figure 10:
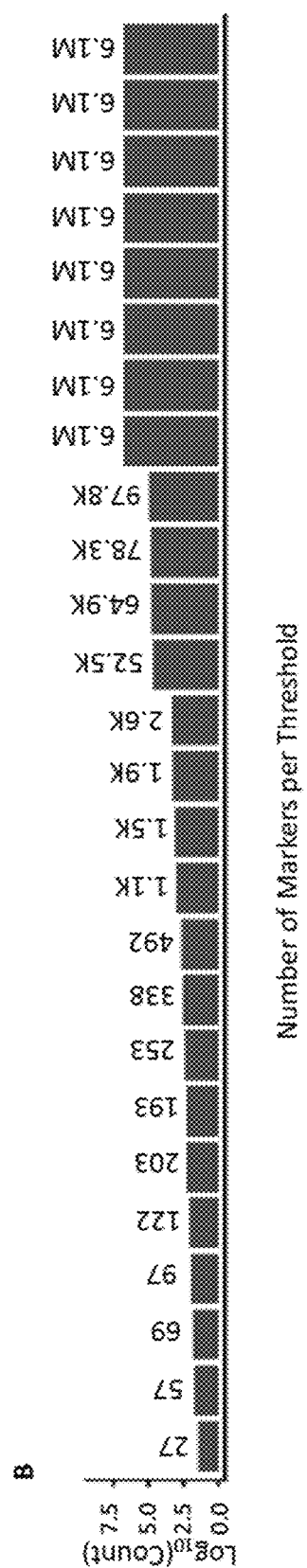
Figure 11:
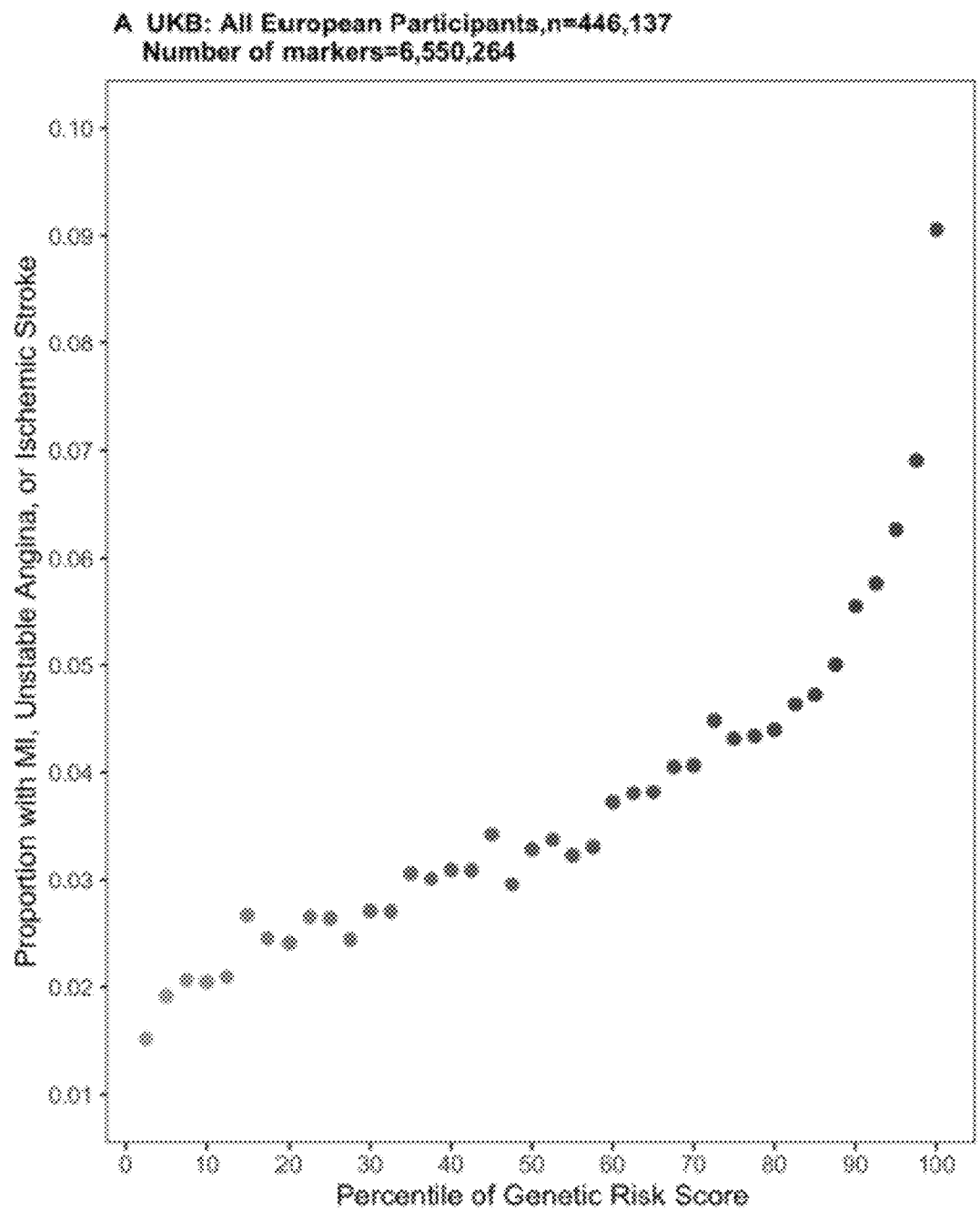
FIG. 11 shows LDPred (p=0.001) results in UKB and DiscovEHR testing data sets. Results shown for the composite endpoint of myocardial infarction, angina, or ischemic stroke. Panel A displays the proportion of participants in UKB with myocardial infarction, angina, or ischemic stroke broken into 2.5% percentiles of the genetic risk score. Panel B displays this proportion in DiscovEHR participants.
Figure 11:
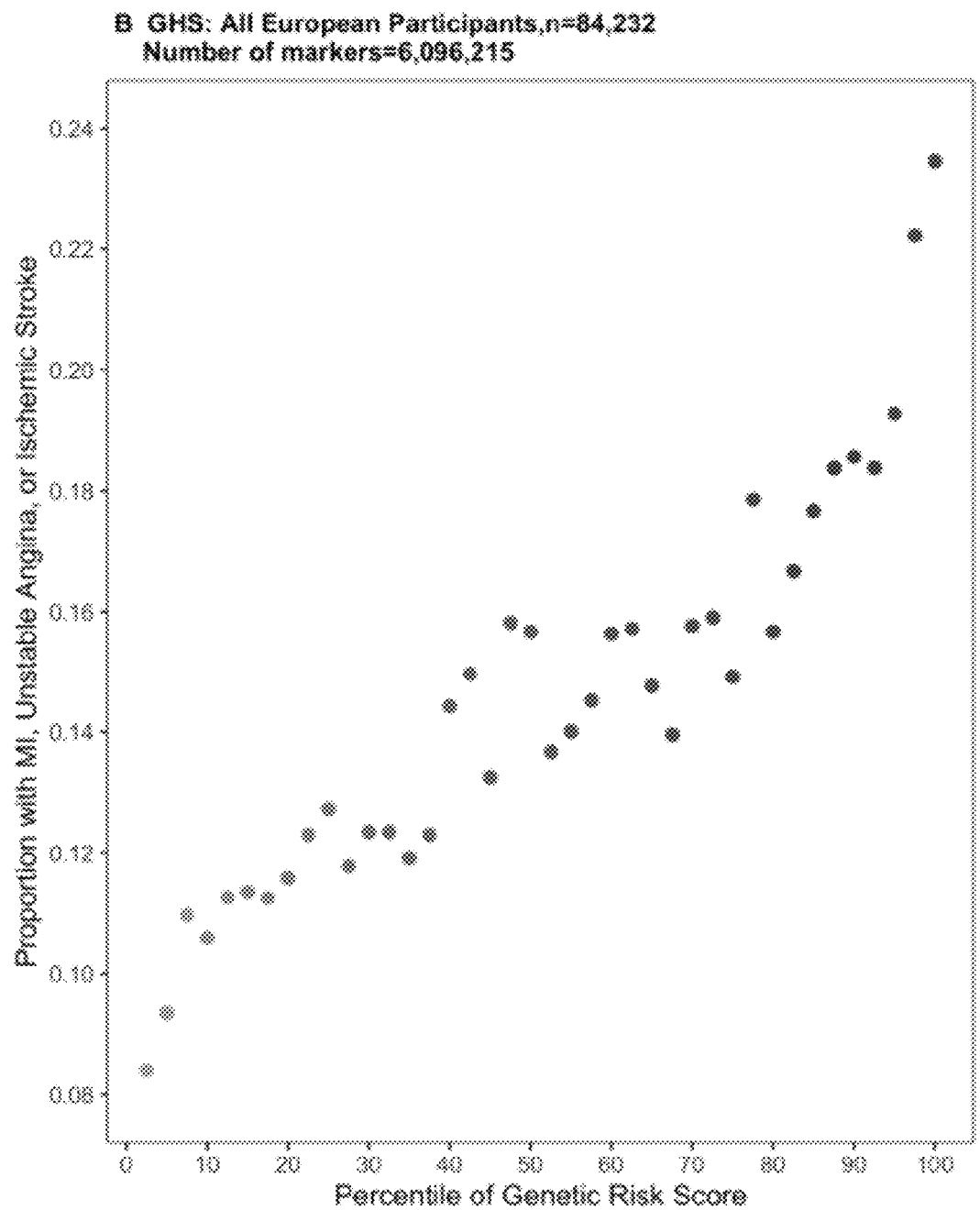

For each set of LDPred or P&T tuning parameter, a PRS was calculated and a logistic regression run with the composite endpoint as the dependent variable and PRS, age, sex, genotyping array (UK Biobank only), and ancestry covariates as independent variables. The odds ratio (OR) per PRS standard deviation (SD) and area under the curve (AUC) were reported for each model. Twenty-eight P&T models (index p-values ranging from $5 \times 10^{-1}$ to $5 \times 10^{-8}$, and $r^2$ values of 0.2, 0.4, 0.6, and 0.8) and eight LDPred models ($\rho=3 \times 10^{-1}$, $1 \times 10^{-1}$, $3 \times 10^{-2}$, $1 \times 10^{-2}$, $3 \times 10^{-3}$, $1 \times 10^{-3}$, $3 \times 10^{-4}$ and $3 \times 10^{-4}$) were tested. In both the UKB and DiscovEHR datasets, LDPred with $\rho=0.001$ demonstrated the best performance and was used in the primary analysis; results are shown in FIGS. 9-11.

Selection of a Threshold for Defining High Risk.

Figure 13:
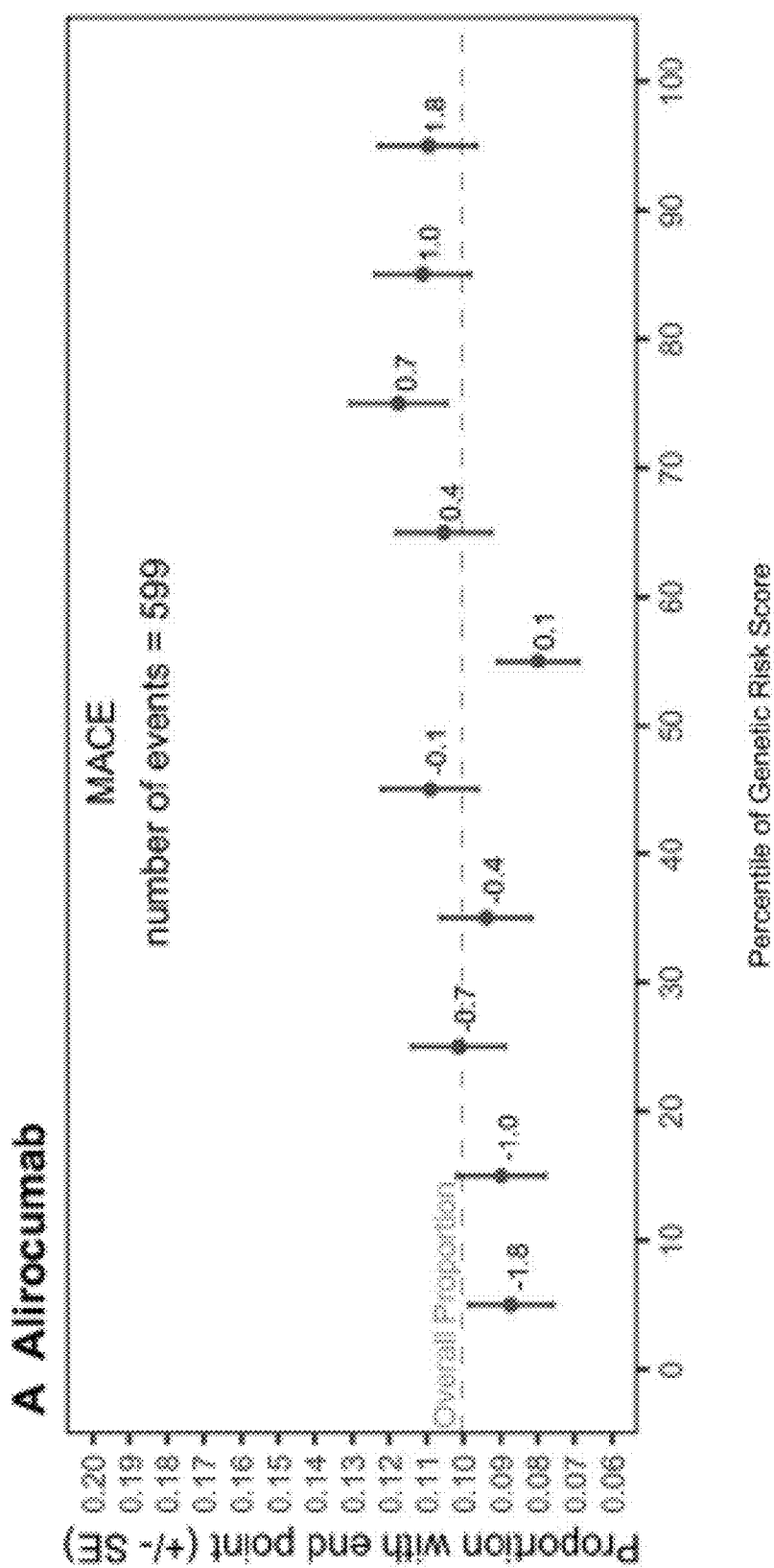
FIG. 13 shows treatment stratified decile plots for MACE, including the end points of death from coronary heart disease, nonfatal myocardial infarction, fatal or nonfatal ischemic stroke, or unstable angina requiring hospitalization. Panel A shows the proportion with an event by genetic risk score decile in the alirocumab arm, while Panel B shows risk by decile in the placebo arm. The mean PRS Z score for each decile is shown to the right of the decile. The gray dashed line represents the overall event proportion by arm.
Figure 13:
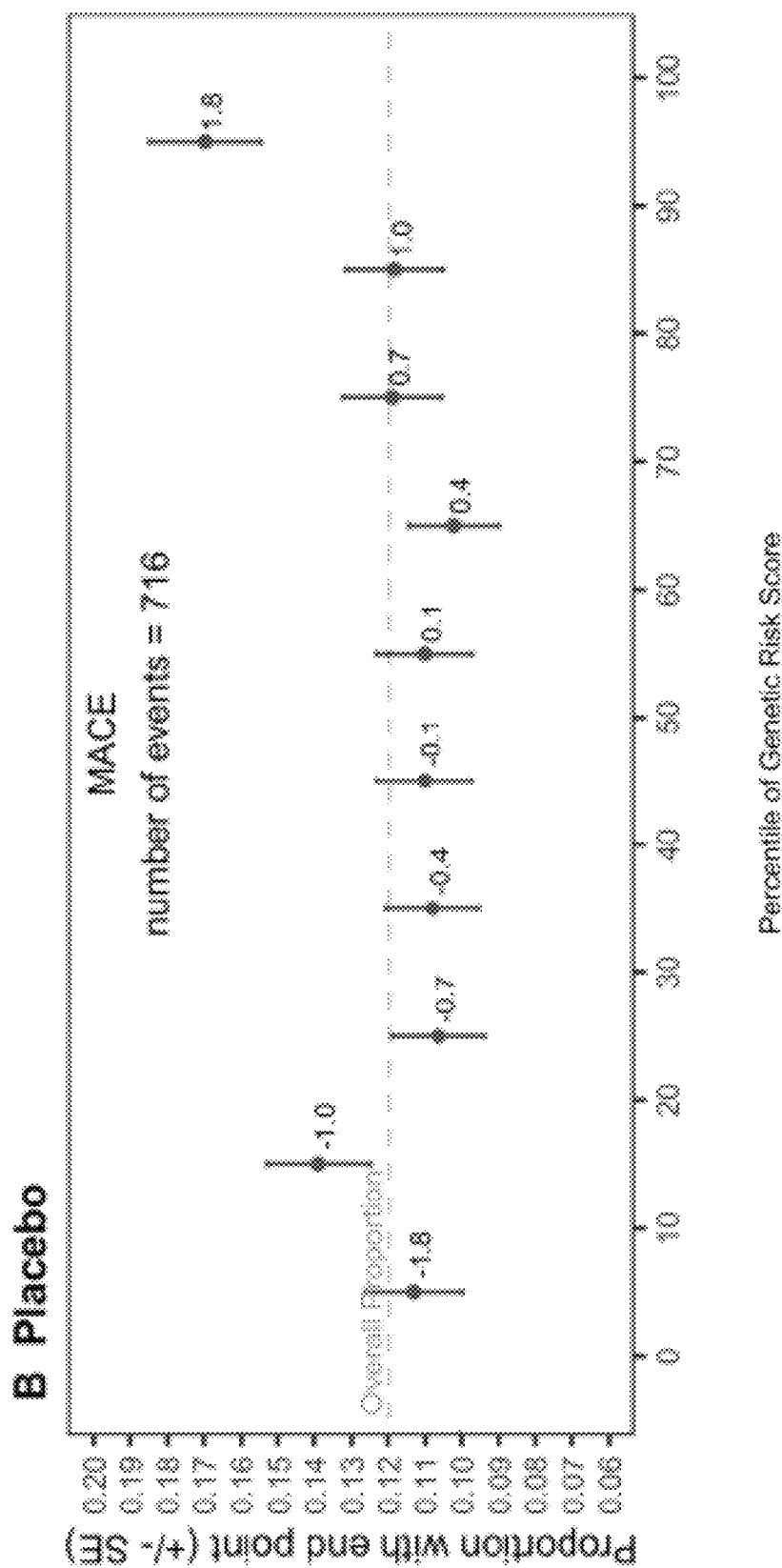
Figure 14:
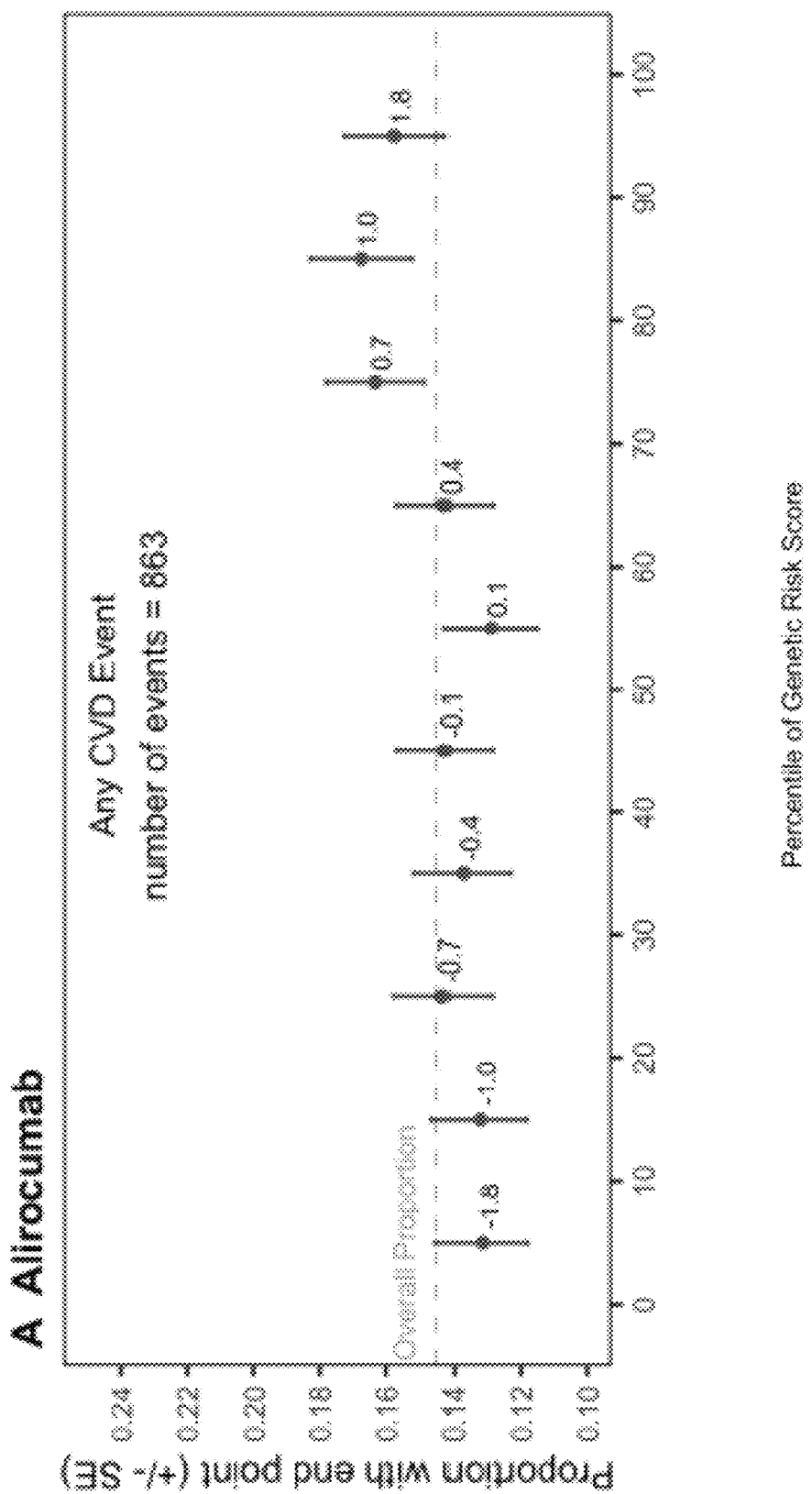
FIG. 14 shows treatment stratified decile plots for secondary end point—any cardiovascular event. This end point includes any death from cardiovascular causes, nonfatal myocardial infarction, or unstable angina requiring hospitalization, an ischemia-driven coronary revascularization procedure, or nonfatal ischemic stroke. Panel A shows the proportion with an event by genetic risk score decile in the alirocumab arm, while Panel B shows risk by decile in the placebo arm. The mean PRS Z score for each decile is shown to the right of the decile. The gray dashed line represents the overall event proportion by arm.
Figure 14:
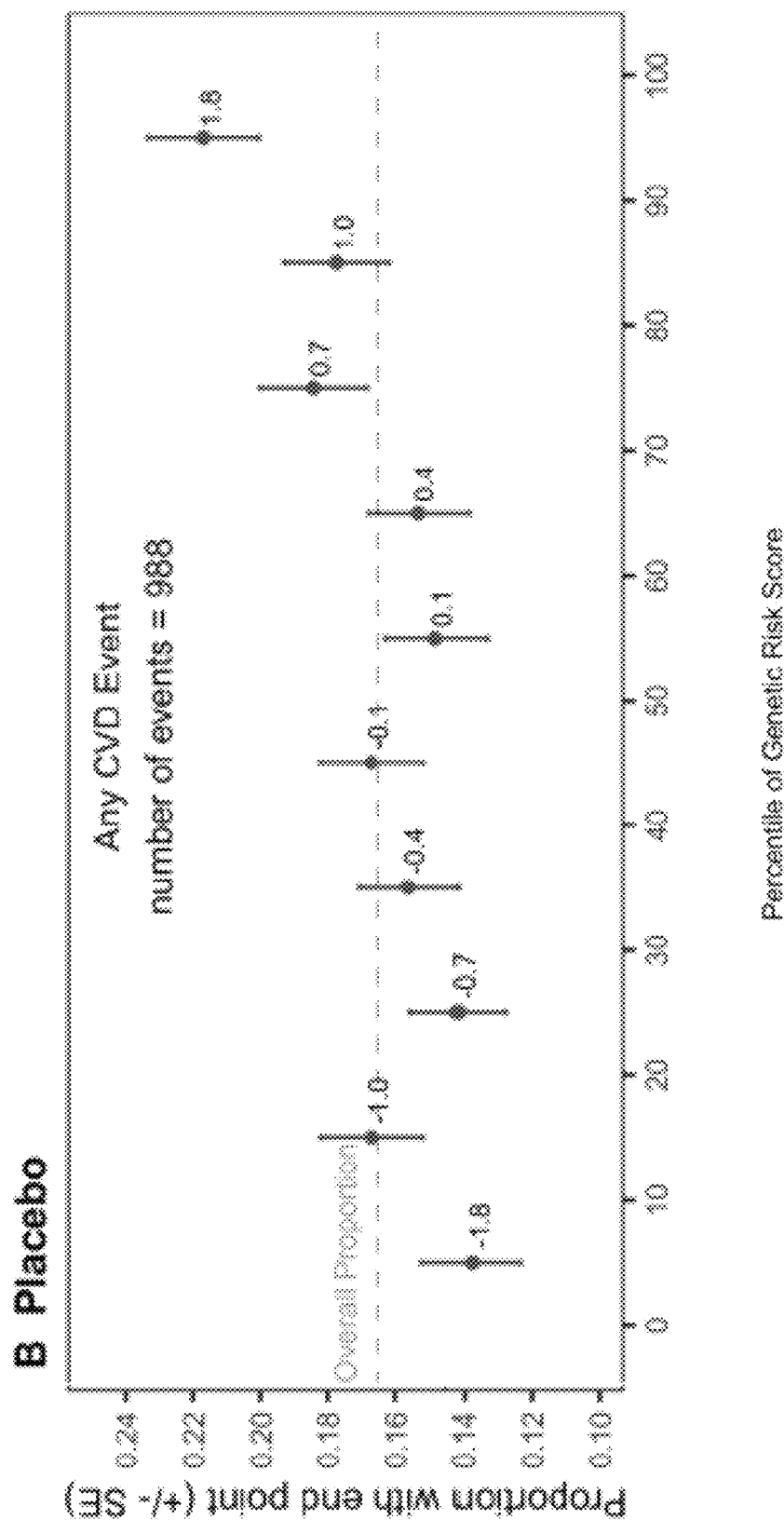
Figure 15:
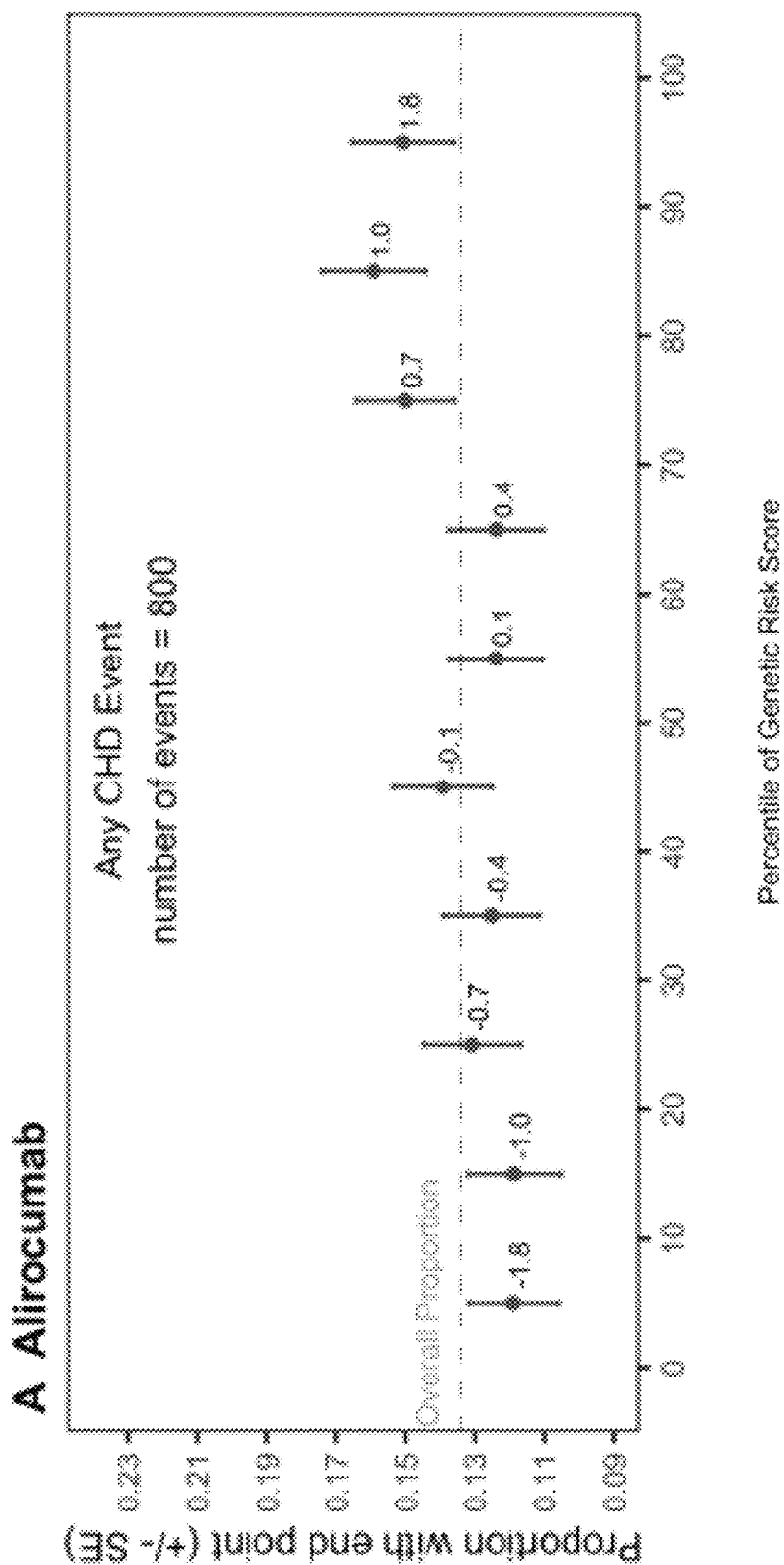
FIG. 15 shows treatment stratified decile plots for secondary end point—any coronary heart disease event. This end point includes death from coronary heart disease, nonfatal myocardial infarction, unstable angina requiring hospitalization, and an ischemia-driven coronary revascularization procedure. Panel A shows the proportion with an event by genetic risk score decile in the alirocumab arm, while Panel B shows risk by decile in the placebo arm. The mean PRS Z score for each decile is shown to the right of the decile. The gray dashed line represents the overall event proportion by arm.
Figure 15:
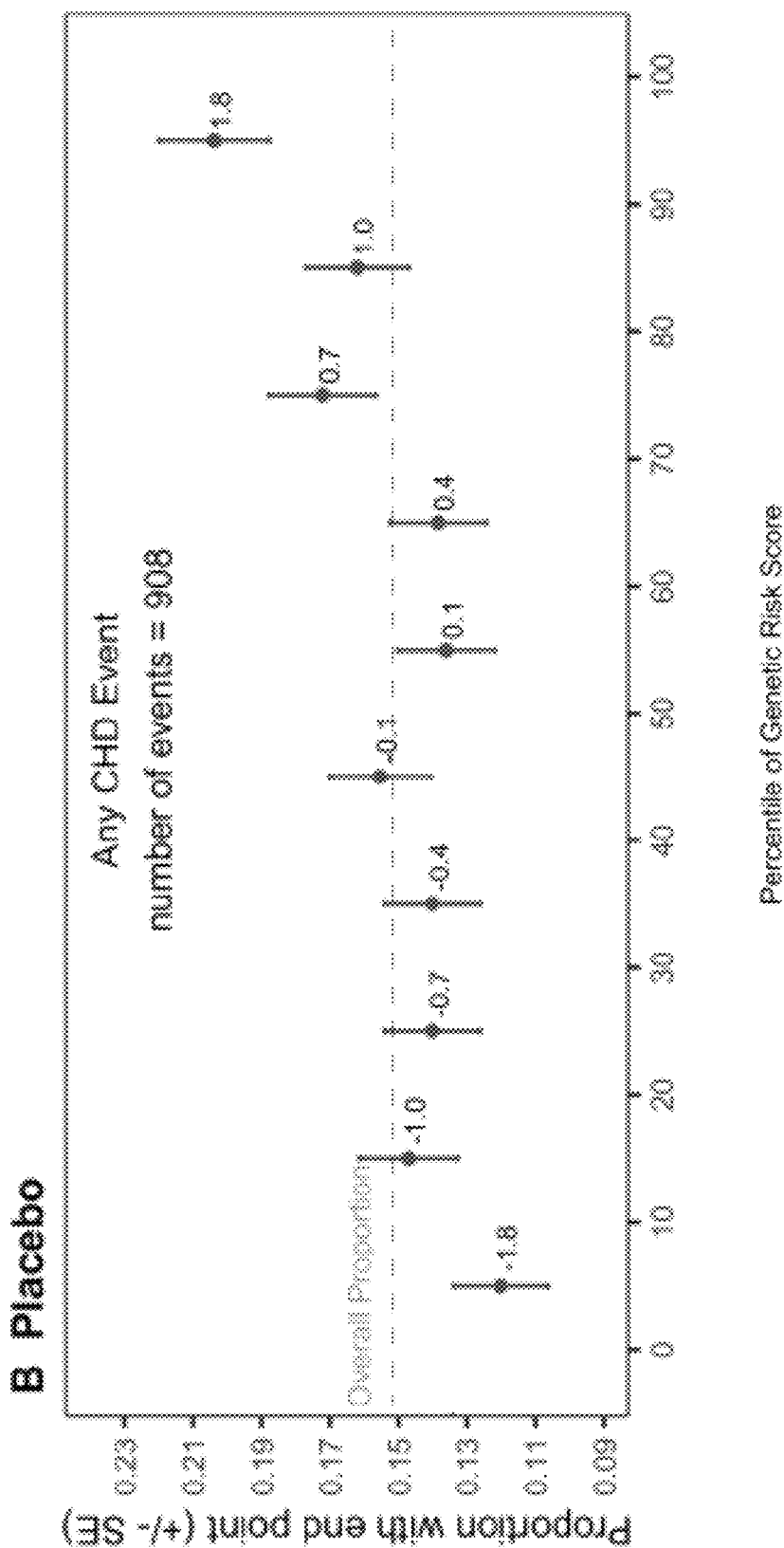
Figure 16:
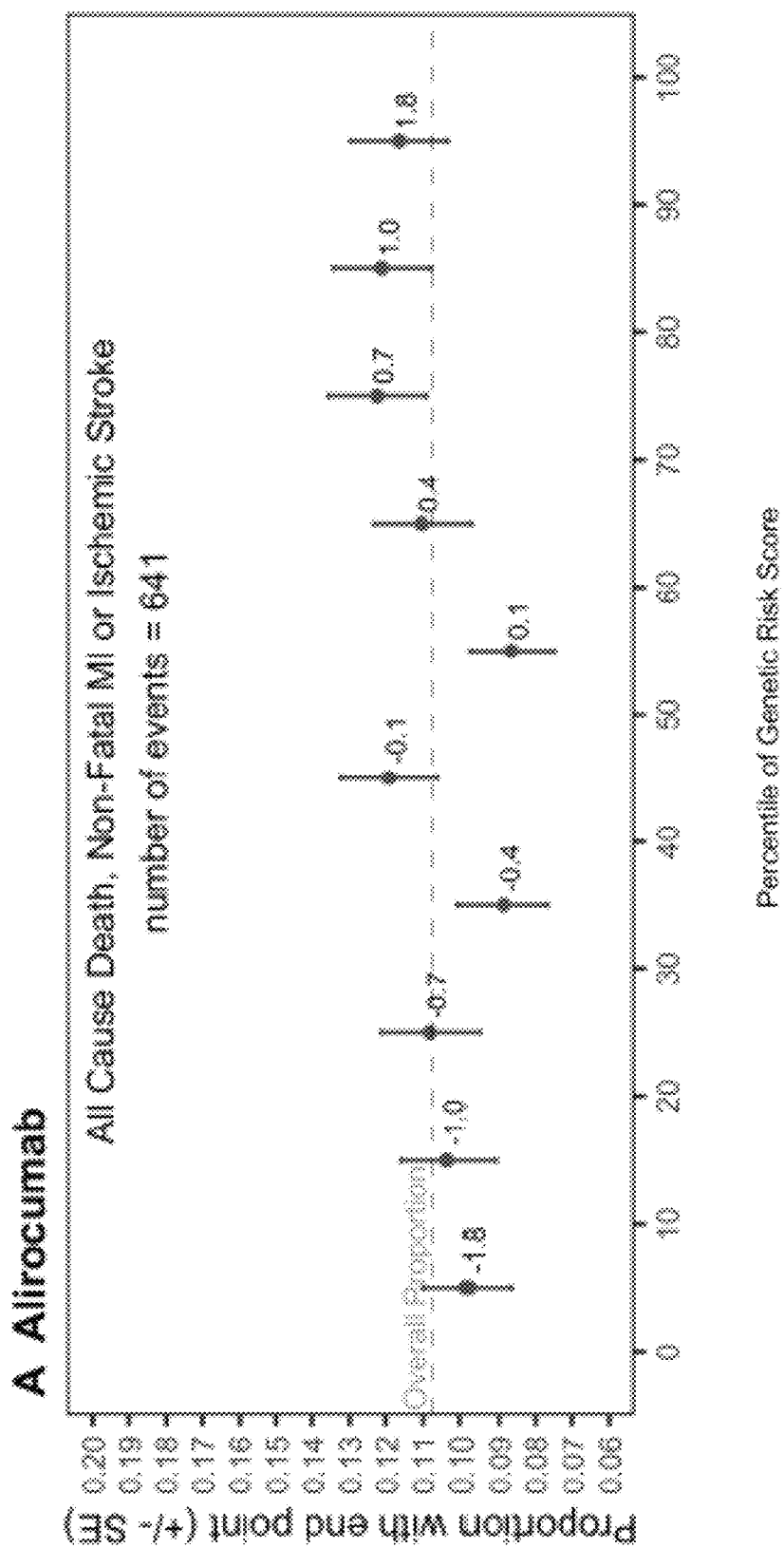
FIG. 16 shows treatment stratified decile plots for secondary end point of death from any cause, nonfatal myocardial infarction, or ischemic stroke. Panel A shows the proportion with an event by genetic risk score decile in the alirocumab arm, while Panel B shows risk by decile in the placebo arm. The mean PRS Z score for each decile is shown to the right of the decile. The gray dashed line represents the overall event proportion by arm.
Figure 16:
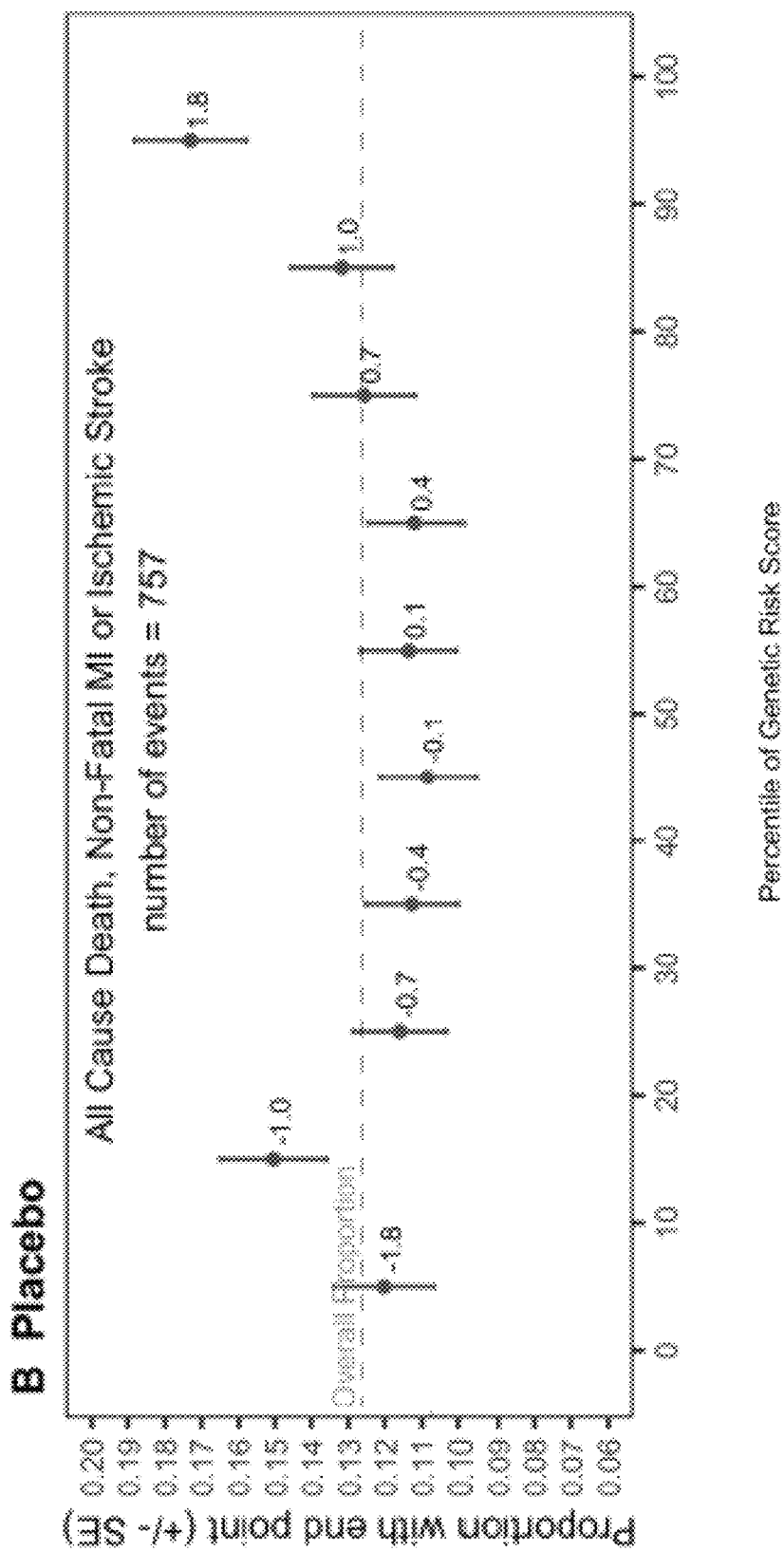
Figure 17:
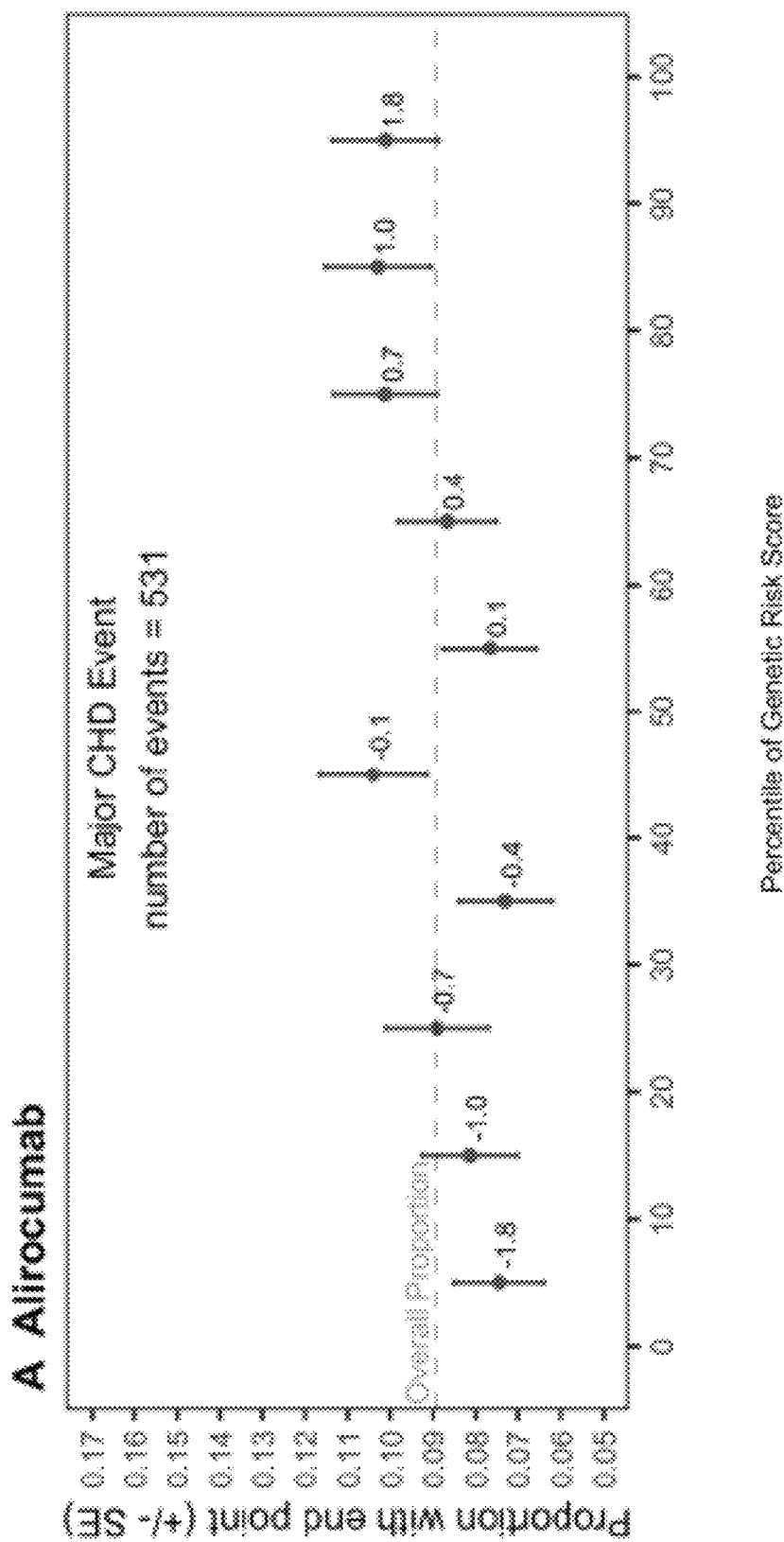
FIG. 17 shows treatment stratified decile plots for secondary end point of major coronary heart disease event. This end point includes death from coronary heart disease and nonfatal myocardial infarction. Panel A shows the proportion with an event by genetic risk score decile in the alirocumab arm, while Panel B shows risk by decile in the placebo arm.
Figure 17:
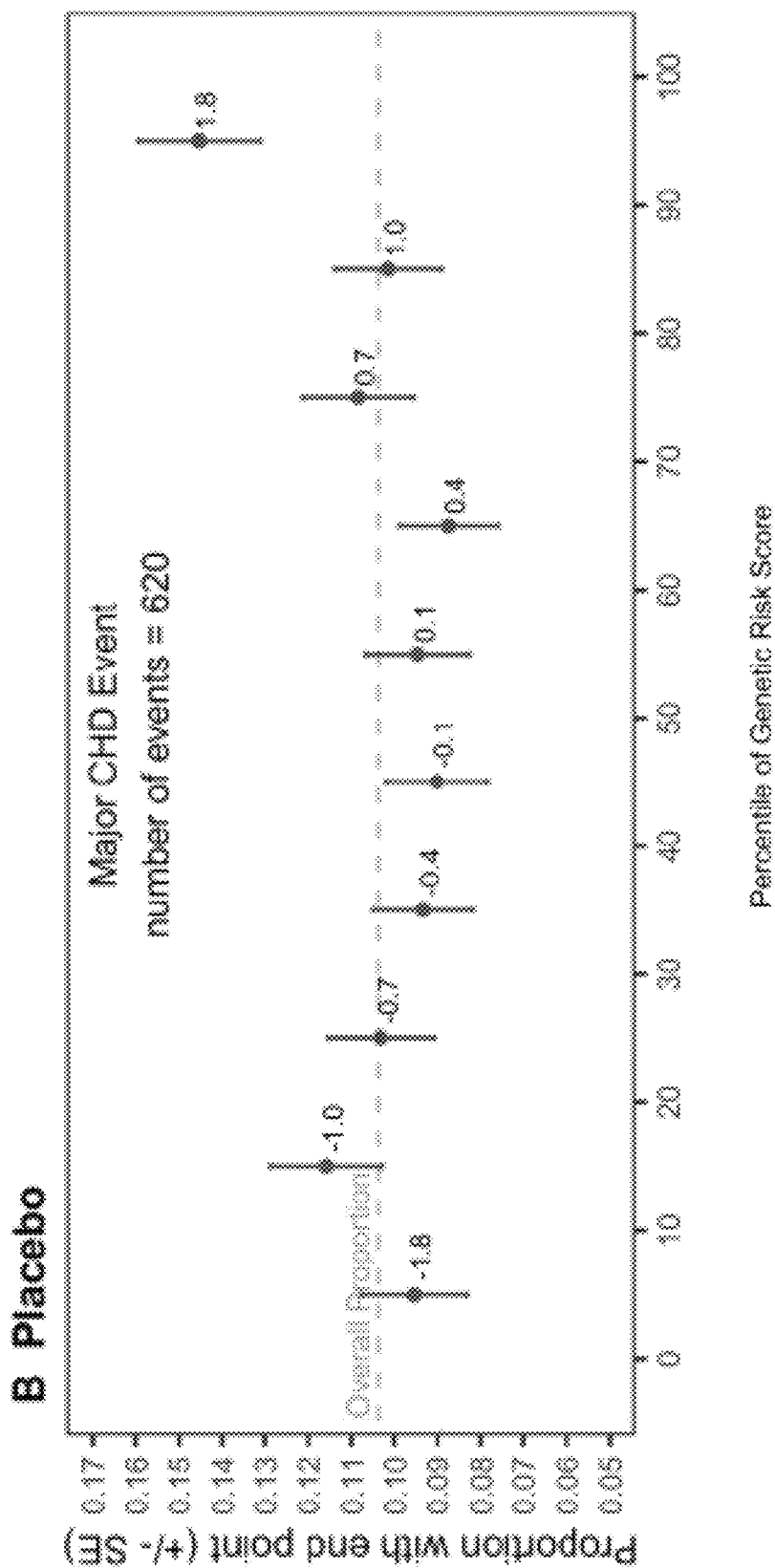
Figure 18:
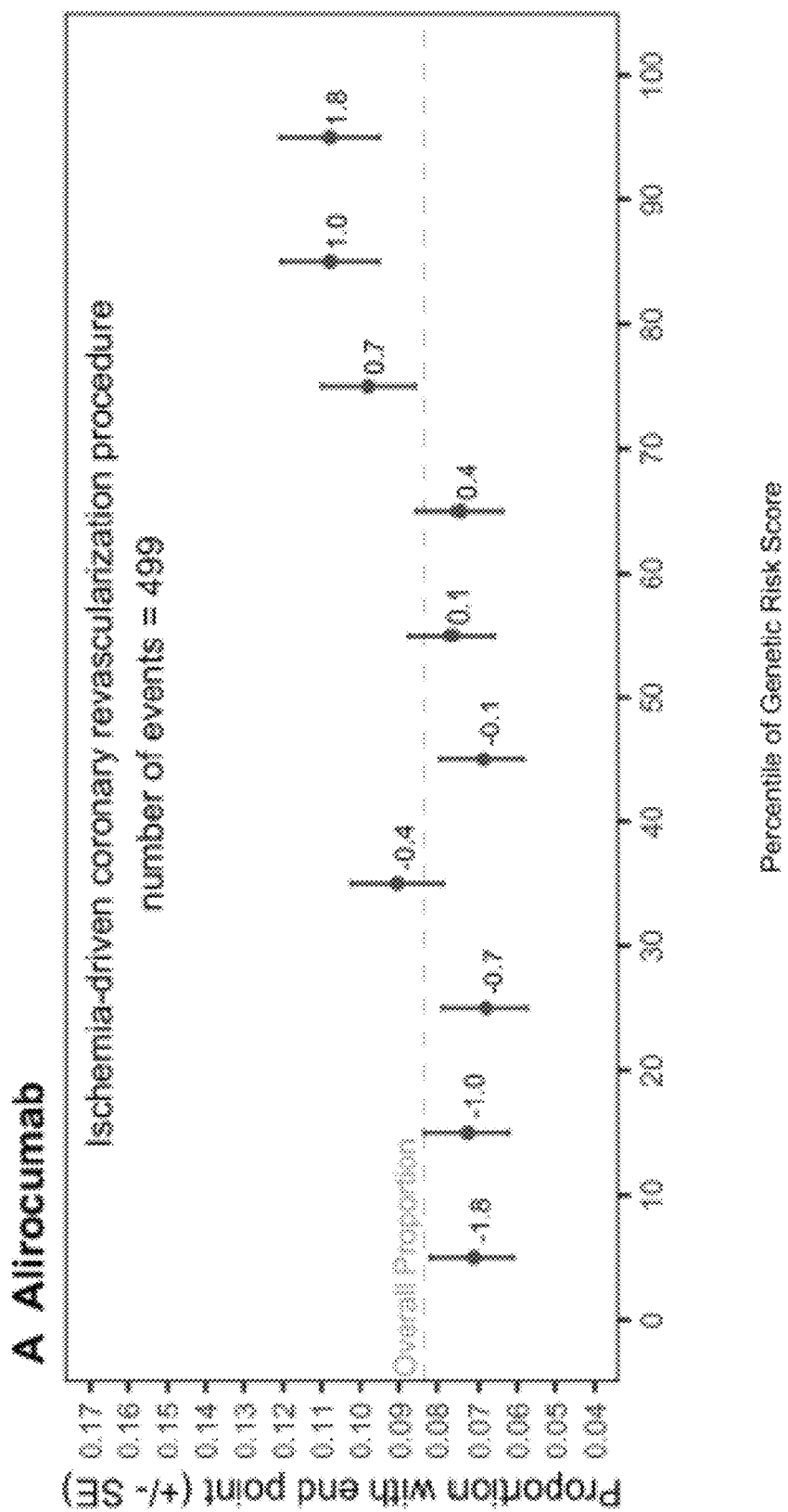
FIG. 18 shows treatment stratified decile plots for secondary end point of Ischemia-driven coronary revascularization procedure. Panel A shows the proportion with an event by genetic risk score decile in the alirocumab arm, while Panel B shows risk by decile in the placebo arm. The mean PRS Z score for each decile is shown to the right of the decile. The gray dashed line represents the overall event proportion by arm.
Figure 18:
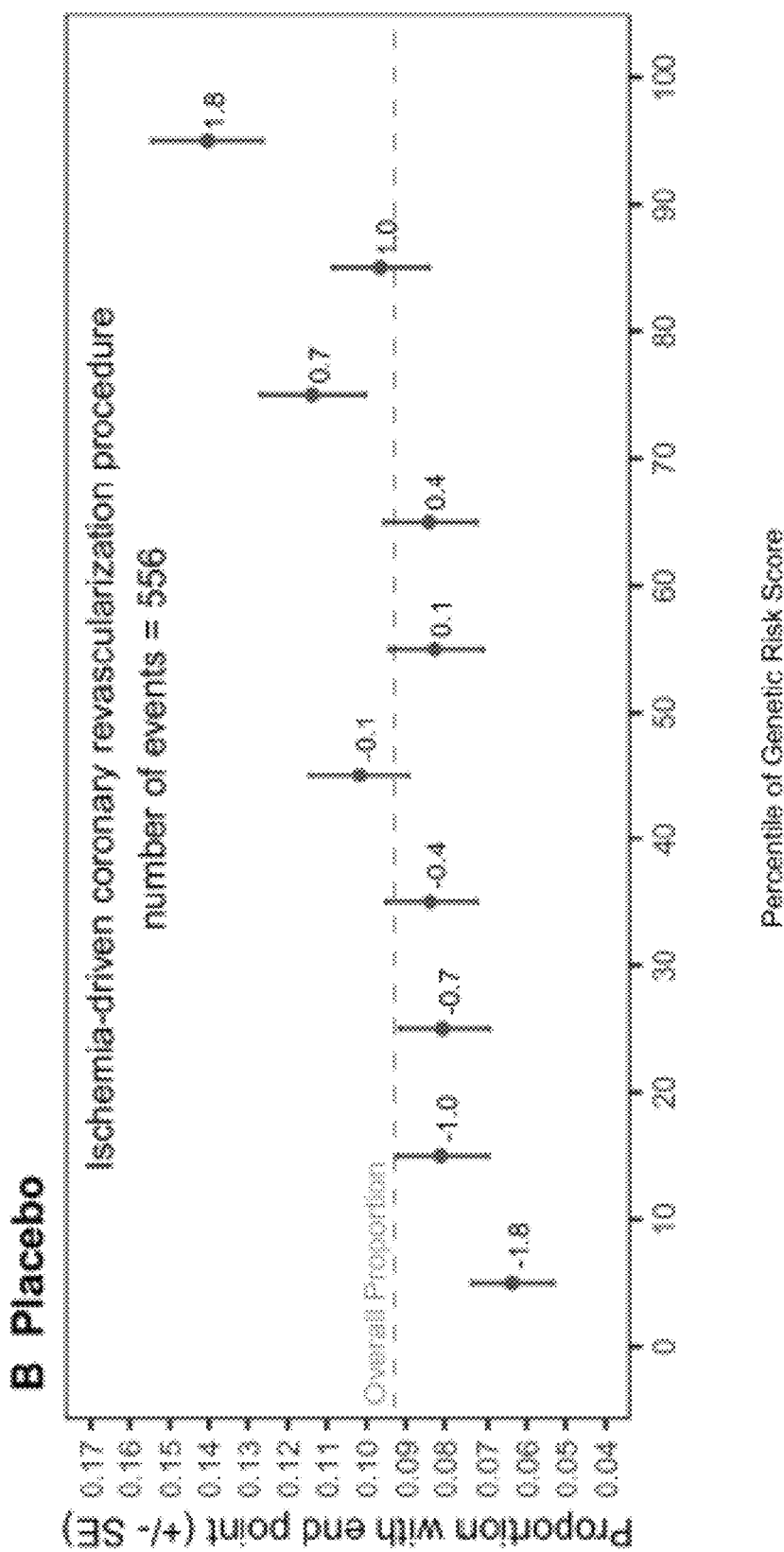

Previous publications of PRS CAD risk have varied in the threshold used to define high risk by PRS, with most thresholds ranging from top tertile to top quintile. Genetic high risk was defined as patients within the top decile of the distribution of the polygenic risk scores. This threshold was selected in a post hoc analysis, which evaluated high genetic risk thresholds ranging from >top 10% to >top 50%, in 10% increments. In the placebo arm, the risk of an event in the top 10% by PRS was consistently higher than the overall event rate and the effect was also consistent across ancestral groups (FIG. 12). While a trend in risk in the placebo arm (specifically, percentiles 70-90) was not observed for the primary endpoint (FIG. 13), these deciles had a greater than average risk across a number of secondary endpoints, including any coronary heart disease (FIG. 15), the end point which most closely aligns with the CAD criteria used in the source dataset. However, though a trend was discernible in some of the secondary endpoints, the only decile with a consistent difference in treatment benefit was the top 10%.

Additional analyses were conducted which indicated that the difference in primary endpoint risk in the top decile differed from all other deciles. Thirty-six genetic risk scores were calculated in ODYSSEY OUTCOMES, across the range of PRS methods and thresholds described above). Using each score, cox models were performed within each treatment arm to evaluate the risk of the primary endpoint in each decile versus all other deciles. Secondly, within each decile, the percent with an event was calculated for each arm, as well as the hazard ratio for treatment difference (risk in alirocumab versus placebo). These results are summarized in FIG. 29, and present the median HR (or percent with an event) per decile, as well as results from the first (Q1) and third (Q3) quartiles. Columns 2 and 3 display results for genetic risk (risk in that decile versus all others), and columns 4-6 focus on within decile differences in risk by treatment.

In these summary estimates, only the top decile showed an elevated risk in the placebo arm and a treatment benefit in excess of the overall study estimate. The genetic risk associated hazard ratio in the placebo arm increased from the $9^{th}$ to the top decile, from 1.03 to 1.24. Conversely, the difference was modest in the alirocumab arm, (1.07 versus 1.09). Results for percent with an event were similar, in the placebo arm the percent in the top decile was >2% higher than any other decile, whereas the risk in top decile in the alirocumab arm was indistinguishable from the other deciles. Due to the differences in risk across the placebo and alirocumab arms in the top decile, the median hazard ratio for treatment difference was 0.70, versus estimates of 0.80-0.89 in all other deciles.

In the top decile, it should be noted that across all 36 genetic risk score generation algorithms, the largest difference in treatment was observed in the genetic score derived from LDPred (rho=0.001). This method was selected a priori from testing in two independent datasets because it demonstrated the best ability to discriminate CAD cases from controls. Across a range of genetic risk score algorithms, with scores comprising fewer than one hundred markers to over six million genetic markers, the effect in the top decile for the placebo group was generally different from the other deciles. The median observed treatment benefit (HR=0.70) in the top genetic decile is of larger magnitude than that observed in patients with elevated LDL-C at baseline in the overall study (HR=0.76). These PRS findings align with a previous analysis of genetic risk scores in statin therapy (n=10,456), where the benefit of statin use did not follow a clear linear trend. While there may be some variability in the magnitude of the treatment effect, the full compendium of results suggests that patients in the high genetic risk group (top 10%) receive greater treatment benefit.

Statistical Analysis

Baseline disease and medical history characteristics were analyzed to assess the distribution of cardiovascular risk factors by genetic risk status, high (>percentile threshold) vs lower (≤percentile threshold). Continuous baseline characteristics were compared using a t-test, and binary or categorical characteristics were tested with a chi-square or Fisher's exact test. Baseline lipids were regressed on age, sex, and ancestry covariates; residuals from the model were transformed with a rank inverse normal transformation (RINT) prior to comparison of genetic risk groups. Change in lipids at 4 months were analyzed similarly, using RINT residuals from a linear regression model adjusting for baseline, age, sex, and ancestry covariates.

In this analysis, MACE and all secondary end points followed the definitions in the ODYSSEY OUTCOMES trial and an intention-to-treat analysis approach. The primary analysis was the time to the first occurrence of any component of the composite primary end point. Evaluation of the relationship between the PRS and MACE or other efficacy endpoints was conducted using two different analysis approaches. First, MACE and secondary endpoint risk was evaluated in placebo treated patients, with Cox proportional hazard models. The PRS was modeled as both a continuous and binary (above/below threshold) covariate. Secondly, treatment efficacy was also evaluated using Cox models, stratified by genetically-defined high and lower risk groups. To determine whether alirocumab treatment benefit differed across genetically-defined risk groups, a non-stratified Cox model with a treatment-by-genetic risk interaction term was also performed. Inverse-variance weighted meta-analyses were also used to combine placebo and alirocumab PRS risk estimates. Unless otherwise stated, all inferential analyses were conducted with adjustment for baseline and clinical covariates, which included ancestry, age, sex, baseline LDL-C, Lp(a), family history of premature coronary heart disease, and the following medical characteristics prior to index ACS that were strongly prognostic for end points in the study and imbalanced across genetically defined risk groups: myocardial infarction; percutaneous coronary intervention; coronary artery bypass grafting; and congestive heart failure. Risk factor-stratified analyses were also conducted, with Lp(a) (≥50 mg/dL vs. <50 mg/dL), LDL-C (≥100 mg/dL vs. <100 mg/dL), Framingham (FHS) recurrent risk score and very high risk (VHR) groups. The FHS and VHR risk algorithms are described herein. With the exception of the VHR analysis, all of these analyses included the covariates noted above (other than the stratification factor, if applicable). As this was an exploratory analysis, p-values <0.05 from the covariate-adjusted Cox models were considered significant.

The Framingham Recurrent Coronary Heart Disease Risk Score.

Scores are based on regression coefficients for up to 4-year risk prediction, based on age, log-transformed ratio of total to HDL cholesterol, diabetes status, systolic blood pressure (women) and smoking status (women). Scores were calculated in all ODYSSEY patients and analyzed as both a continuous measure and stratified by median score (≥median versus <median). The second risk factor analyses classified patients by very high risk (VHR) categories (as described in Roe et al., Circulation, 2019, 140, 1578-1589). VHR were categorized with two sets of criteria. The first criteria (multiple prior ASCSD events) identified patients with a least one prior ischemic event including ischemic stroke, myocardial infarction, or peripheral artery disease. The second set of criteria (major prior ASCVD event+multiple high-risk conditions) identified patients with 1 major ASCVD event (the qualifying index ACS event) and at least 2 high-risk conditions, including diabetes mellitus, current smoking, age ≥65 years, history of hypertension, baseline eGFR of ≥15-<60 mL·min$^{1}$·1.73 m$^{-2}$, congestive heart failure, revascularization prior to index ACS, or LDL-C ≥100 mg/dL with both statin and ezetimibe use.

Example 2: Results

Identification of Patients at Higher Risk of Cardiovascular Events by Polygenic Risk Scores.

The PRS for CAD were first tested and validated for its association with CAD prevalence in two large independent databases with a combined total of >530,000 individuals (DiscovEHR, n=84,243; UK Biobank, n=446,208). From these analyses, the LDPred algorithm (with tuning parameter ρ=0.001), was selected as the optimal PRS generation method, consistent with previous CAD studies (FIGS. 9-11). As a continuous score, the PRS was significantly associated with MACE in DiscovEHR (OR=1.4 per standard deviation (SD) of PRS, p<0.001) and UK Biobank (OR=1.5 per SD of PRS, p<0.001), (FIGS. 9-11). Partitioning analysis was performed and CAD risk was compared across deciles. The observed MACE risk in the highest decile compared to the lower deciles was 1.9 OR and 2.3 OR (p<0.001 for each study) in DiscovEHR and UK Biobank, respectively.

Baseline Characteristics of Study Population and Genetic Risk Groups.

The baseline characteristics of the pharmacogenomic study population were evaluated against the overall study population (FIG. 1). As the pharmacogenomics group is a subset of the overall study population, p-values were not calculated for these comparisons. The genetic study had a smaller percentage of Asian patients than the overall study, largely due to varying pharmacogenomics participation rates by trial enrolment region (FIG. 8). Despite this difference, medical characteristics and lipid profiles at baseline were generally very similar across the overall study and patients in the genetic analysis.

The demographic and baseline characteristics of the high and lower genetic subgroups were also compared to determine if there were any imbalances between the groups. At baseline, patients with high genetic risk (PRS >90%) had a number of significant differences compared to patients with lower genetic risk (PRS ≤90%). Those with high genetic risk were younger (by 1.8 years), had higher incidence of and were more likely to have a prior (to index event) history of myocardial infarction, percutaneous coronary intervention, coronary-artery bypass grafting, congestive heart failure, and family history of premature coronary heart disease. High genetic risk patients had modestly higher baseline concentrations (about 2-5 mg/dL) of total cholesterol, LDL-C, non-HDL cholesterol, and apolipoprotein B. Notably, high genetic risk patients had substantially elevated median Lp(a) levels at baseline (49.4 mg/dL) compared to patients with lower genetic risk (19.9 mg/dL; beta=0.48 standard deviation units, p<0.001). This finding was replicated in the UK Biobank, including 351,224 European individuals with genetic data and Lp(a) levels, where a CAD PRS >90% also associated with higher Lp(a) levels (beta=0.39 standard deviation units, p<0.001). It should be noted that while the association between the genetic risk score and Lp(a) at baseline in this study was highly statistically significant, the proportion of variance in serum Lp(a) levels explained by the PRS is a modest 3.1%. Additional patient characteristics are shown in FIG. 8.

Evaluation of MACE Risk by Genetic Risk Groups.

It was subsequently examined whether the PRS could identify patients at higher risk of cardiovascular events in the post ACS ODYSSEY study patient population. PRS deciles were evaluated for incidence of MACE and each of the secondary endpoints (FIGS. 13-18). In the placebo arm, the risk of an event for any of the endpoints was both consistently higher than the overall event rate and consistent across ancestral groups (FIG. 12). In the placebo arm, high genetic risk patients (defined as the top PRS decile), had approximately 50% higher incidence of MACE (17.0% vs 11.4%, HR=1.59, p<0.001) and 40% higher incidence of the secondary endpoint of any coronary heart disease event (20.4% vs 14.6%, HR=1.55, p<0.001) compared to patients with lower genetic risk (PRS <90%)(FIG. 2). All analyses were adjusted for the covariates previously specified. It should be noted that lower PRS thresholds, >80th and >70th percentiles, also demonstrated statistically significant differences in MACE (p=0.004 and p=0.013, respectively) between high and lower risk in the placebo arm. In a meta-analysis of placebo and alirocumab treatment arms, the combined continuous PRS was p=0.027; the placebo and alirocumab arm p-values were 0.079 and 0.202, respectively.

Comparison of Genetic Risk to Traditional Risk Factors for Cardiovascular Disease.

Figure 3:
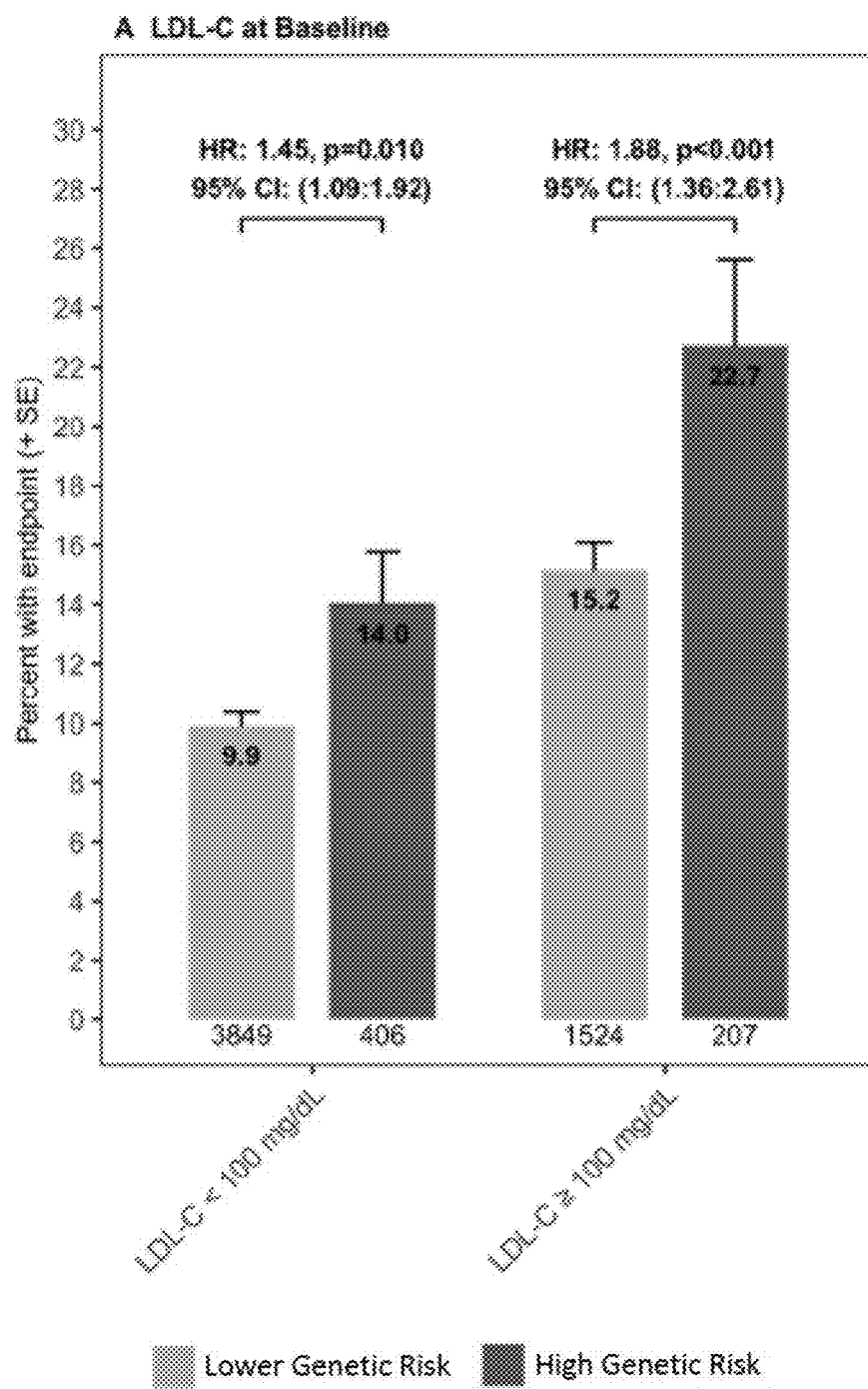
FIG. 3 shows incidence of MACE in the placebo arm in lower genetic risk group (PRS ≤90th percentile) and high genetic risk group (PRS >90th percentile), stratified by risk factors at baseline. Shown is the overall incidence of MACE in patients of all ancestries, stratified by genetic risk for LDL-C at baseline (<100 mg/dL or ≥100 mg/dl) (Panel A); Framingham Recurrent Risk Score (<median or ≥median) (Panel B); and Lp(a) at baseline (<50 mg/dL or ≥50 mg/dl) (Panel C). The numbers at the bottom of each panel are the number of patients in each group and the number inside each bar is the percent with MACE in each group. The hazard ratios and p-values were calculated from a cox proportional hazards model, which was adjusted for ancestry, baseline LDL-C, Lp(a), age, sex, family history of premature coronary heart disease, and the following medical characteristics prior to index ACS: myocardial infarction; percutaneous coronary intervention; coronary artery bypass grafting; and congestive heart failure.
Figure 3:
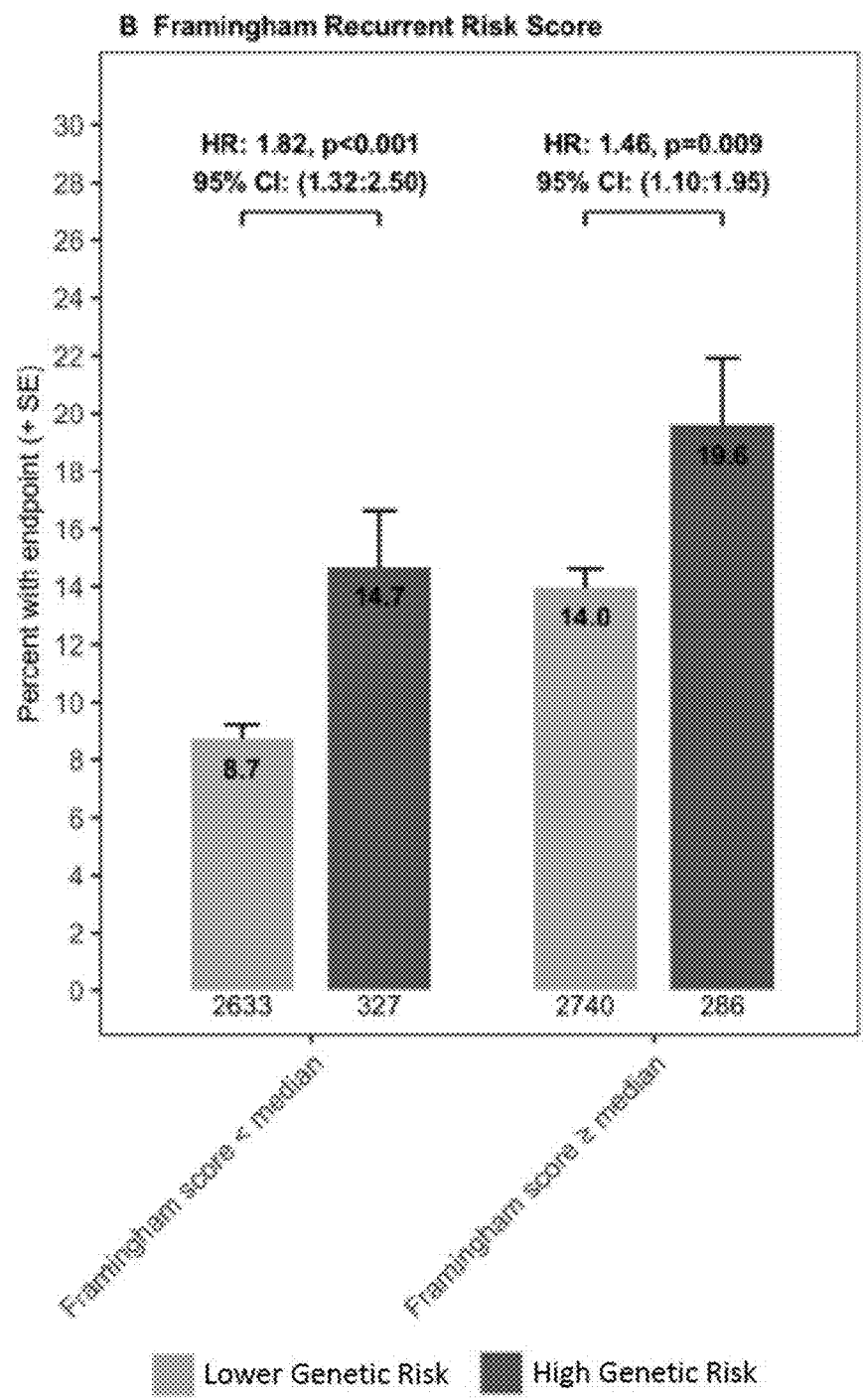
Figure 3:
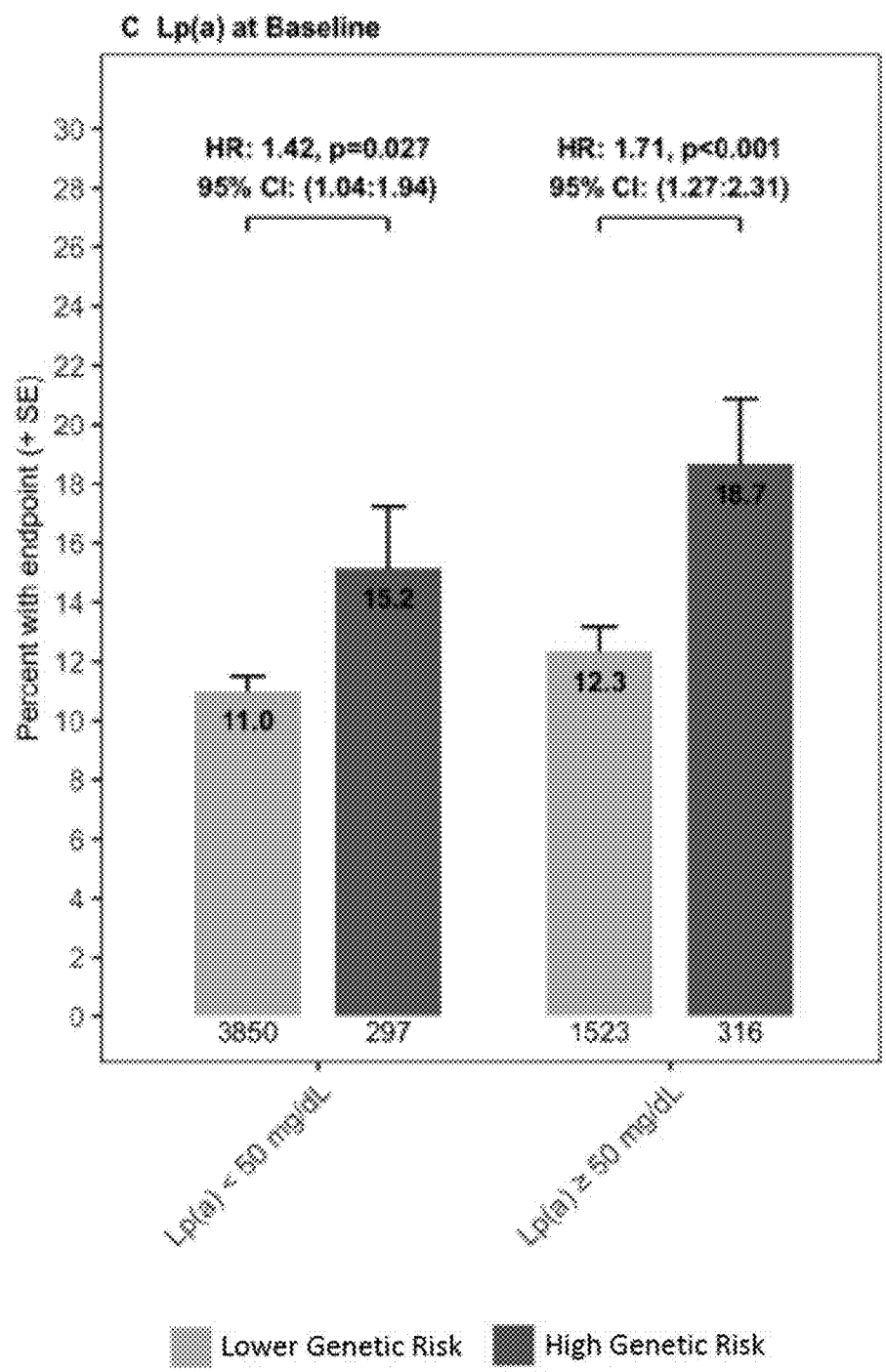

In addition to adjusting for the baseline clinical characteristics and risk factors noted previously, the effects of these risk factors (LDL-C, Lp(a), and other traditional risk factors) on the PRS in placebo treated patients were further evaluated by conducting risk stratified analyses. A stratified analysis of LDL-C (dichotomized at 100 mg/dL) indicated that the PRS is independent of baseline LDL-C levels (FIG. 3A). Patients with both high baseline LDL-C (≥100 mg/dL) and high PRS had the highest incidence of MACE at 22.7%, 95% CI (17.0-28.4), while patients with both lower baseline LDL-C and lower genetic risk had the lowest incidence at 9.9%, 95% CI (9.0-10.8). The use of both high baseline LDL-C and high PRS identifies patients at even higher risk of MACE than either risk factor alone (FIG. 3A).

Figure 19:
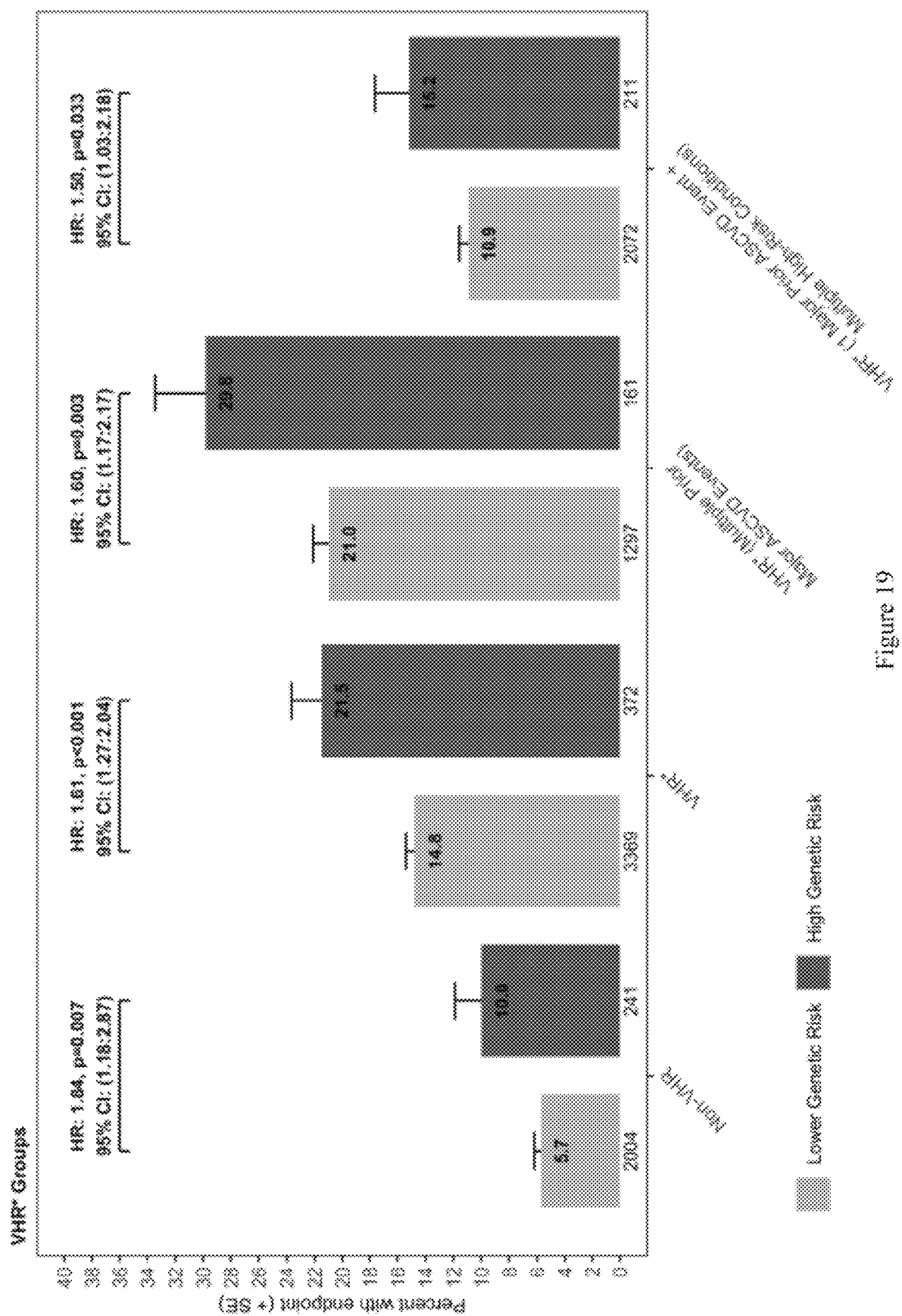
FIG. 19 shows Incidence of MACE in the placebo arm in lower genetic risk group (PRS ≤90th percentile) and high genetic risk group (PRS >90th percentile), stratified by Very High Risk (VHR) groups. Shown is the overall incidence of MACE in patients of all ancestries, stratified by VHR categories. VHR categories follow definitions described in doi: 10.1161/CIRCULATIONAHA.119.042551. VHR* (multiple prior major ASCVD events) includes patients with ≤1 prior ischemic event before the qualifying index ACS event, including ischemic stroke, myocardial infarction, or peripheral artery disease. VHR* (major prior ASCVD event+multiple high-risk conditions) includes patients with 1 major ASCVD event (the qualifying index ACS event) and high-risk conditions (diabetes mellitus, current smoking, age ≤65 years, history of hypertension, baseline eGFR of ≥15-<60 mL·min1·1.73 m−2, congestive heart failure, revascularization prior to index ACS, or LDL-C ≥100 mg/dL with both statin and ezetimibe use). VHR* is the combination of both categories, and non-VHR includes patients without any of these risk factors. The numbers at the bottom of each panel are the number of patients in each group and the number inside each bar is the percent with MACE in each group. The hazard ratios and p-values were calculated from a Cox proportional hazards model, which was adjusted for ancestry. As the composite VHR* risk groups comprise multiple risk factors, covariate adjustment for additional risk factors was not included in this model.

These analyses were extended to a broader set of traditional risk factors (age, systolic blood pressure, smoking status, lipid levels, and type 2 diabetes) established in the Framingham Heart Study (FHS) for recurrent coronary heart disease. The continuous PRS was associated with MACE even after adjustment for baseline FHS risk score, p=0.003 (adjusted for age, sex, ancestry, and the FHS score). The dichotomous PRS also showed consistent effects across FHS stratified by median score, demonstrating the independent and additive value of these measures (FIG. 3B). The PRS was also evaluated in by very high risk (VHR) category and demonstrated consistent effects across risk groups. High genetic risk was still associated with increased MACE risk in the absence of any VHR criteria (non-VHR), HR=1.84 (p=0.007), as described in FIG. 19. The impact of Lp(a) in the association of PRS with risk of MACE was then explored. Lp(a) risk at 50 mg/dL was dichotomized, and performed a combinatorial subgroup analysis with PRS that once again demonstrated the additive value of Lp(a) and PRS (FIG. 3C).

Figure 20:
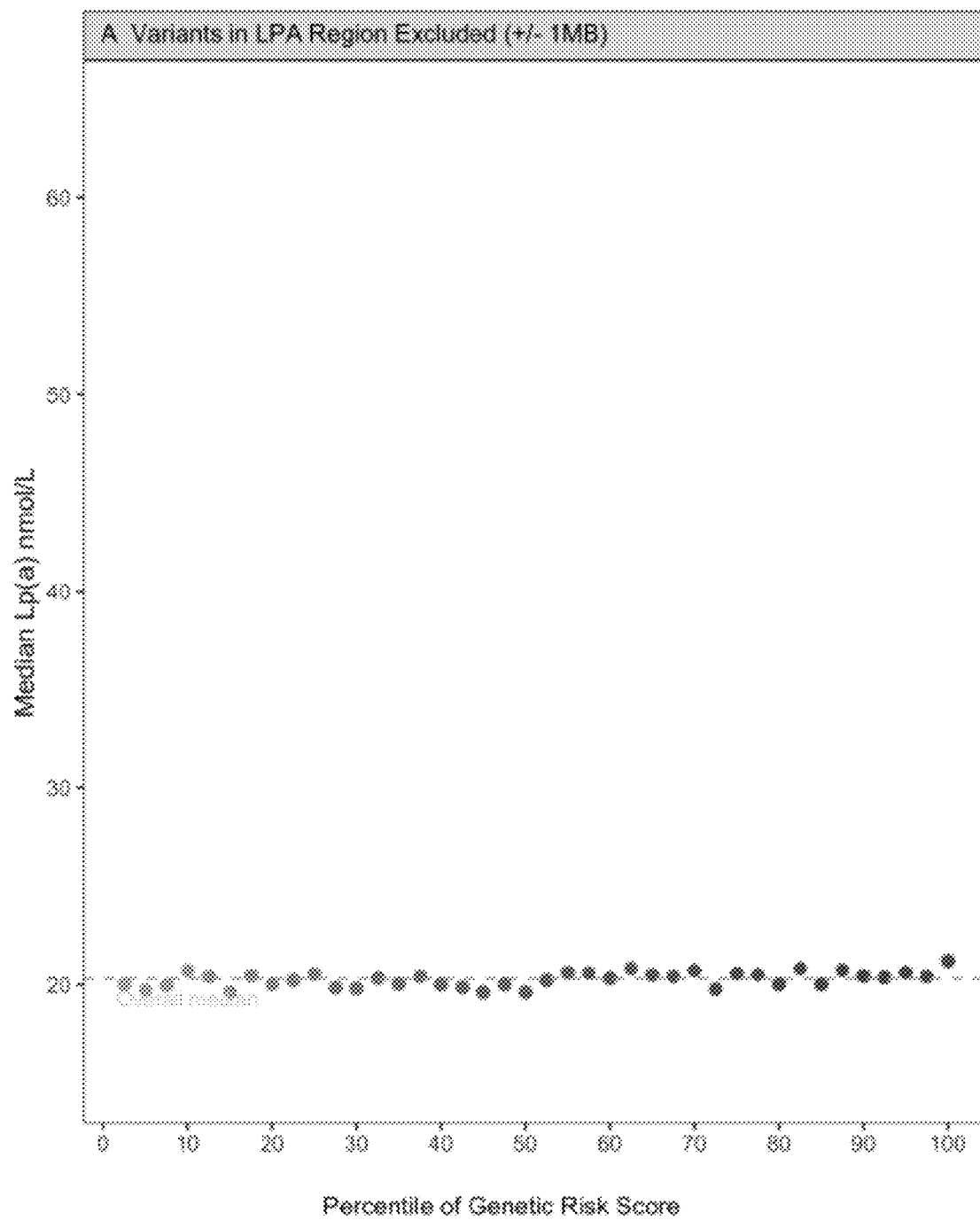
FIG. 20 shows UKB: Median Lp(a) nmol/L, excluding/including LPA gene region. Results shown for the median Lp(a) by percentile, excluding and including the LPA gene region (+/−1 MB) in the score. Panel A displays the genome-wide PRS with the LPA gene region (+/−1 MB) excluded; and Panel B displays the genome-wide score.
Figure 20:
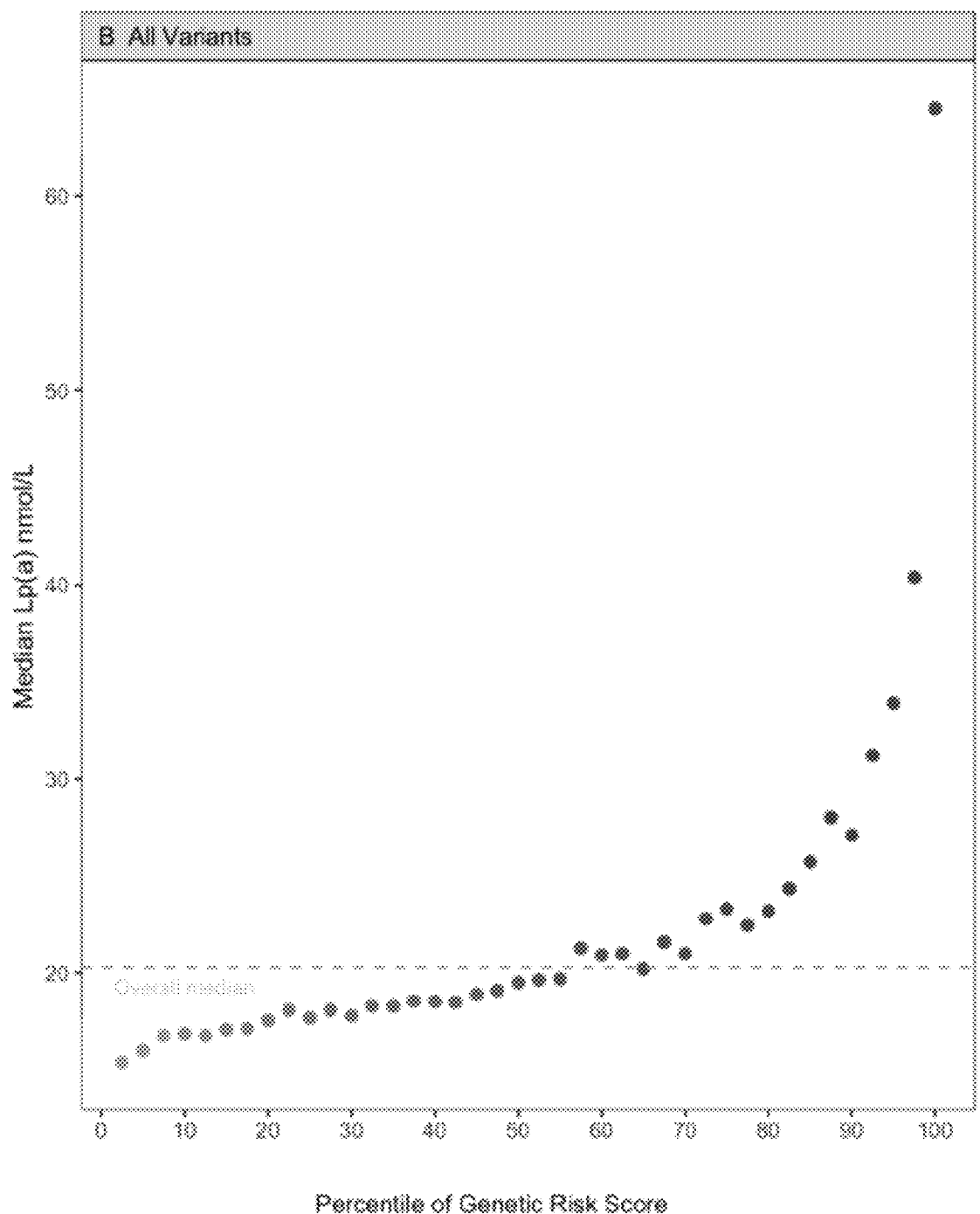
Figure 21:
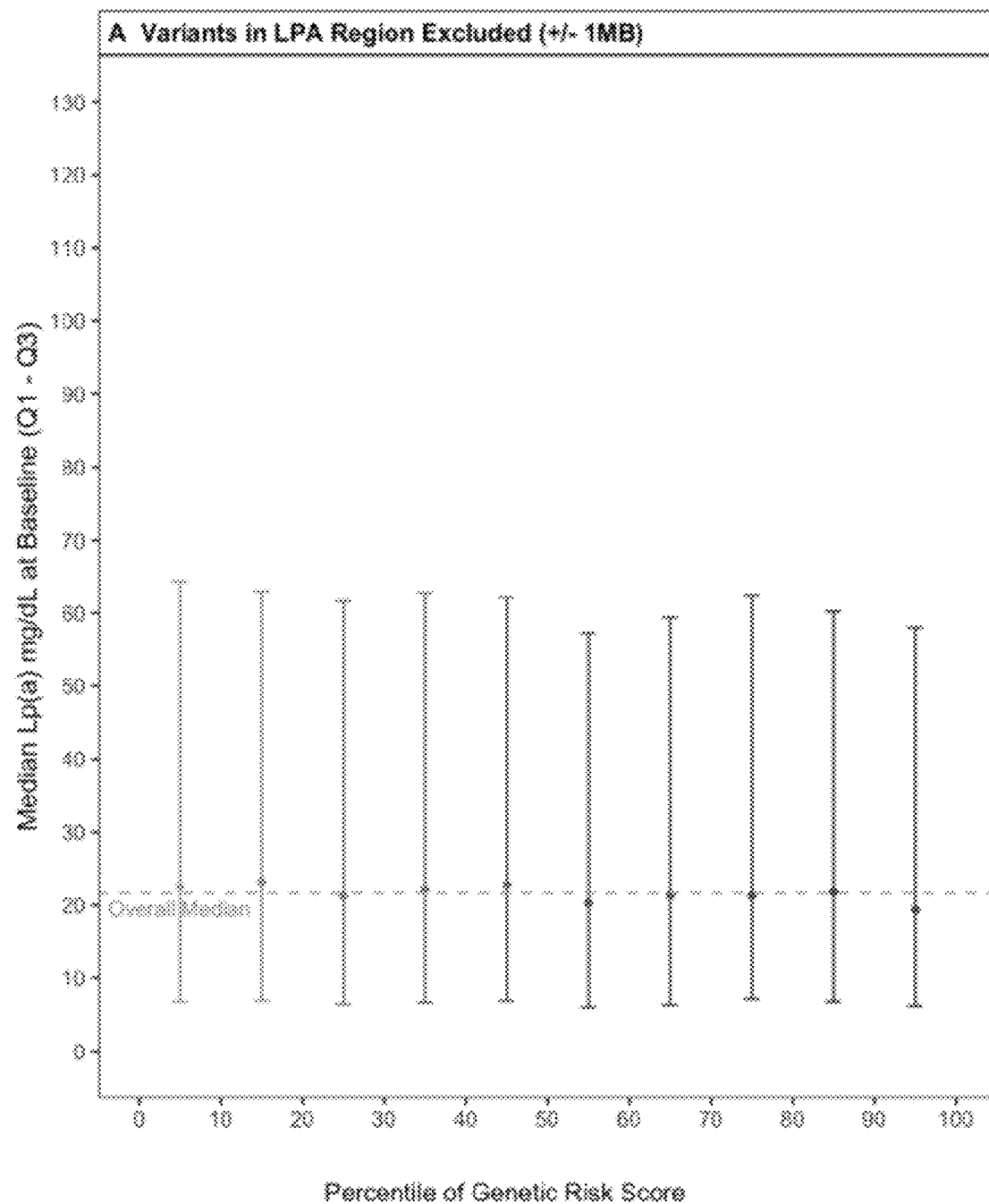
FIG. 21 shows ODYSSEY: Median Lp(a) mg/dL (Q1-Q3), excluding/including LPA gene region. Results shown for the median Lp(a) by percentile, excluding and including the LPA gene region (+/−1 MB) in the score. Panel A displays the genome-wide PRS with the LPA gene region (+/−1 MB) excluded; and Panel B displays the genome-wide score.
Figure 21:
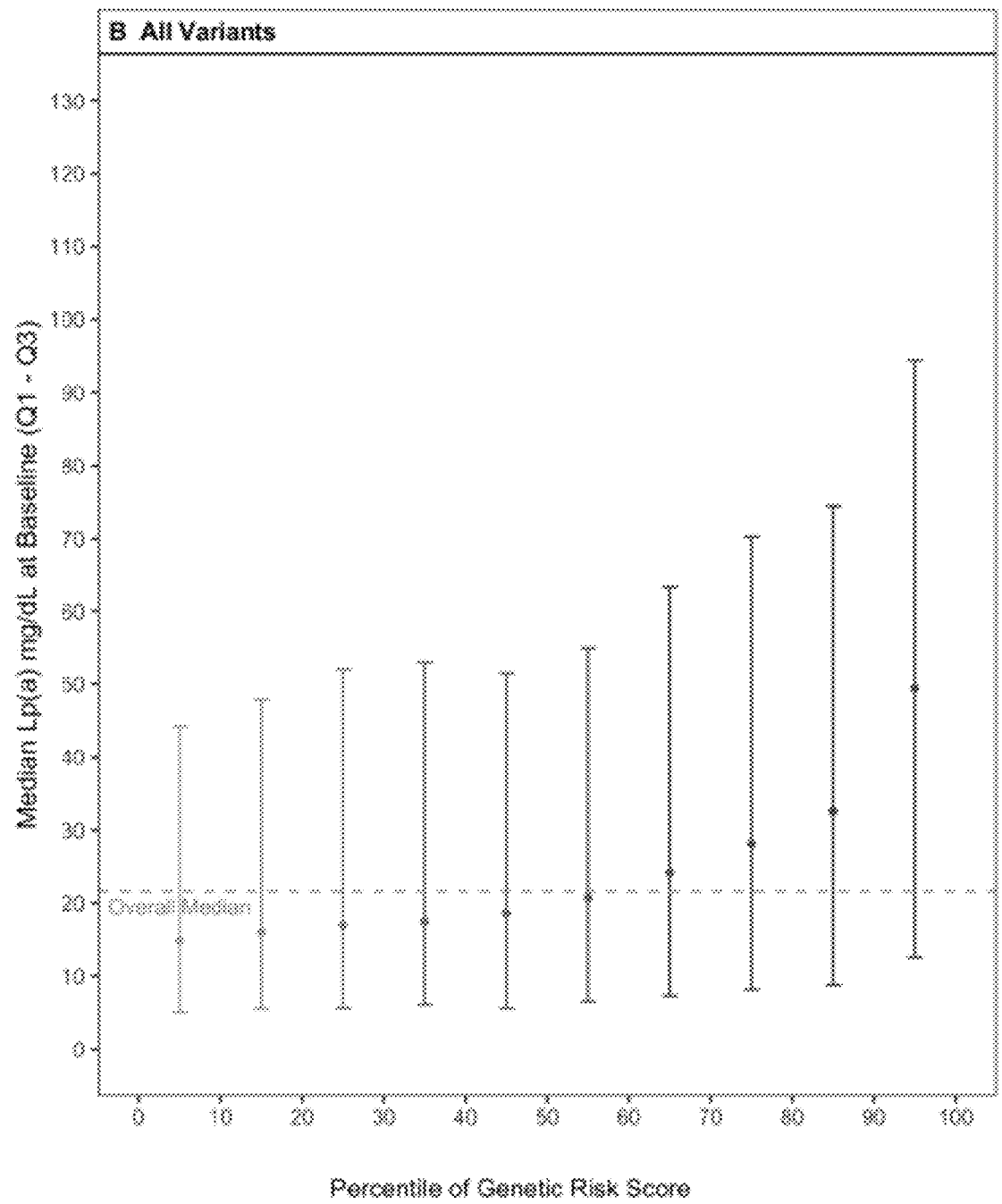

Due to the strong association between baseline Lp(a) and the PRS, the relationship between the PRS and Lp(a) levels was further explored. Variants in and around the LPA gene (+/−1 MB) were removed from the PRS. This modified PRS was evaluated for the effects on Lp(a) levels and risk of MACE in ODYSSEY and UK Biobank. Removal of these variants (+/−1 MB) attenuated the PRS association with Lp(a) levels, the proportion of variability explained in Lp(a) by the modified PRS was approximately zero in both studies, (FIGS. 20-21).

Figure 22:
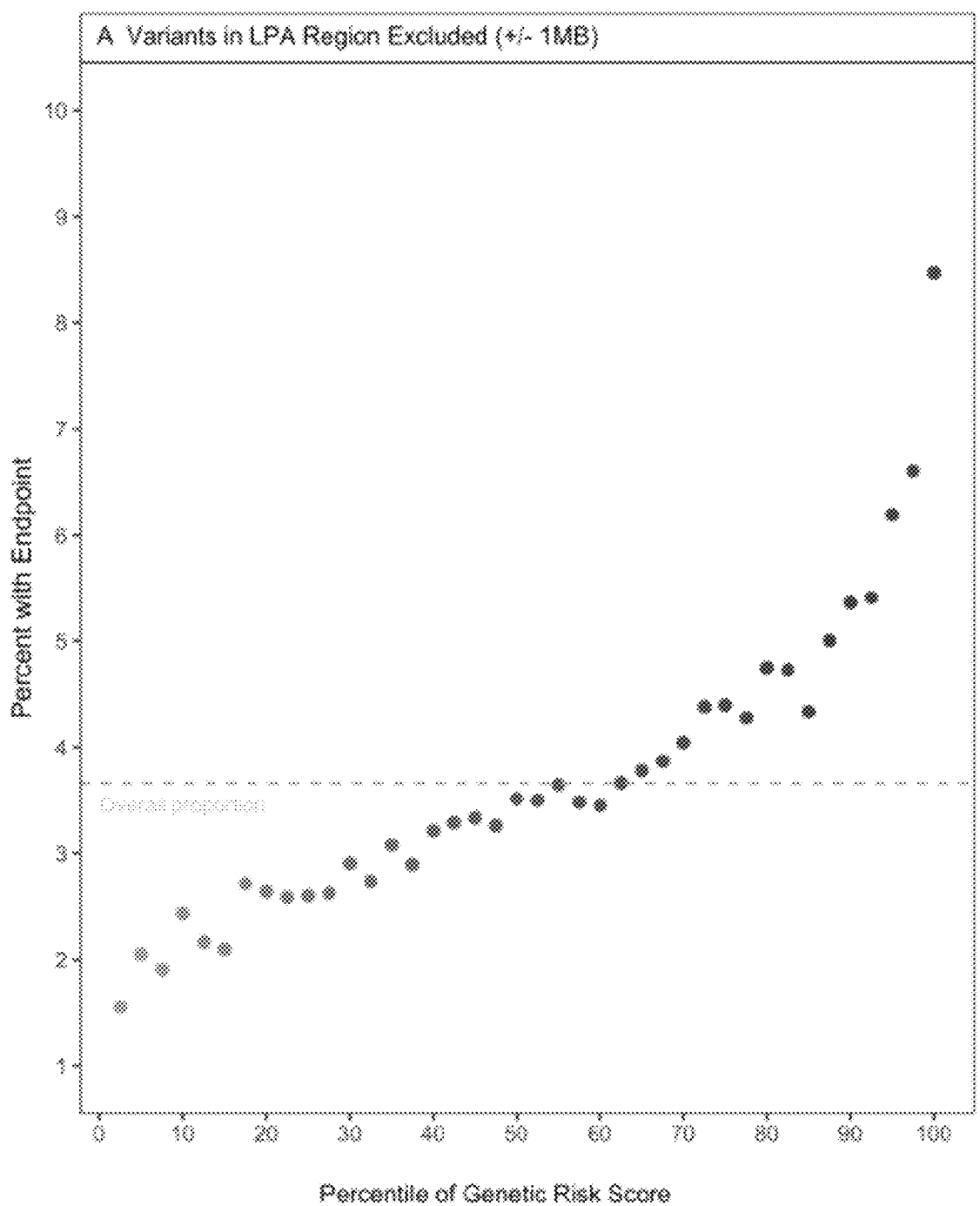
FIG. 22 shows UKB: Composite endpoint of myocardial infarction, angina, or ischemic stroke, excluding/including LPA gene region. Results shown for the composite endpoint of myocardial infarction, angina, or ischemic stroke, excluding and including the LPA gene region (+/−1 MB) in the score. Panel A displays the genome-wide PRS with the LPA gene region excluded (+/−1 MB); and Panel B displays the genome-wide score.
Figure 22:
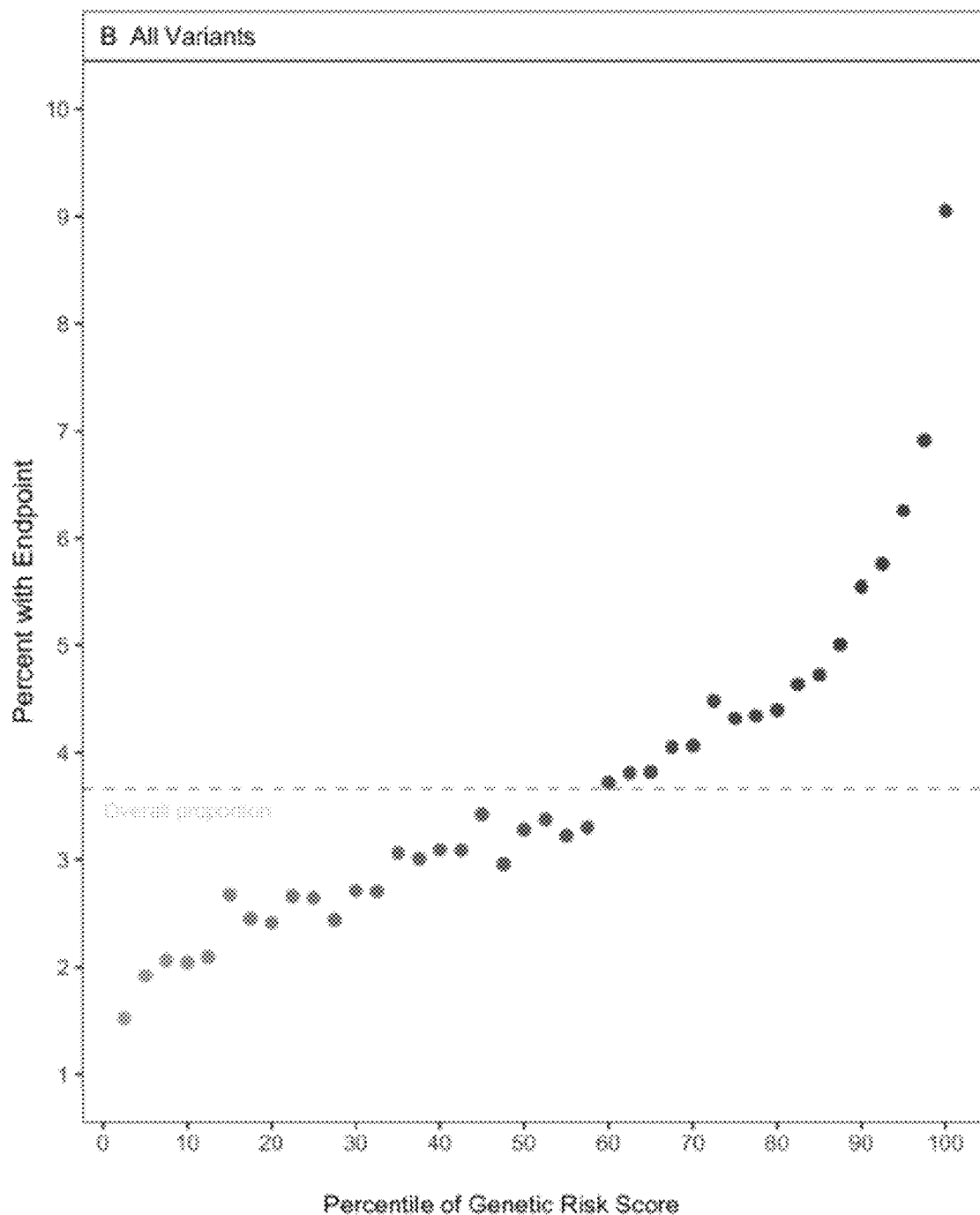
Figure 23:
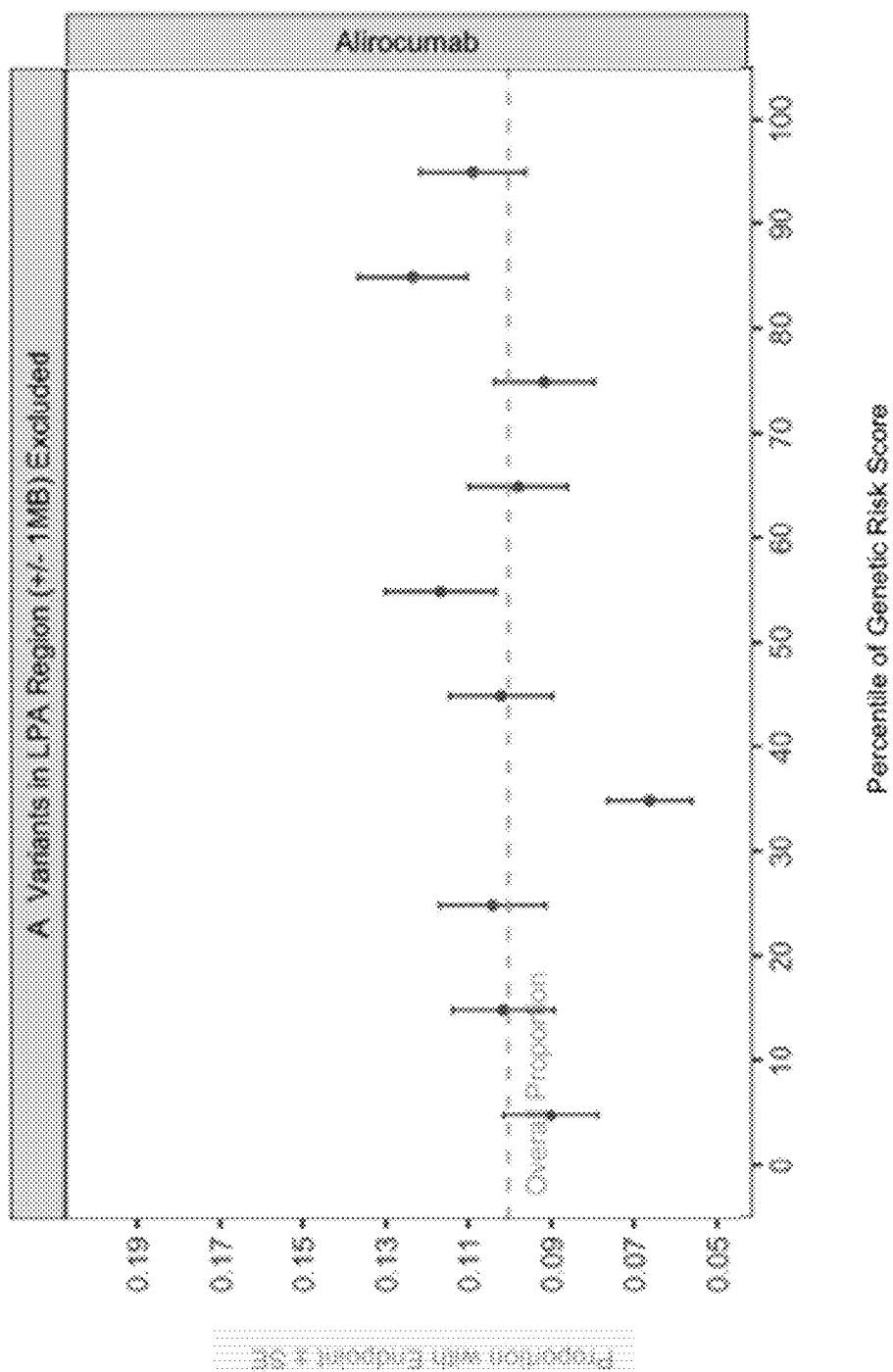
FIG. 23 shows incidence of MACE in ODYSSEY placebo arm, excluding/including LPA gene region. Result shown for MACE (composite end point including death from coronary heart disease, nonfatal myocardial infarction, fatal or nonfatal ischemic stroke, or unstable angina requiring hospitalization) excluding and including the LPA gene region (+/−1 MB) in the score. Panel A displays the genome-wide PRS with the LPA gene region excluded (+/−1 MB); and Panel B displays the genome-wide score.
Figure 23:
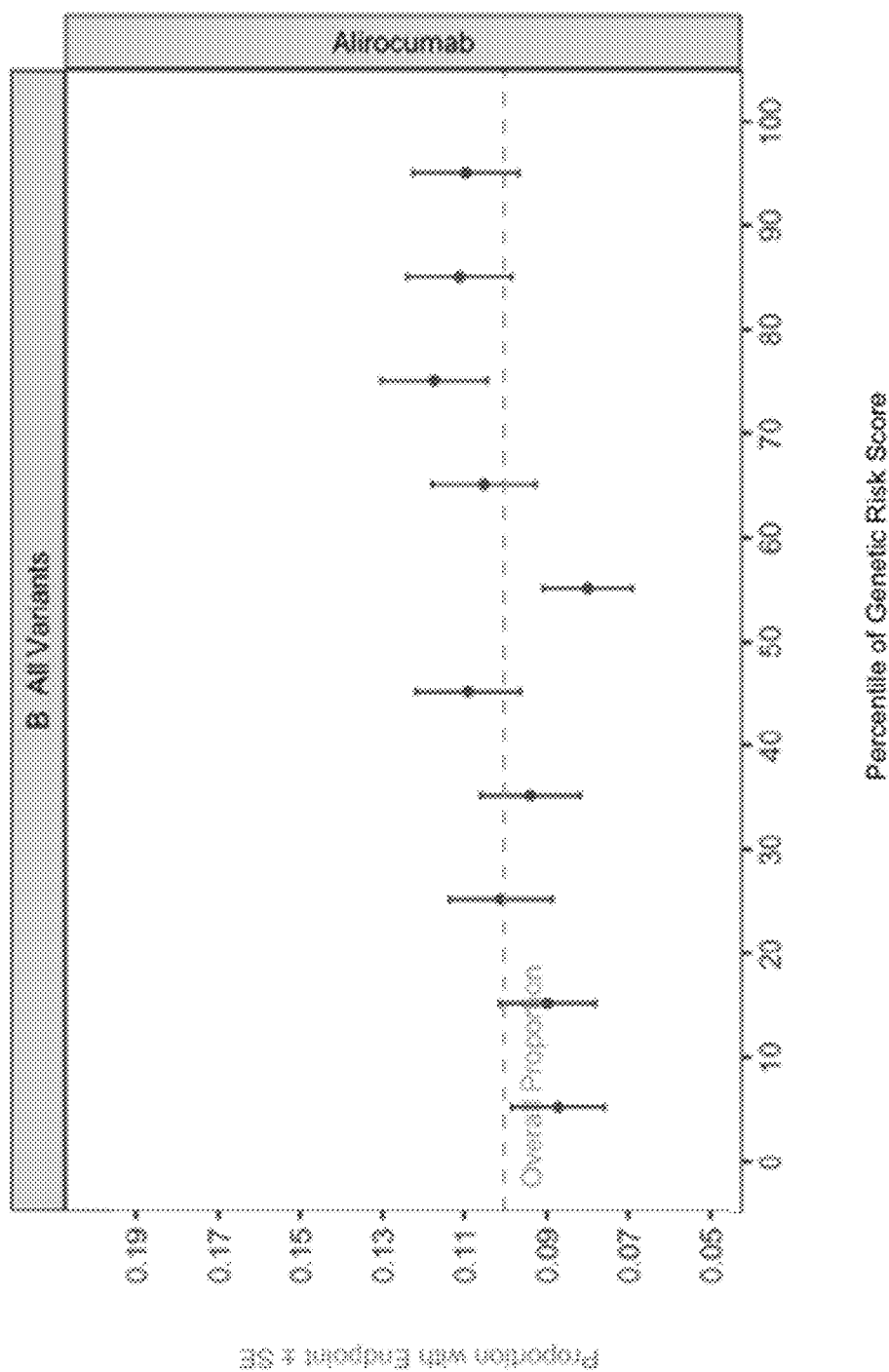
Figure 23:
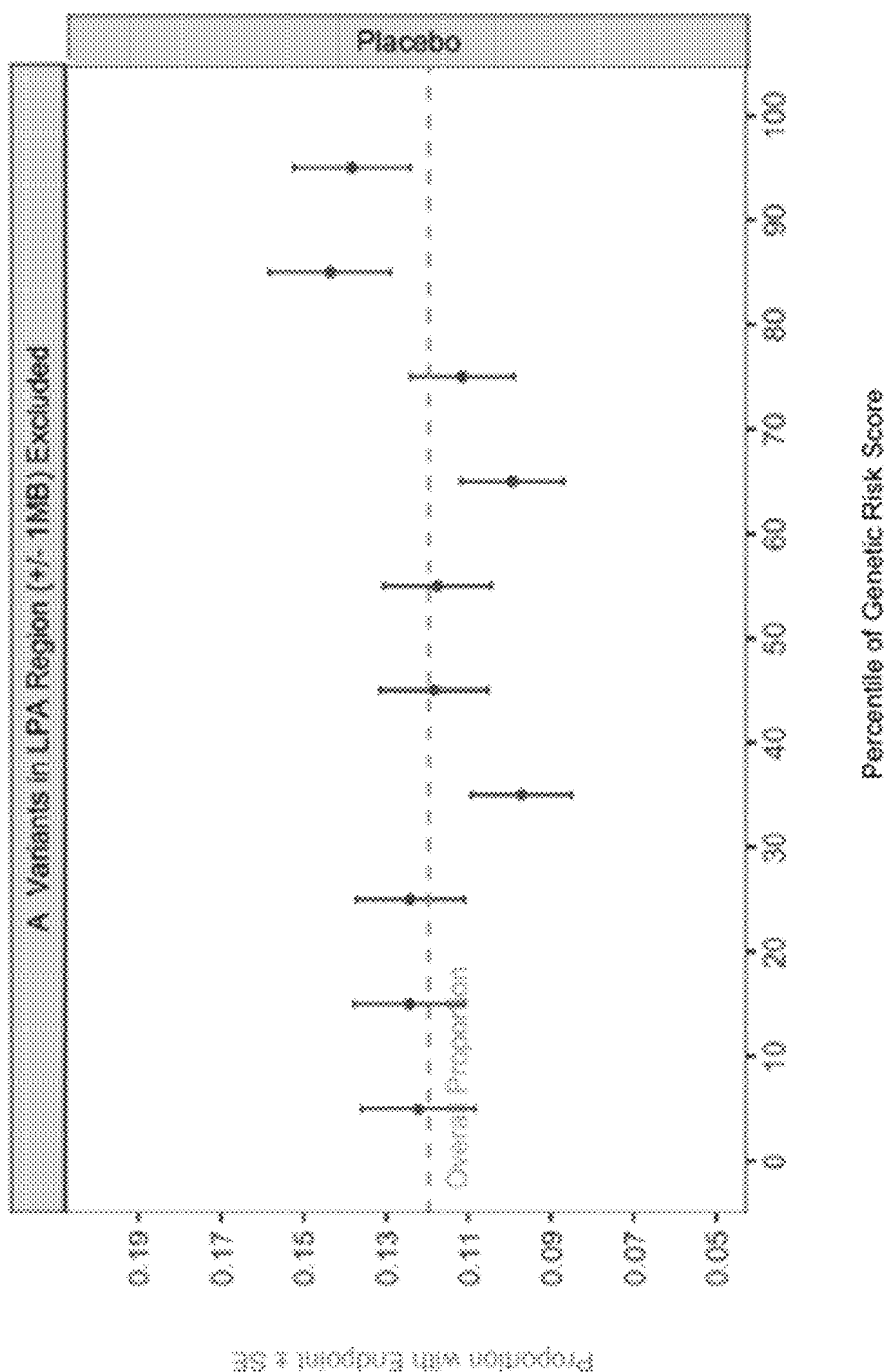
Figure 23:
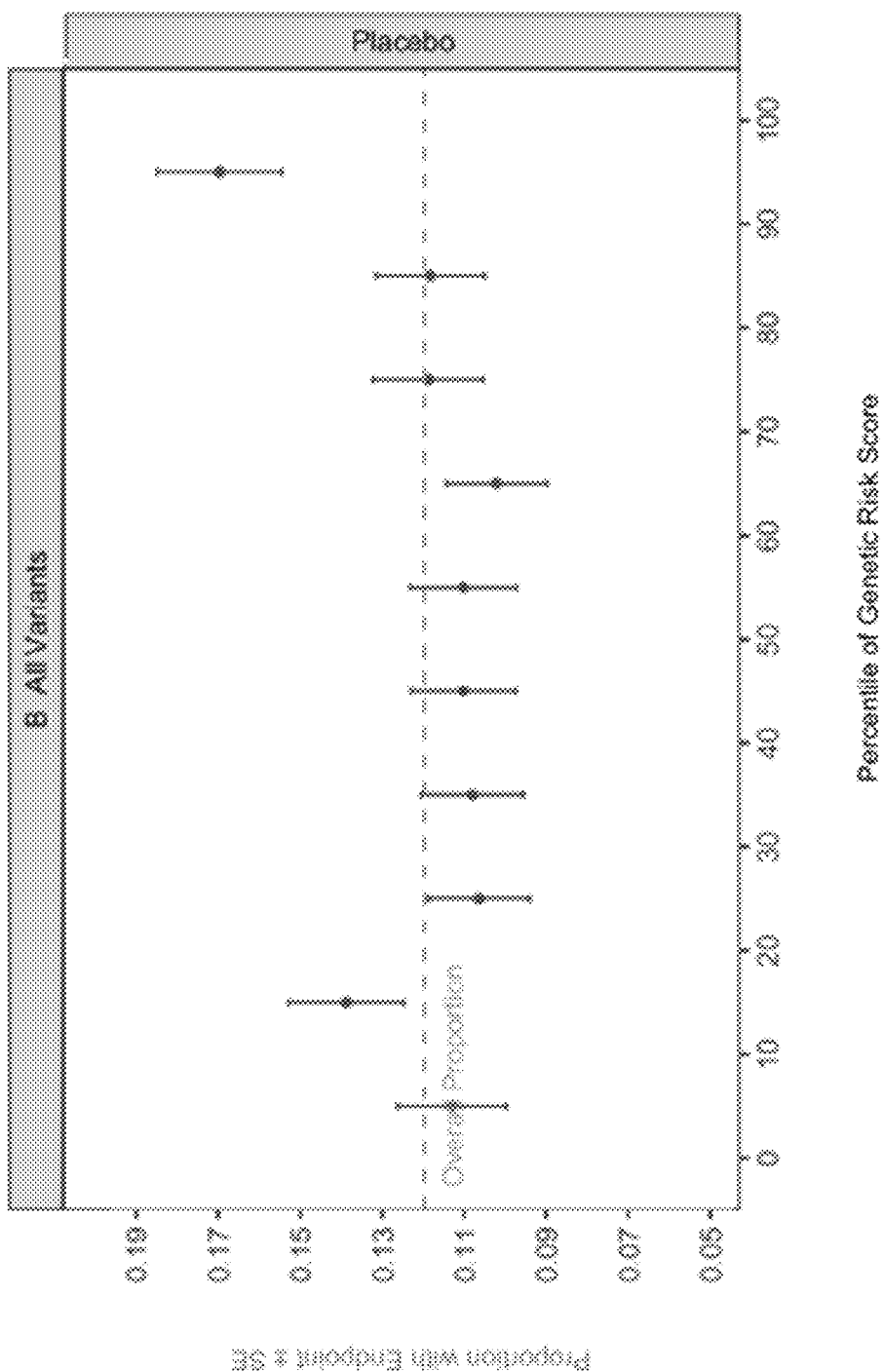

In UKB, the modified PRS, still had a strong association within MACE in UK Biobank (OR per SD 1.5, p<0.001). In MACE risk in ODYSSEY, removing these LPA regions split the risk in the top decile placebo arm among the top two deciles (FIGS. 22-23). Among placebo-treated patients in the top decile who had an event, 35% (36 of 104) shift from the top decile, with the majority shifting into the next highest decile (suggesting that the LPA region is an important but not sole contributor to risk). Among these 'shifted' patients, approximately 28% (10 of 36) have baseline serum Lp(a) <50 mg/dL. In further evaluation of this region, it was noted that the LPA region PRS was only moderately correlated with baseline serum Lp(a) levels, $r^2$=27.7%. Results in UK Biobank were similar, the $r^2$ between the LPA region PRS and serum Lp(a) levels (nmol/L) was 29.0%. In summary, serum Lp(a) is not a simple proxy for MACE risk from the LPA genomic region, which is why the PRS still has a strong association with risk after adjusting for or stratifying by baseline Lp(a). The LPA genomic region was more influential in the 27 SNP score, as 2 of the 27 variants in this score are from the LPA region (rs10455872 and rs3798220). Among placebo treated patients in the top decile of 27 variant risk score, 96 had a MACE event. After removing these two variants from the score, 56 of 96 patients (58%) shifted from the top decile. These variants and other variants from the LPA locus may be playing a large role across different PRS scores, from smaller scores such at the 27 SNP score, to the larger genome-wide PRS scores.

Evaluation of Genetic Risk and Impact on Major Cardiovascular Events.

Figure 4:
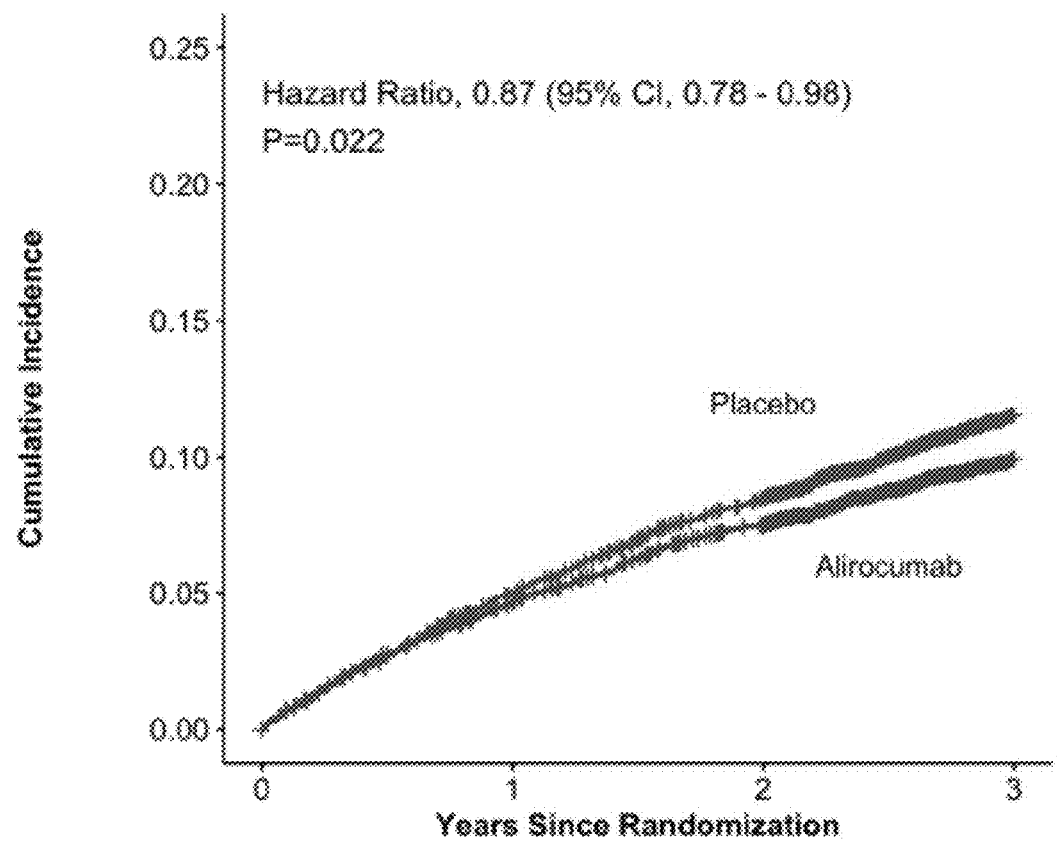
FIG. 4 shows cumulative incidence of MACE in the lower genetic risk group (Panel A; PRS ≤90th percentile) and high genetic risk group (Panel B; PRS >90th percentile). Shown is the cumulative incidence of MACE in patients of all ancestries, stratified by genetic risk. The hazard ratios and p-values were calculated from a cox proportional hazards model, which was adjusted for ancestry, baseline LDL-C, Lp(a), age, sex, family history of premature coronary heart disease, and the following medical characteristics prior to index ACS: myocardial infarction; percutaneous coronary intervention; coronary artery bypass grafting; and congestive heart failure. In addition to the genetic risk stratified analyses, a cox model that included treatment arm, genetic risk (high/lower), treatment-by-genetic risk interaction, and covariates noted above was performed. The treatment-by-genetic risk interaction p-value was 0.040.
Figure 4:
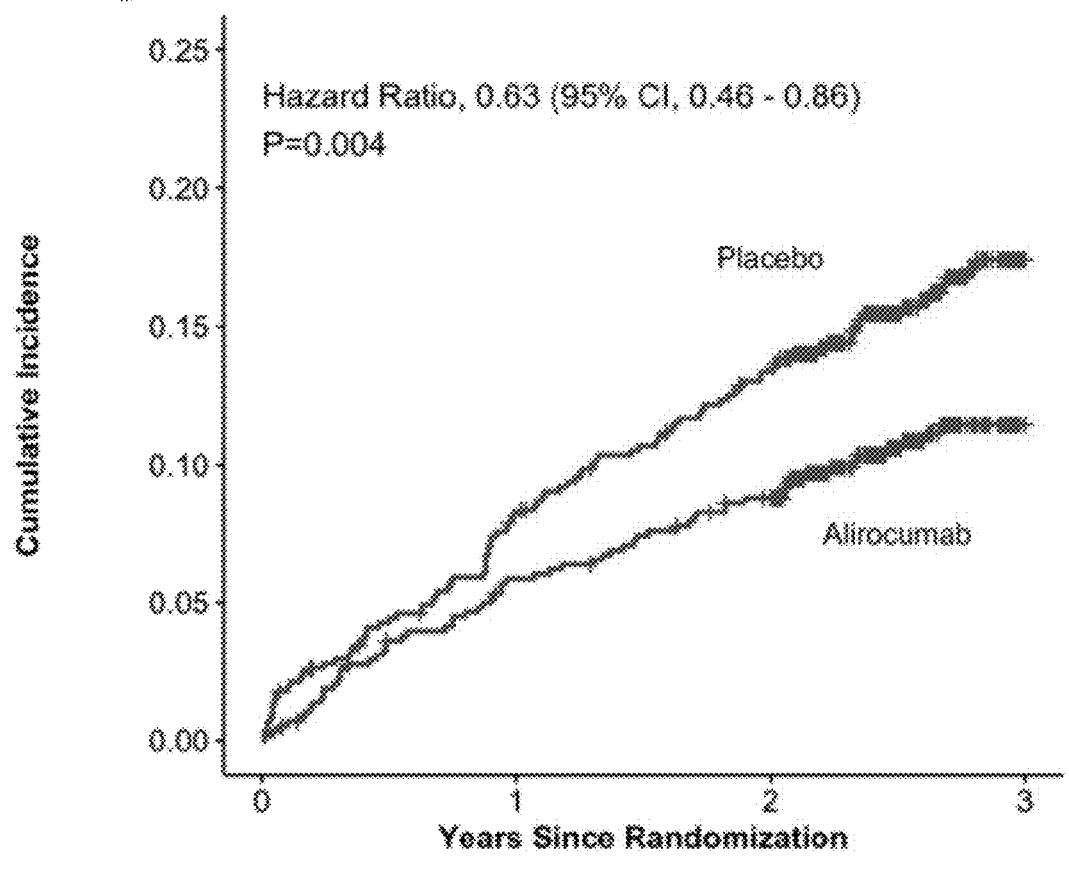

Whether patients with high genetic risk would receive greater benefit from treatment with alirocumab was then tested. It was observed that high genetic risk patients on alirocumab had greater reductions in both absolute and relative risk for MACE, compared to lower genetic risk patients. In the high genetic risk group, the Kaplan-Meier cumulative incidence at 3 years for the MACE was 11.4% in the alirocumab group and 17.4% in the placebo group, corresponding to an absolute risk reduction of 6.0%. In the lower risk genetic group, the rates were 10.0% and 11.5%, respectively (FIG. 4), corresponding to an absolute risk reduction of 1.5%. To prevent the occurrence of one primary end point, 17 (95% CI, 11-96) high genetic risk patients or 64 (95% CI, 34-546) lower genetic risk patients would need to be treated 3 years. Patients with high genetic risk also had greater relative reduction in MACE with alirocumab (HR 0.63; 95% CI 0.46-0.86; p=0.004) compared to those with lower genetic risk (HR 0.87; 95% CI 0.78-0.98 p=0.022). This difference was statistically significant (PRS by-treatment interaction p=0.04) (FIG. 4).

These analyses also demonstrated that high genetic risk patients showed larger reductions with alirocumab treatment than lower genetic risk patients in pre-defined major secondary endpoints that were significantly reduced with alirocumab in the overall study (any cardiovascular event, any coronary heart disease event, major coronary heart disease event, and the composite endpoint of death from any cause, nonfatal myocardial infarction, or nonfatal ischemic stroke) (FIG. 5). Analysis of any cause of death was limited by the small number of events in the high genetic risk group (44 events in total). While the overall numbers in the high genetic risk group were lower in the alirocumab treated patients (n=20 of 584; 3.4%) vs. the placebo treated patients (n=24 of 613; 3.9%), the number of events was too small for inferential analyses.

Figure 24:
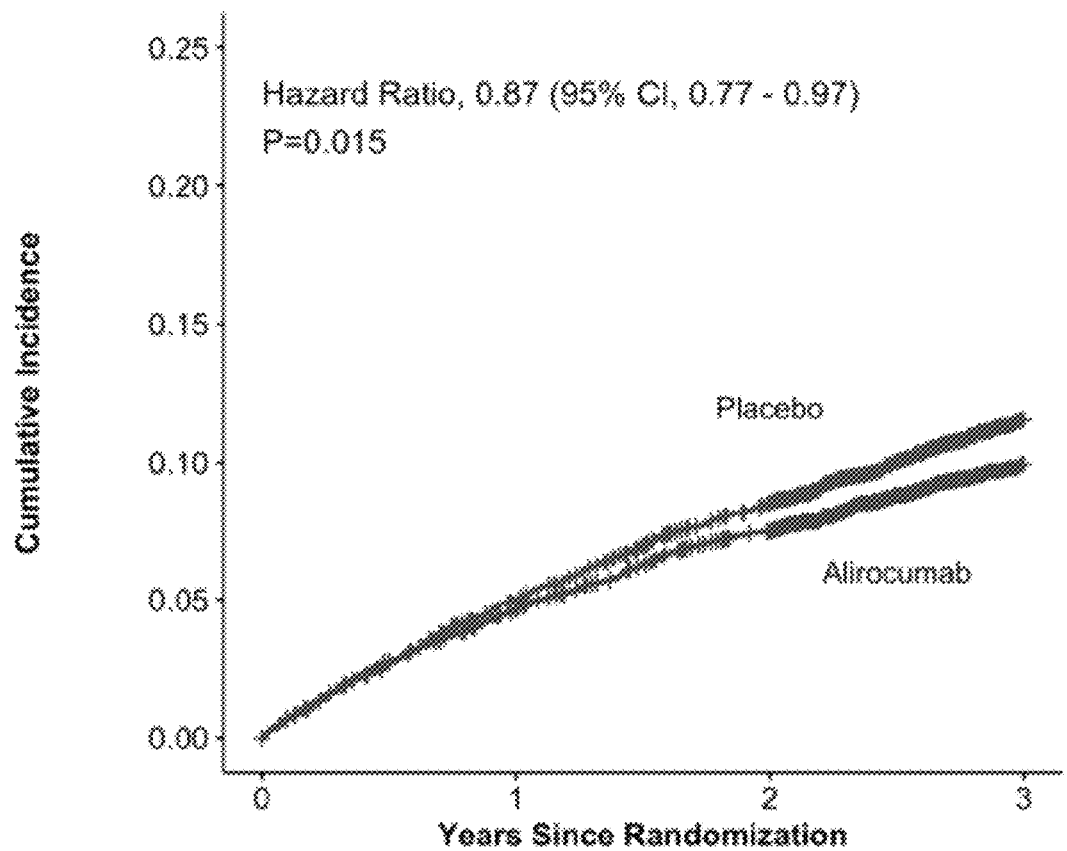
FIG. 24 shows cumulative incidence of MACE in the lower genetic risk group (PRS ≤90 percentile; Panel A) and high genetic risk group (PRS >90 percentile; Panel B) in patients of European ancestry. Shown is the cumulative incidence of MACE (a composite of death from coronary heart disease, nonfatal myocardial infarction, fatal or nonfatal ischemic stroke, or unstable angina requiring hospitalization) in patients of European ancestry, stratified by genetic risk. The hazard ratios and p-values were calculated from a cox proportional hazards model, which was adjusted for ancestry, baseline LDL-C, Lp(a), age, sex, family history of premature coronary heart disease, percutaneous coronary intervention or coronary-artery bypass grafting for index acute coronary syndrome and the following medical characteristics prior to index ACS: myocardial infarction; percutaneous coronary intervention; coronary artery bypass grafting; and congestive heart failure. In addition to the genetic risk stratified analyses, a Cox model that included treatment arm, genetic risk (high/lower), treatment-by-genetic risk interaction, and covariates noted above was also performed. The genetic risk by treatment arm interaction p-value was 0.113.
Figure 24:
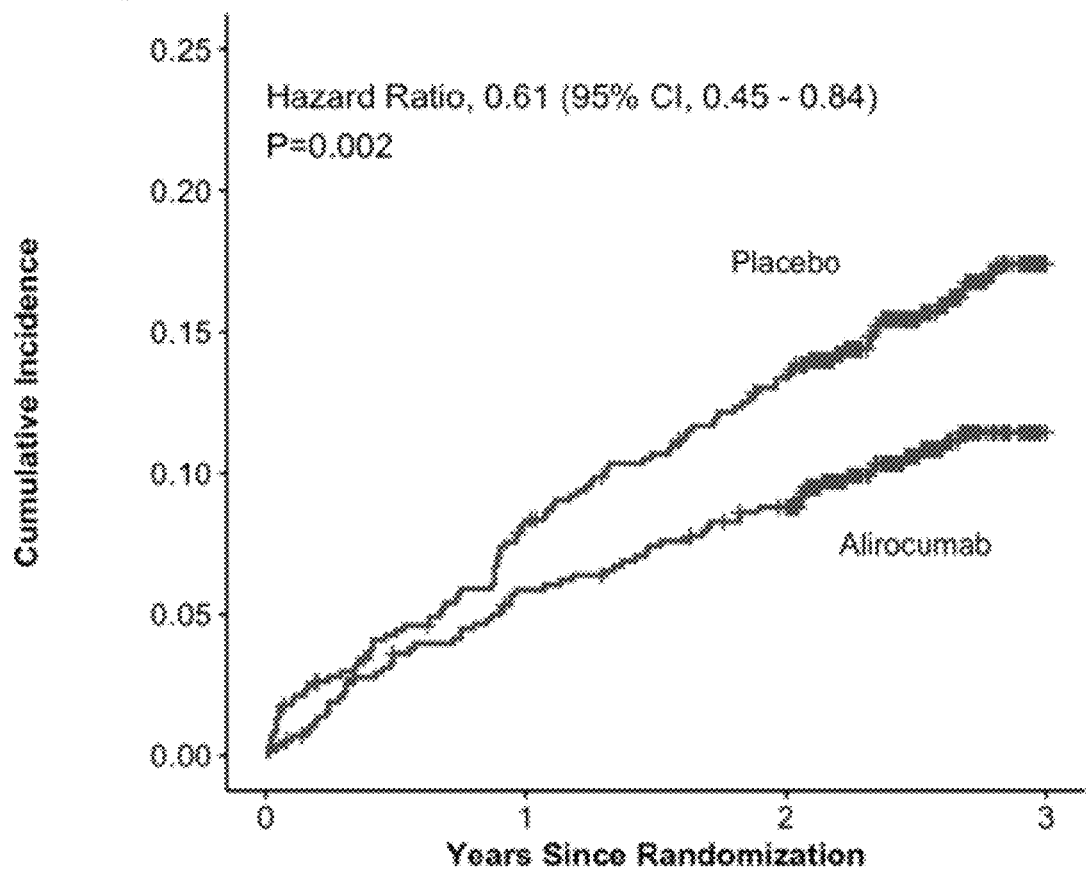

Patients of European ancestry comprised 78% of the analysis population and this subgroup was the largest ancestry group in the overall analysis. Accordingly, subgroup analysis was performed for the European ancestry patients. The results for European ancestry patients with high genetic risk (MACE HR 0.64; 95% CI 0.45-0.92; p=0.016) were consistent with the overall analysis that included patients of all ancestries (FIGS. 12 and 24).

Independent and Additive Value of PRS and Pre-Treatment LDL-C Levels for Predicting Benefit from Alirocumab.

Figure 6:
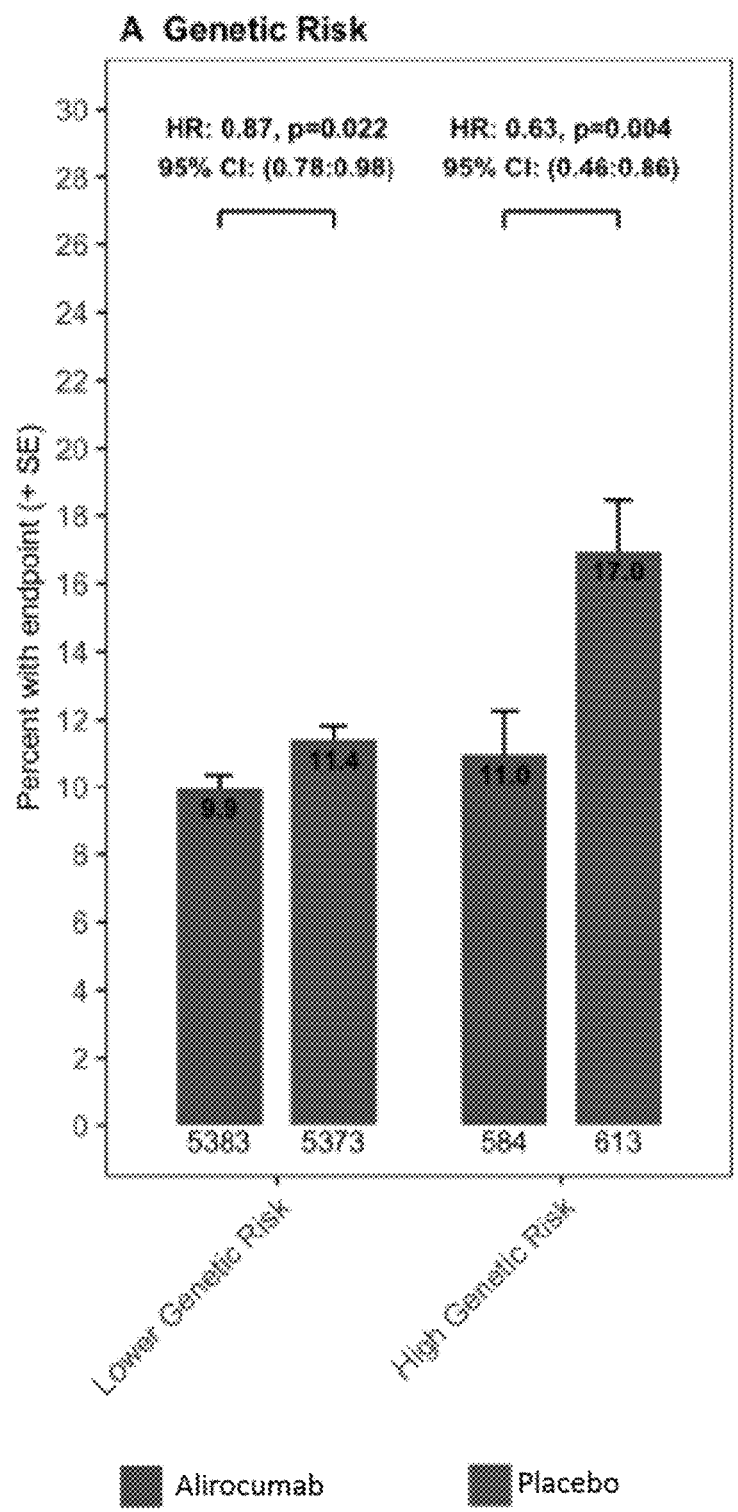
FIG. 6 shows incidence of MACE stratified by genetic risk and LDL cholesterol levels at baseline. Shown is the percent with an event (overall incidence) in patients of all ancestries, stratifying by genetic risk and/or LDL-C at baseline. Panel A stratifies by genetic risk (high genetic risk is PRS >90th percentile; lower genetic risk is PRS ≤90th percentile). Panel B stratifies by LDL-C at baseline (LDL-C ≥100 mg/dL and LDL-C <100 mg/dL). Panel C stratifies both by genetic risk and LDL-C at baseline. The numbers at the bottom of each panel are the number of patients in each group and the number inside each bar is the percent with MACE in each group. The hazard ratios and p-values were calculated from a cox proportional hazards model, which was adjusted for ancestry, baseline LDL-C, Lp(a), age, sex, family history of premature coronary heart disease, and the following medical characteristics prior to index ACS: myocardial infarction; percutaneous coronary intervention; coronary artery bypass grafting; and congestive heart failure.
Figure 6:
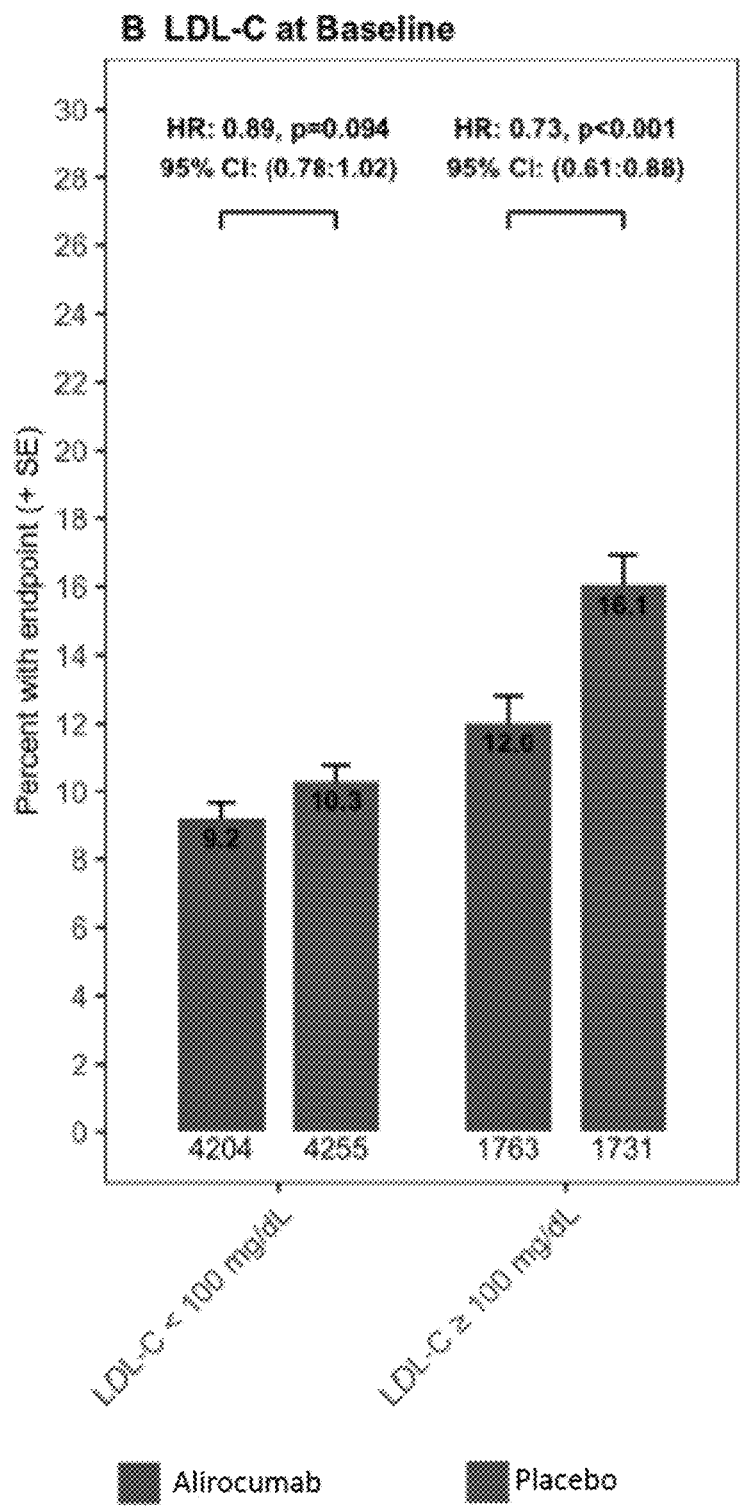
Figure 6:
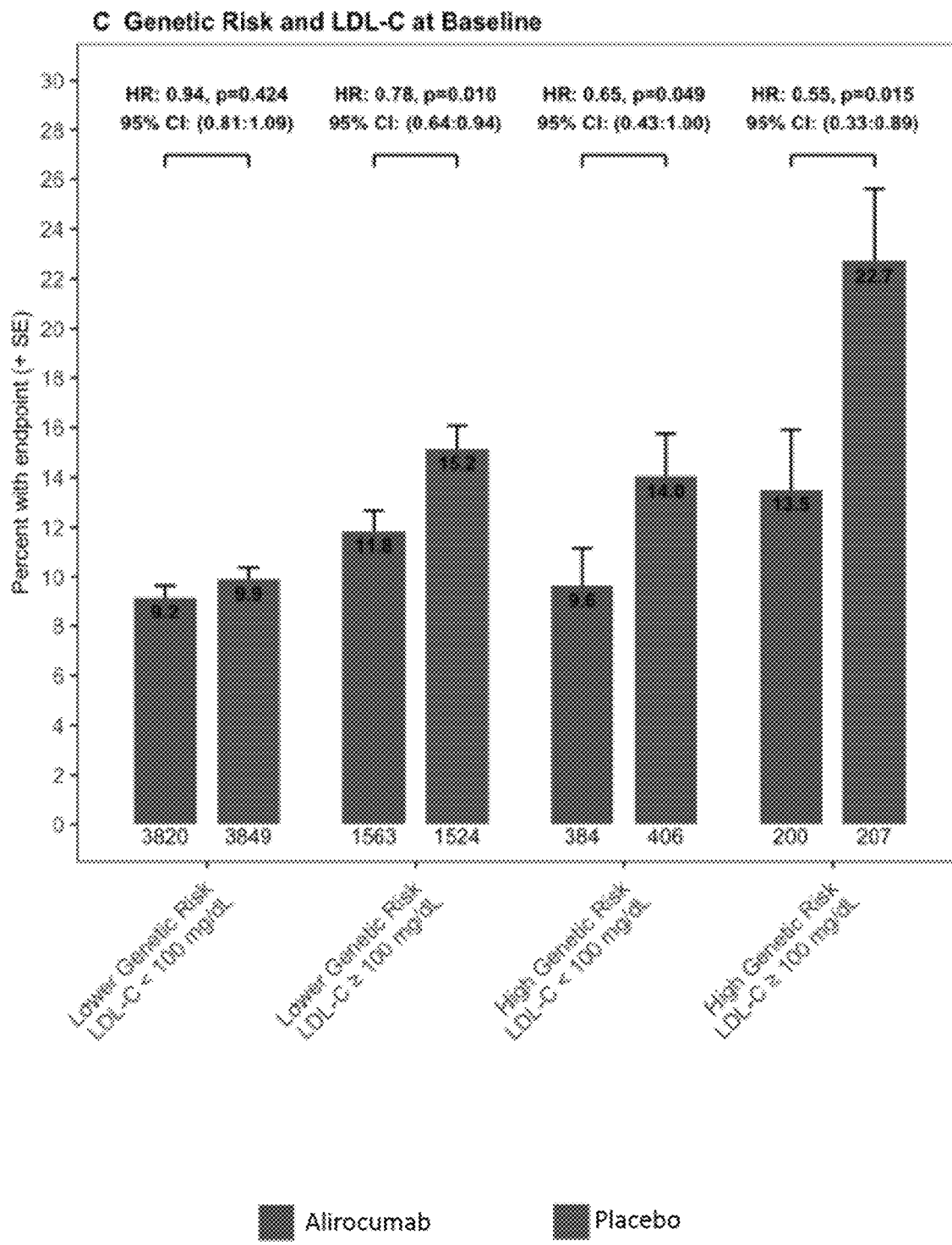
Figure 7:
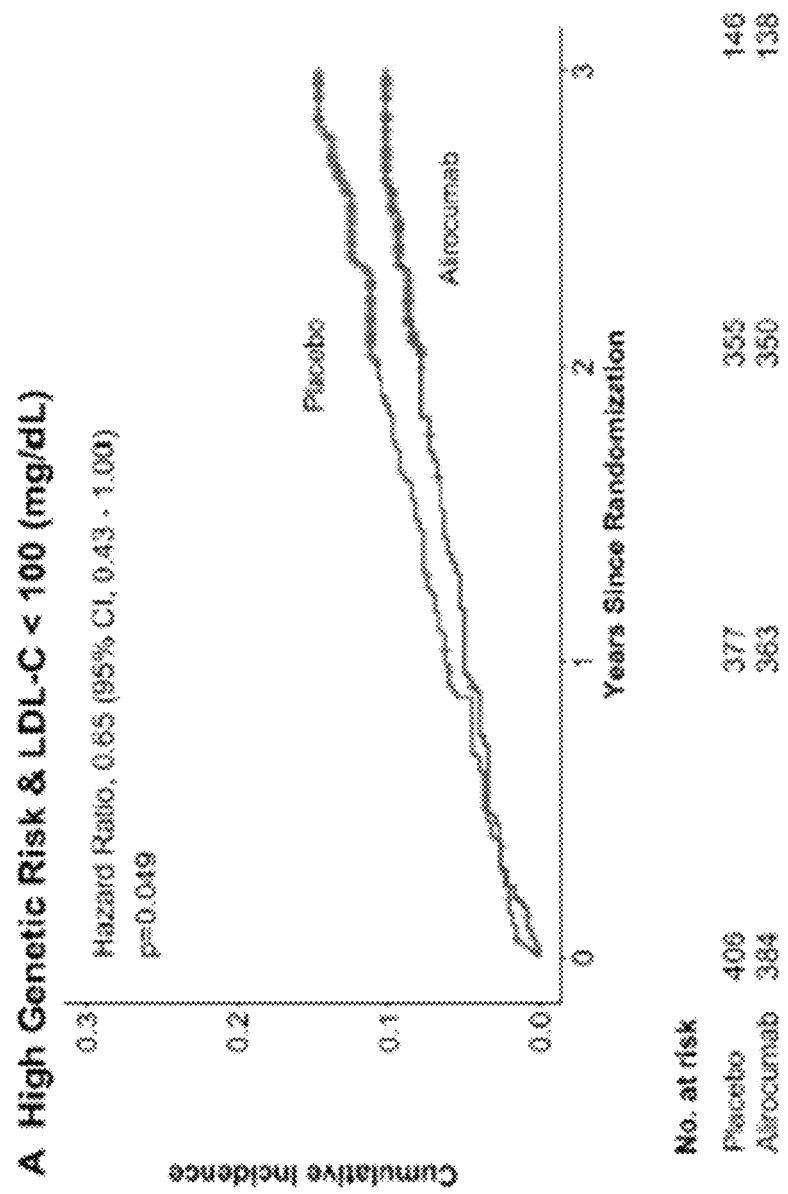
FIG. 7 shows cumulative incidence of MACE, stratified by genetic risk and LDL cholesterol levels at baseline. Shown is the cumulative incidence in patients of all ancestries with high genetic risk (PRS >90th percentile; Panels A and B), and lower genetic risk (PRS ≤90th percentile; Panels C and D), further stratified by LDL-C at baseline. Patients with LDL-C <100 mg/dL and high genetic risk are shown in Panel A and LDL-C ≥100 mg/dL and high genetic risk is shown in Panel B. Similarly, patients with LDL-C <100 mg/dL and lower genetic risk are shown in Panel C and LDL-C ≥100 mg/dL and lower genetic risk is shown in Panel D. The hazard ratios and p-values were calculated from a cox proportional hazards model, which was adjusted for ancestry, baseline Lp(a), age, sex, family history of premature coronary heart disease, and the following medical characteristics prior to index ACS: myocardial infarction; percutaneous coronary intervention; coronary artery bypass grafting; and congestive heart failure. The treatment-by-genetic risk-by-baseline LDL-C interaction p>0.05.
Figure 7:
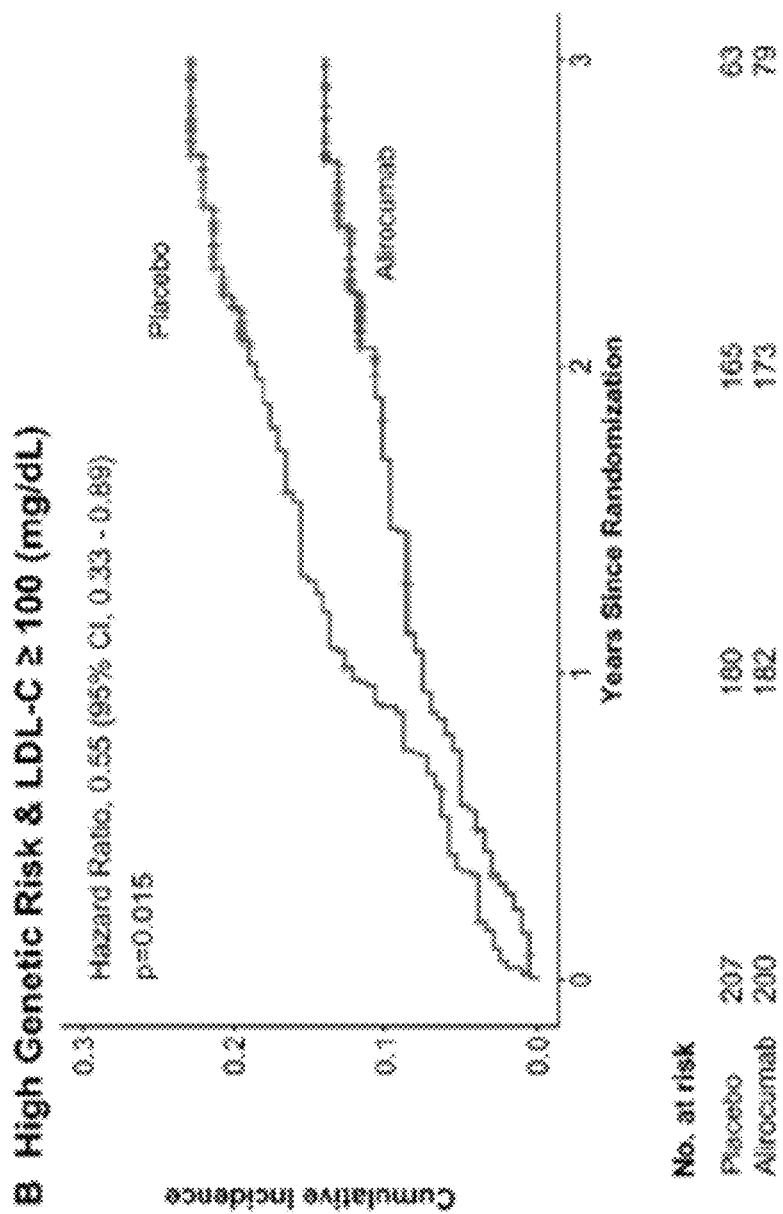
Figure 7:
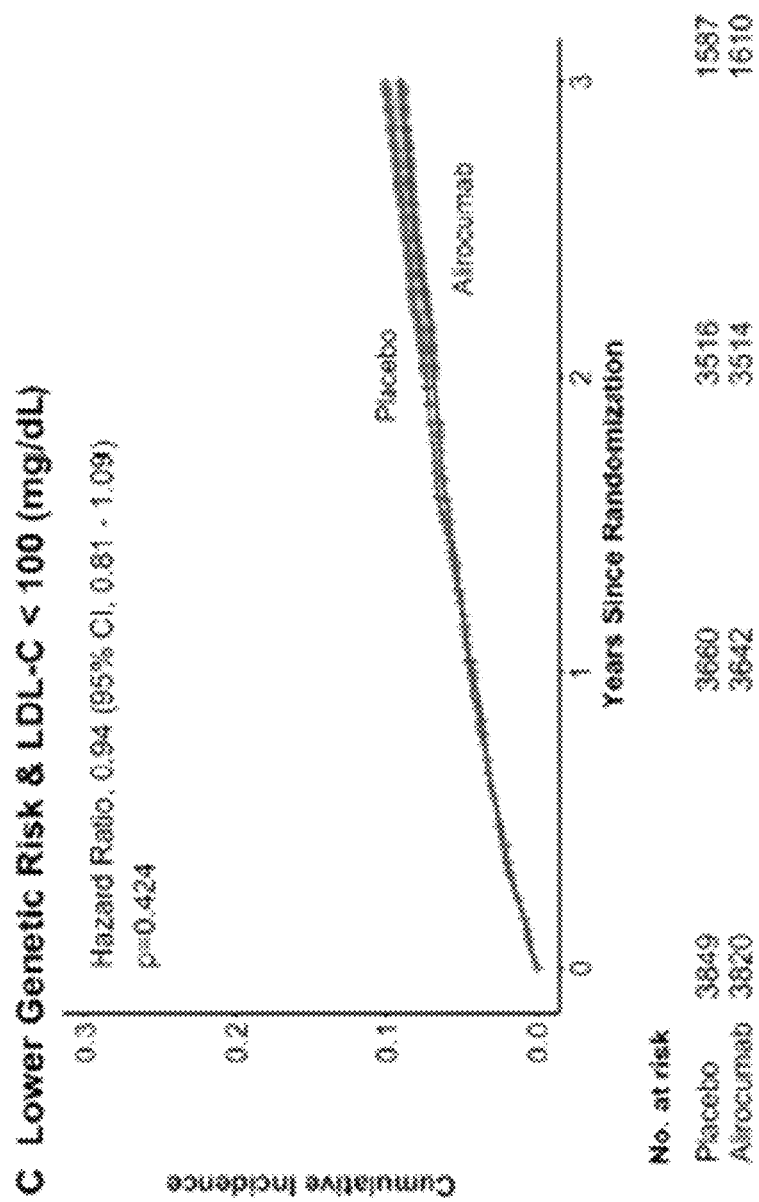
Figure 7:
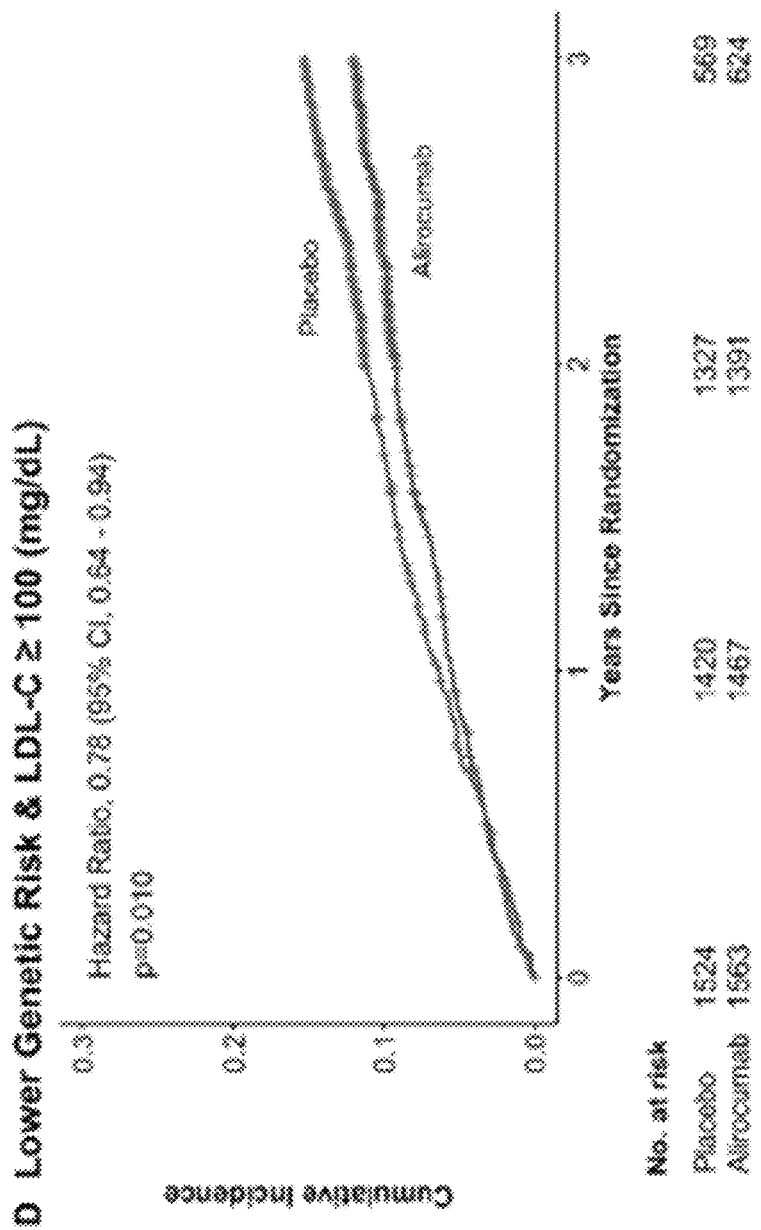

The relationship of baseline LDL-C (dichotomized at 100 mg/dL), PRS, and treatment on the risk of MACE was also explored. In the group with both high genetic risk and high baseline LDL-C, the Kaplan-Meier cumulative incidence at 3 years for MACE was 22.7% in the placebo group and was markedly reduced by alirocumab treatment (13.4%), (FIG. 6C), corresponding to a risk reduction of 9.2% (95% CI 1.8%-6.6%). In the group with both lower genetic risk and low baseline LDL-C, the rates were 9.9% and 9.2%, respectively (FIG. 6C), corresponding to risk reduction of 0.7%, 95% CI (−0.6%-2.1%). The hazard ratio for MACE (alirocumab:placebo) was numerically lowest in patients with both high genetic risk and high LDL-C (≥100 mg/dL) (HR 0.55; 95% CI 0.33-0.89; p=0.015) and numerically highest in patients with low LDL-C (<100 mg/dL) and lower PRS (HR 0.94; 95% CI 0.81-1.09; p=0.424, FIG. 7). It should be noted that this difference was not statistically significant when evaluating the full Cox regression model (p>0.05).

Effects of Genetic Risk and Alirocumab Treatment by VHR Status.

Figure 28:
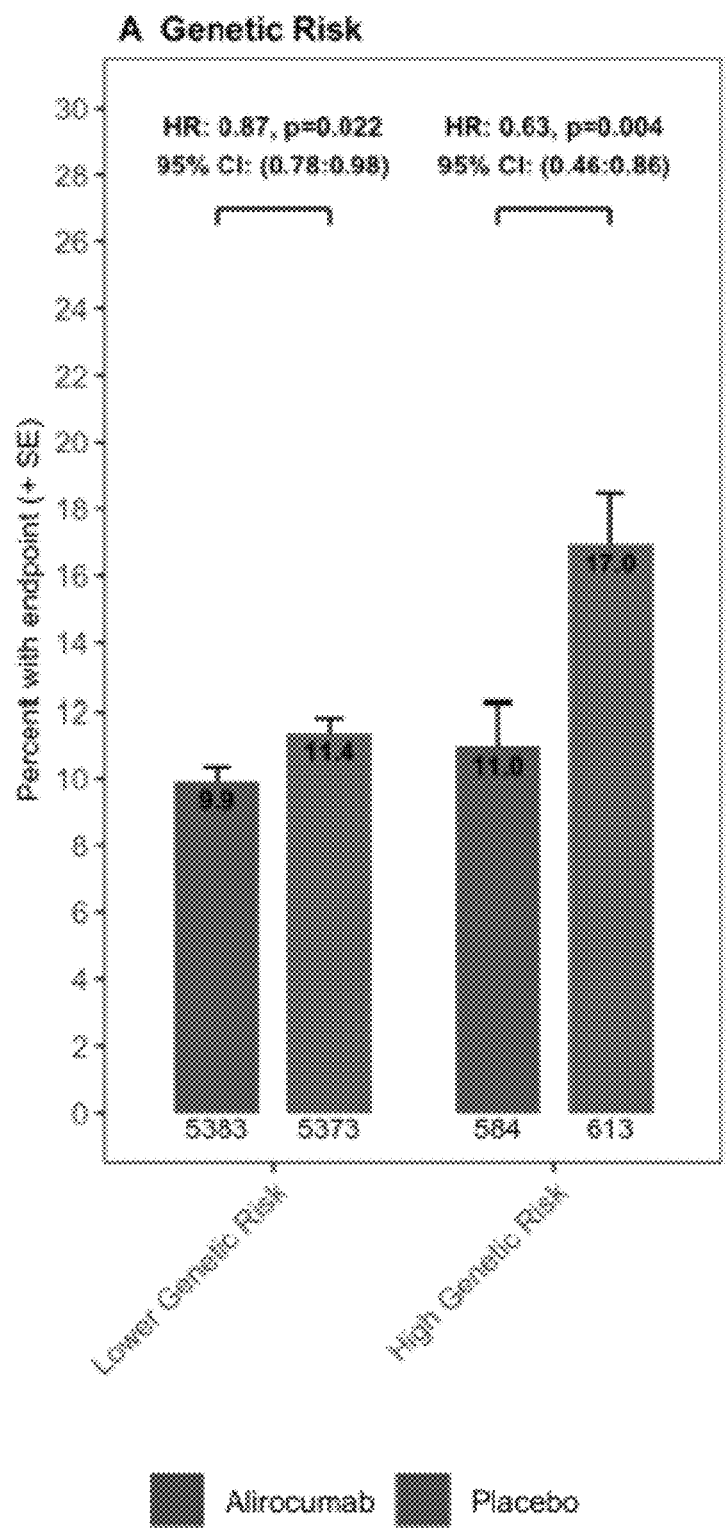
FIG. 28 shows MACE stratified by genetic risk and baseline Lp(a) taking into consideration VHR category. Panel A is stratified by genetic risk, where high genetic risk is PRS >90 percentile; lower genetic risk is PRS ≤90 percentile. Panel B is stratified by Lp(a) at baseline (Lp(a) ≥50 mg/dL and Lp(a) <50 mg/dL). Panel C is stratified by genetic risk and Lp(a) at baseline. The numbers at the bottom of each panel are the number of patients in each group and the number inside each bar is the percent with MACE in each group. The hazard ratios and p-values were calculated from a Cox proportional hazards model, adjusted for ancestry, baseline LDL-C, Lp(a), age, sex, family history of premature coronary heart disease, and the following medical characteristics prior to index ACS: myocardial infarction; percutaneous coronary intervention; coronary artery bypass grafting; and congestive heart failure.
Figure 28:
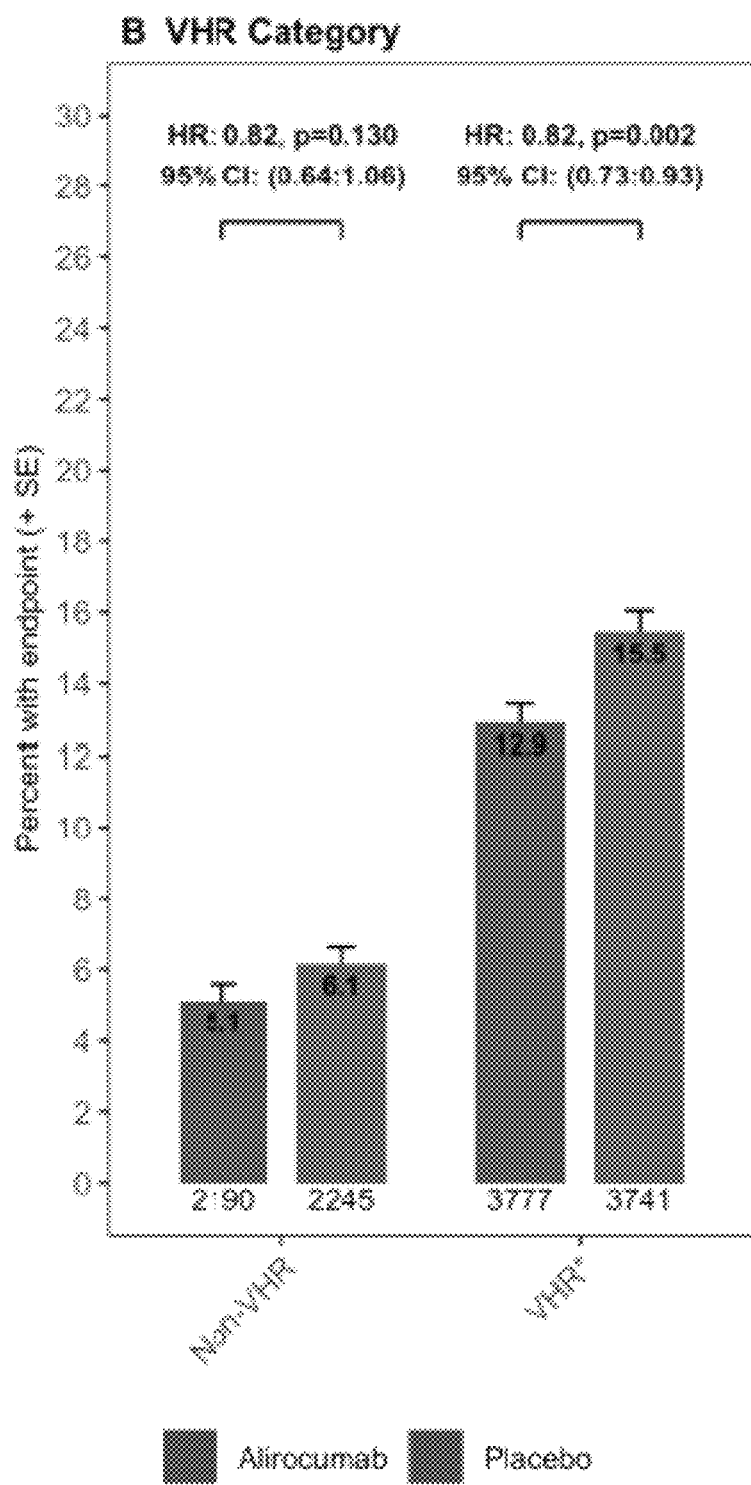
Figure 28:
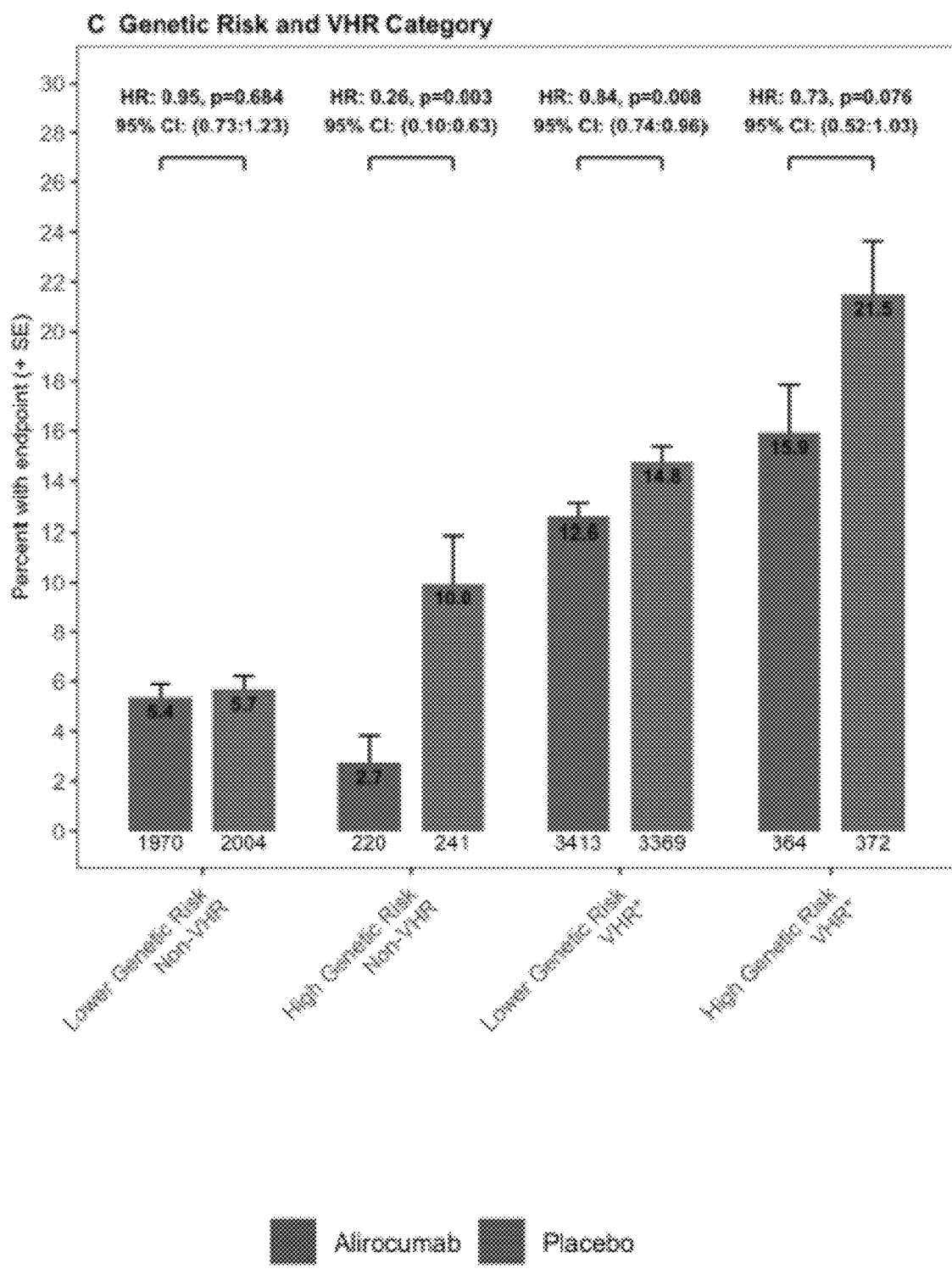

Treatment benefit by VHR status was evaluated using the VHR criteria described previously. In the non-VHR high genetic risk group, the absolute risk reduction associated with alirocumab was 7.3%, HR=0.26 (95% CI 0.10-0.63), p=0.003. In the VHR* high genetic risk group, the absolute risk reduction was 5.6%, HR=0.73 (95% CI 0.52-1.03), p=0.076. There were only 736 patients in the VHR* high genetic risk group, the p-value trends toward significance with a 27% relative risk reduction (FIG. 28). These results suggest that patients in the high genetic risk group receive alirocumab treatment benefit irrespective of VHR classification.

Effects of Genetic Risk and Alirocumab Treatment on Lipid Lowering.

The degree of lipid lowering in both the high and lower genetic risk patients after alirocumab treatment was then examined. The decrease in LDL-C with alirocumab was similar in both PRS groups: at 4 months, the median decrease was 57.0 mg/dL in high genetic risk patients and 58.7 mg/dL in lower genetic risk patients (FIG. 25).

Figure 26:
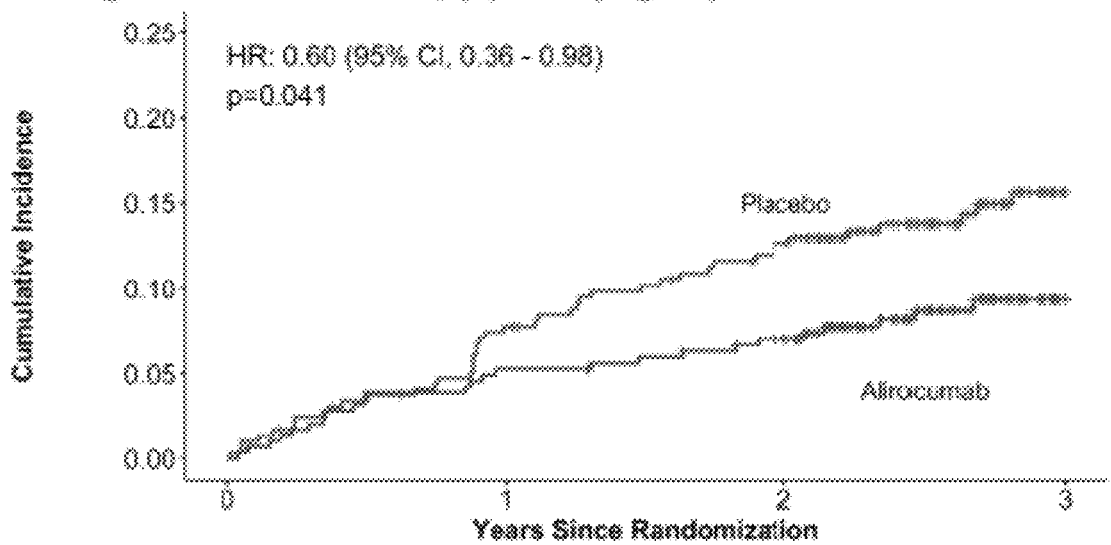
FIG. 26 shows cumulative incidence of MACE, stratified by Lp(a) levels and genetic risk at baseline. Shown is the cumulative incidence in patients of all ancestries with high genetic risk (PRS >90 percentile; Panels A and B), and lower genetic risk (PRS ≤90 percentile; Panels C and D), further stratified by Lp(a) at Baseline. Patients with Lp(a) <50 mg/dL and high genetic risk are shown in Panel A and Lp(a) ≥50 mg/dL and high genetic risk is shown in Panel B. Similarly, patients with Lp(a) <50 mg/dL and lower genetic risk are shown in Panel C and Lp(a) ≥50 mg/dL and lower genetic risk is shown in Panel D. The hazard ratios and p-values were calculated from a Cox proportional hazards model, which was adjusted for ancestry, baseline LDL-C, Lp(a), age, sex, family history of premature coronary heart disease, percutaneous coronary intervention or coronary-artery bypass grafting for index acute coronary syndrome and the following medical characteristics prior to index ACS: myocardial infarction; percutaneous coronary intervention; coronary artery bypass grafting; and congestive heart failure.
Figure 26:
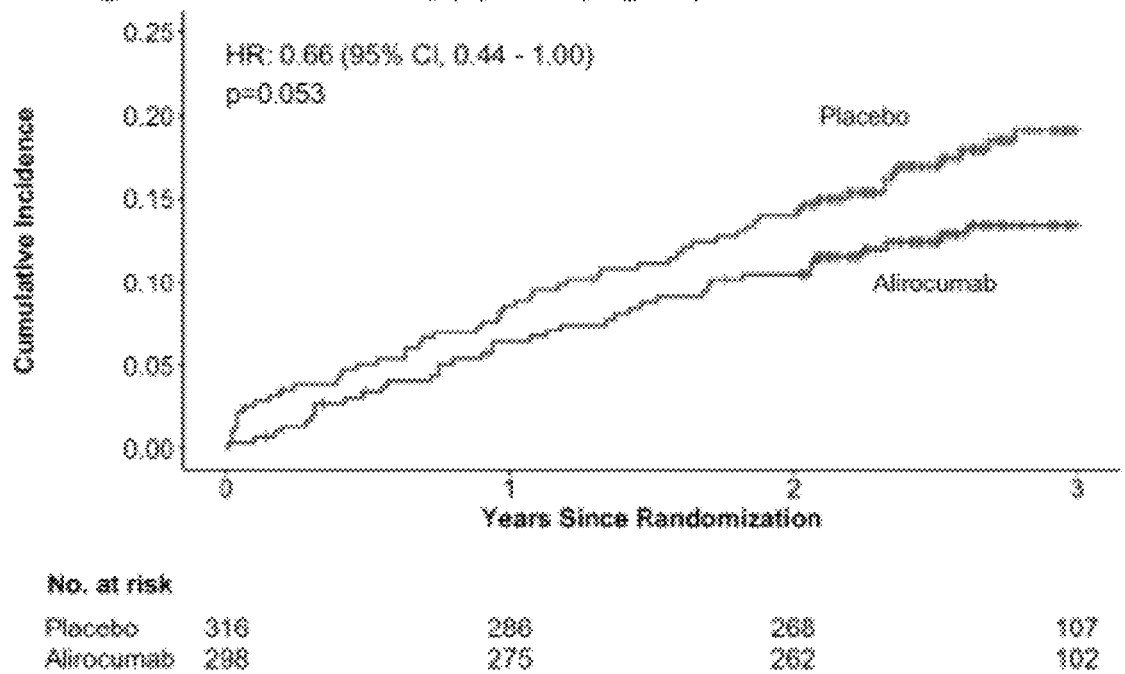
Figure 26:
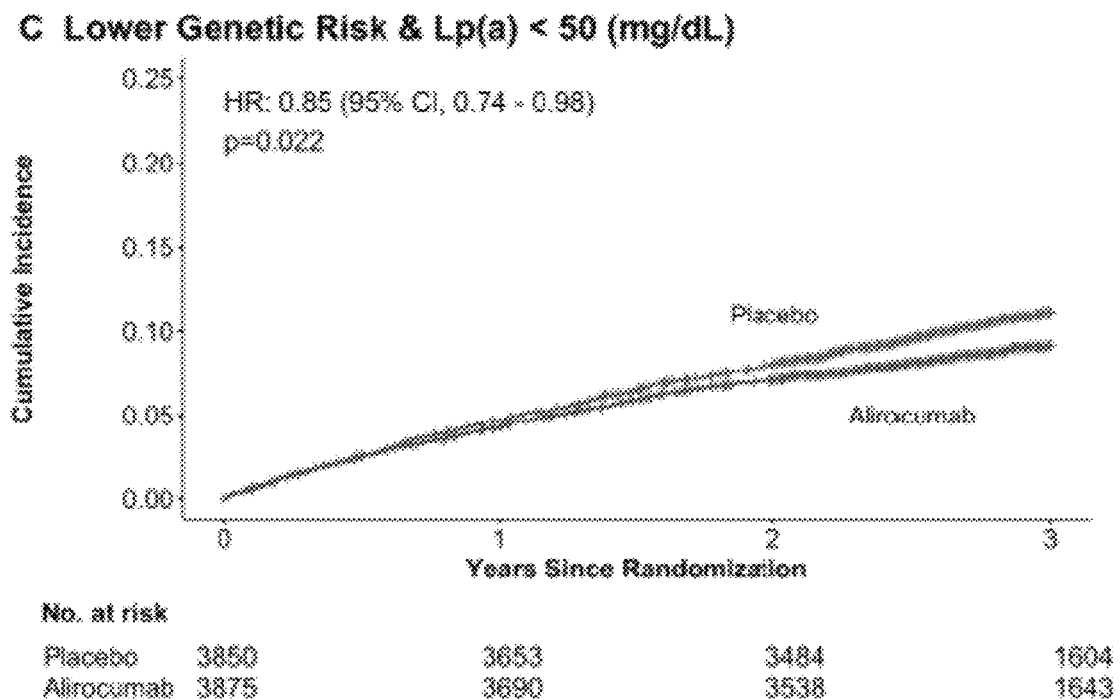
Figure 26:
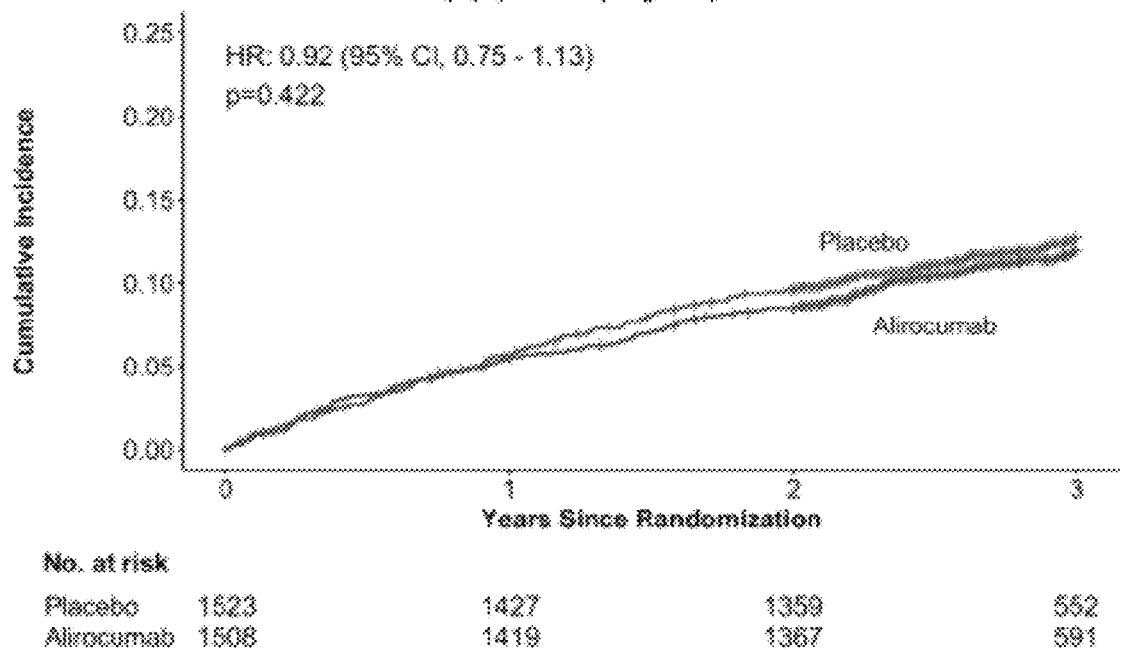
Figure 27:
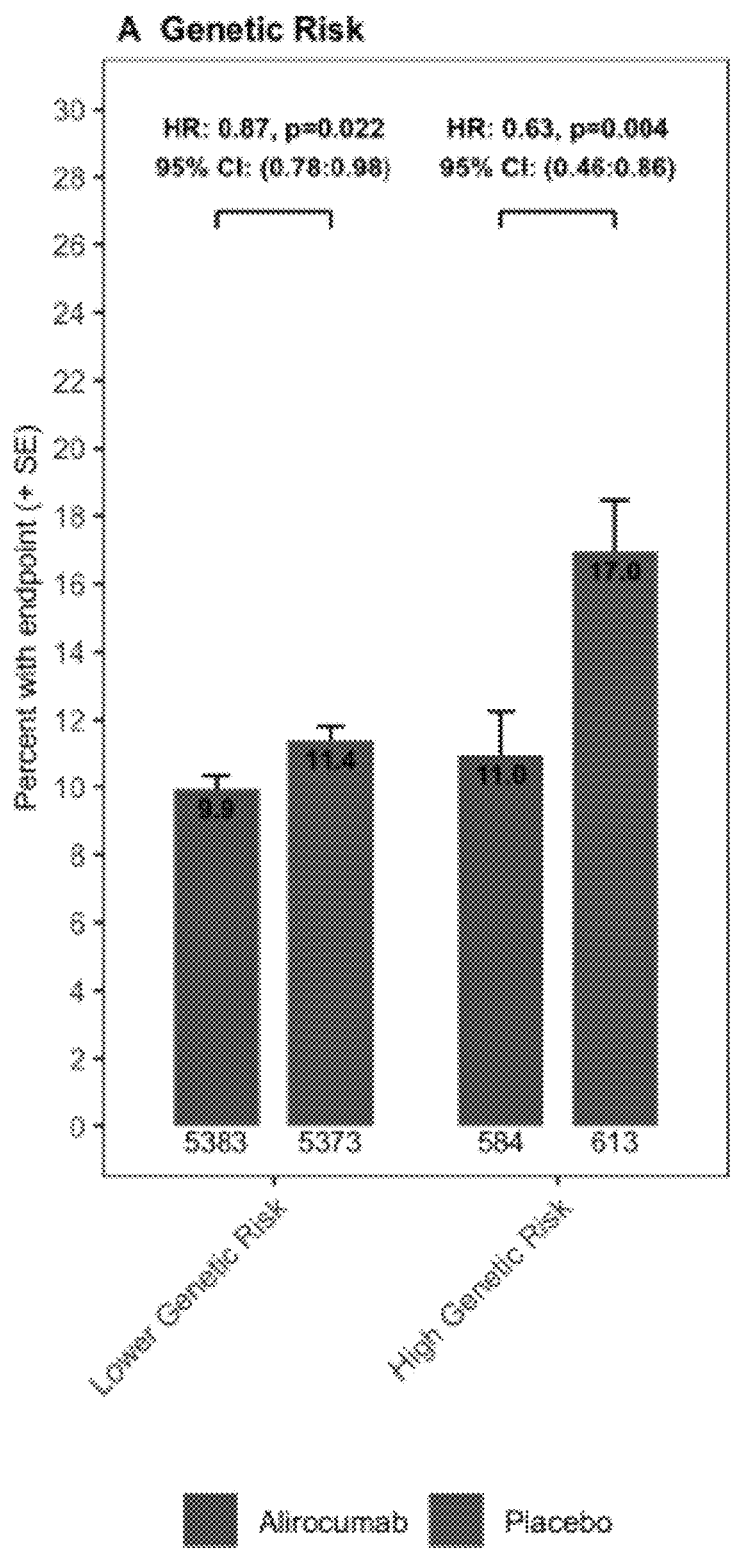
FIG. 27 shows incidence of MACE stratified by genetic risk and Lp(a) levels at baseline. Shown is the proportion with an event in patients of all ancestries, stratifying by genetic risk and/or LDL-C at baseline. Panel A stratifies by genetic risk (high genetic risk is PRS >90 percentile; lower genetic risk is PRS ≤90 percentile). Panel B stratifies by Lp(a) at baseline (Lp(a) ≥50 mg/dL and Lp(a) <50 mg/dL). Panel C stratifies both by genetic risk and Lp(a) at baseline. The numbers at the bottom of each panel are the number of patients in each group and the number inside each bar is the percent with MACE in each group. The hazard ratios and p-values were calculated from a Cox proportional hazards model, which was adjusted for ancestry, baseline LDL-C, Lp(a), age, sex, family history of premature coronary heart disease, and the following medical characteristics prior to index ACS: myocardial infarction; percutaneous coronary intervention; coronary artery bypass grafting; and congestive heart failure.
Figure 27:
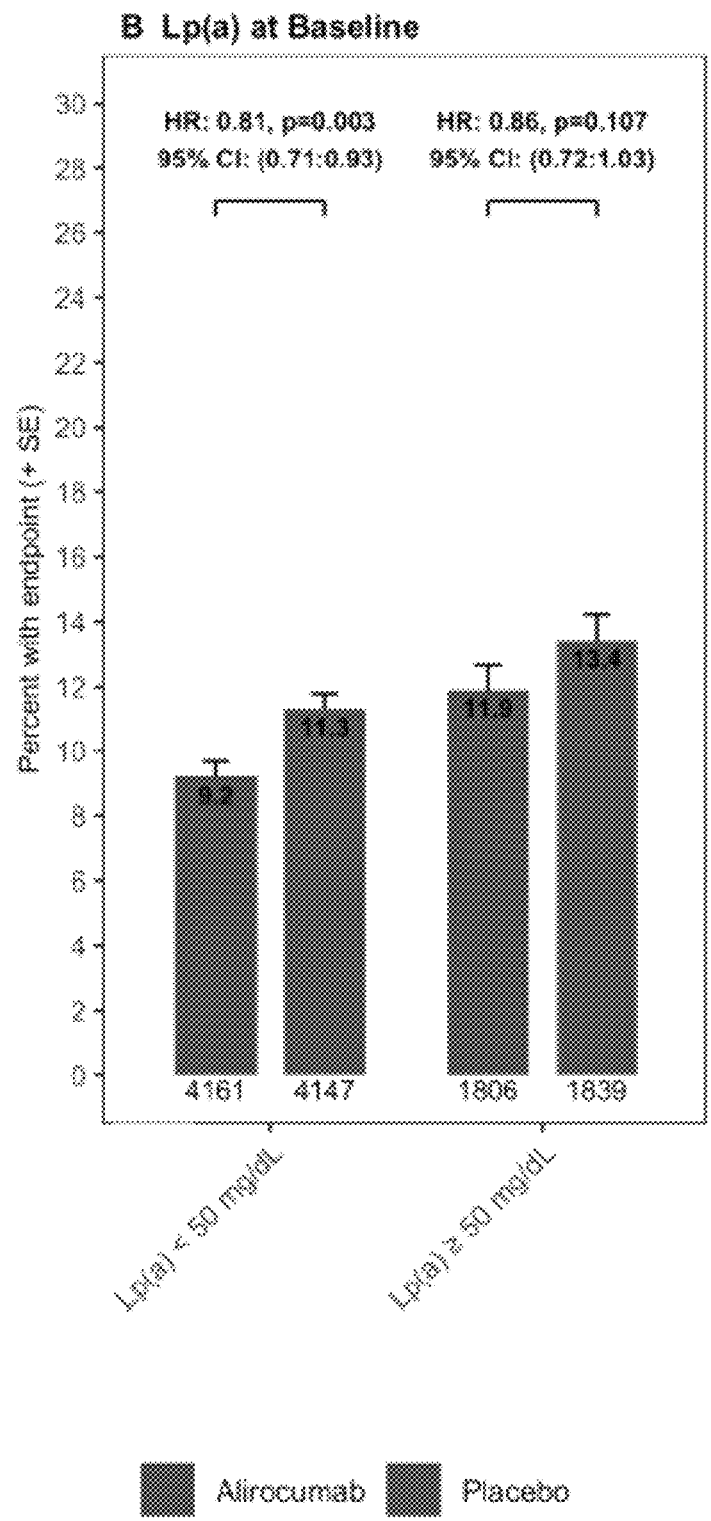
Figure 27:
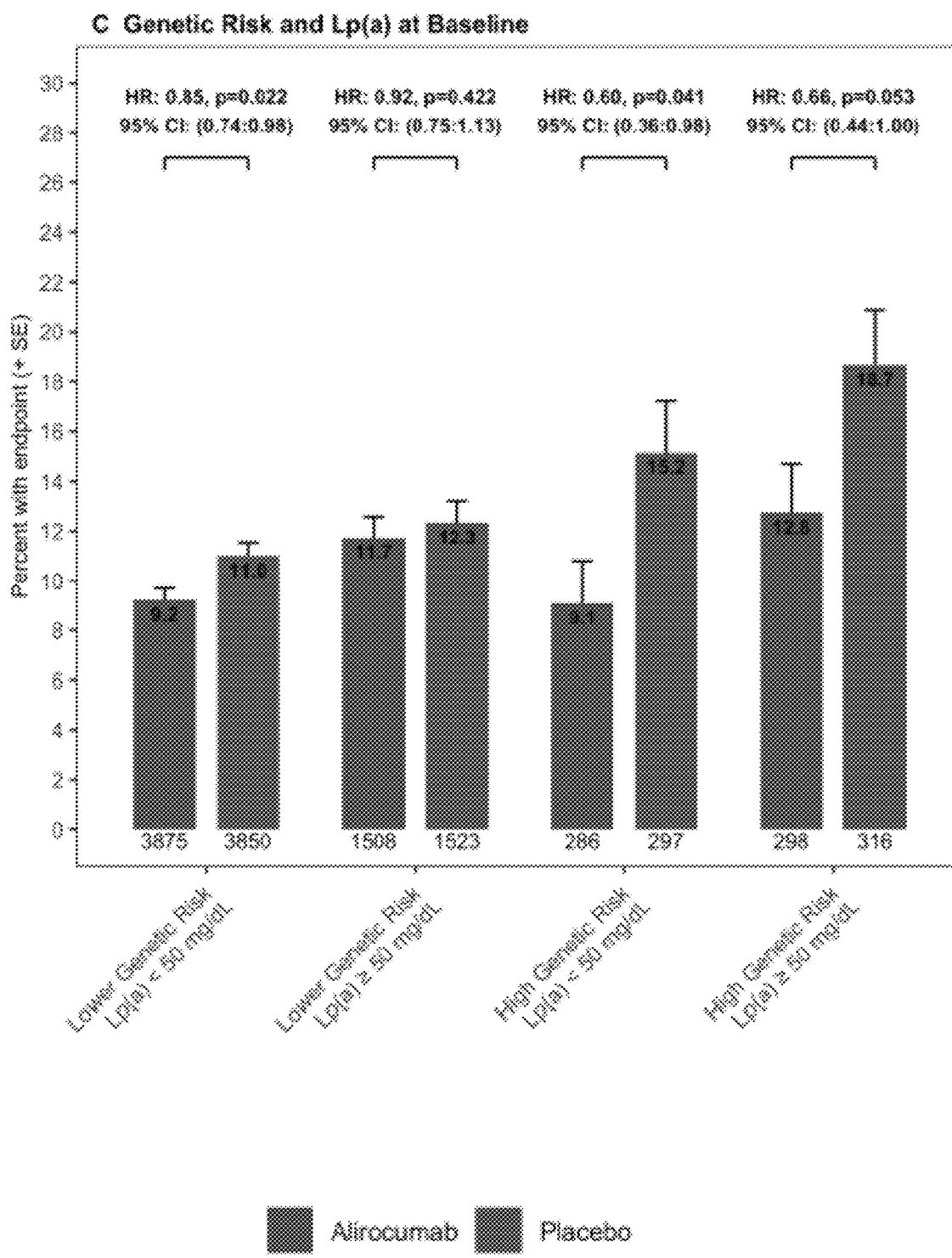

Due to the strong association between baseline Lp(a) levels and genetic risk (FIG. 1), the effects of genetic risk on changes in Lp(a) due to alirocumab treatment was also explored. Patients in the high genetic risk group had a median reduction in Lp(a) of 8.2 mg/dL (16.6% reduction from median baseline Lp(a)) at month 4 of the study), which compared to a median reduction of 5.1 mg/dL (25.6% reduction from median baseline Lp(a) in the lower genetic risk group) (FIG. 25). In stratified analyses (Lp(a) dichotomized at 50 mg/dL) patients with high Lp(a) and low Lp(a), both had greater reductions in events in the high genetic risk subgroup compared to the lower genetic risk subgroup (FIGS. 26-27). FIG. 28 shows MACE stratified by genetic risk and baseline Lp(a) taking into consideration VHR category. Panel A is stratified by genetic risk, where high genetic risk is PRS >90 percentile; lower genetic risk is PRS ≤90 percentile. Panel B is stratified by Lp(a) at baseline (Lp(a) ≥50 mg/dL and Lp(a) <50 mg/dL). Panel C is stratified by genetic risk and Lp(a) at baseline. These results suggest that the greater reduction in MACE observed in high genetic risk patients is not fully explained by baseline Lp(a) or change in Lp(a) due to alirocumab treatment.

Comparison of LDpred to 27- and 57-Variant PRS Models.

Figure 30:
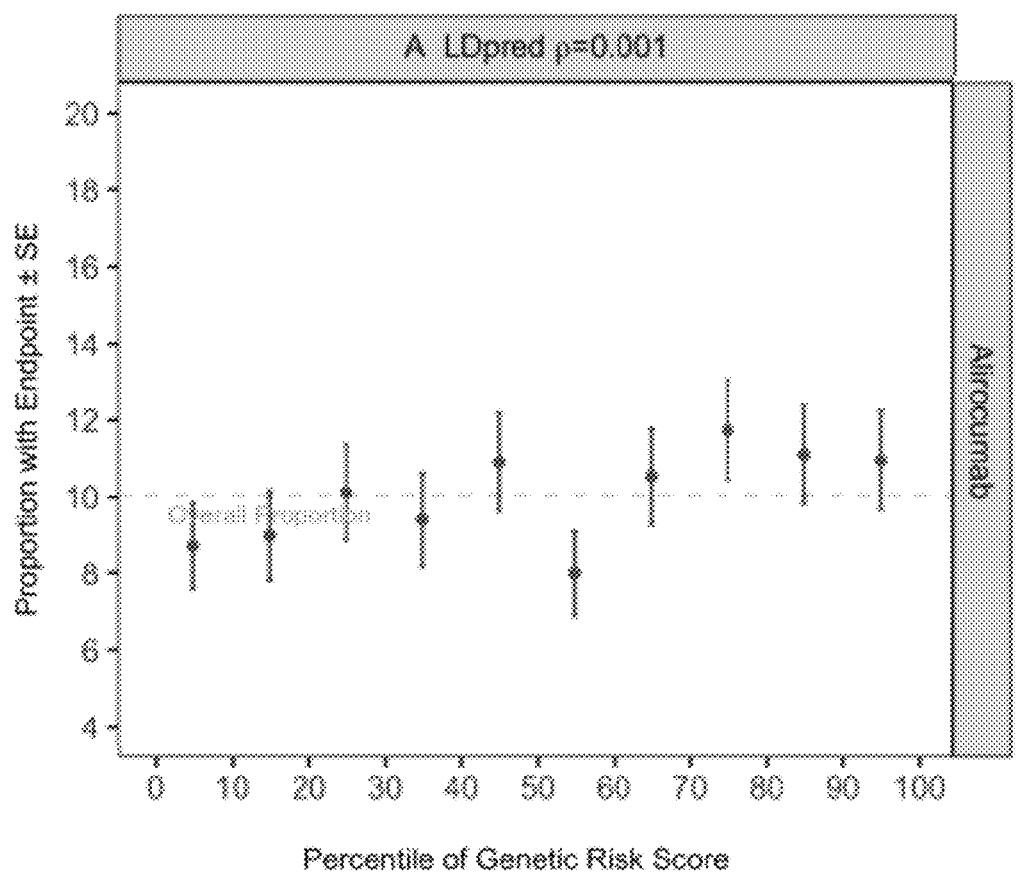
FIG. 30 shows treatment stratified decile plots for MACE for LDPred, 27-SNP, and 57-SNP models. This end point includes death from coronary heart disease, nonfatal myocardial infarction, fatal or nonfatal ischemic stroke, or unstable angina requiring hospitalization. Panel A shows results for LDPred (p=0.001), Panel B shows the results for the 27 SNP model, and Panel C displays the results for the 57 SNP model. The top row shows the percent with an event by genetic risk score decile in the alirocumab arm, while the bottom row shows risk by decile in the placebo arm.
Figure 30:
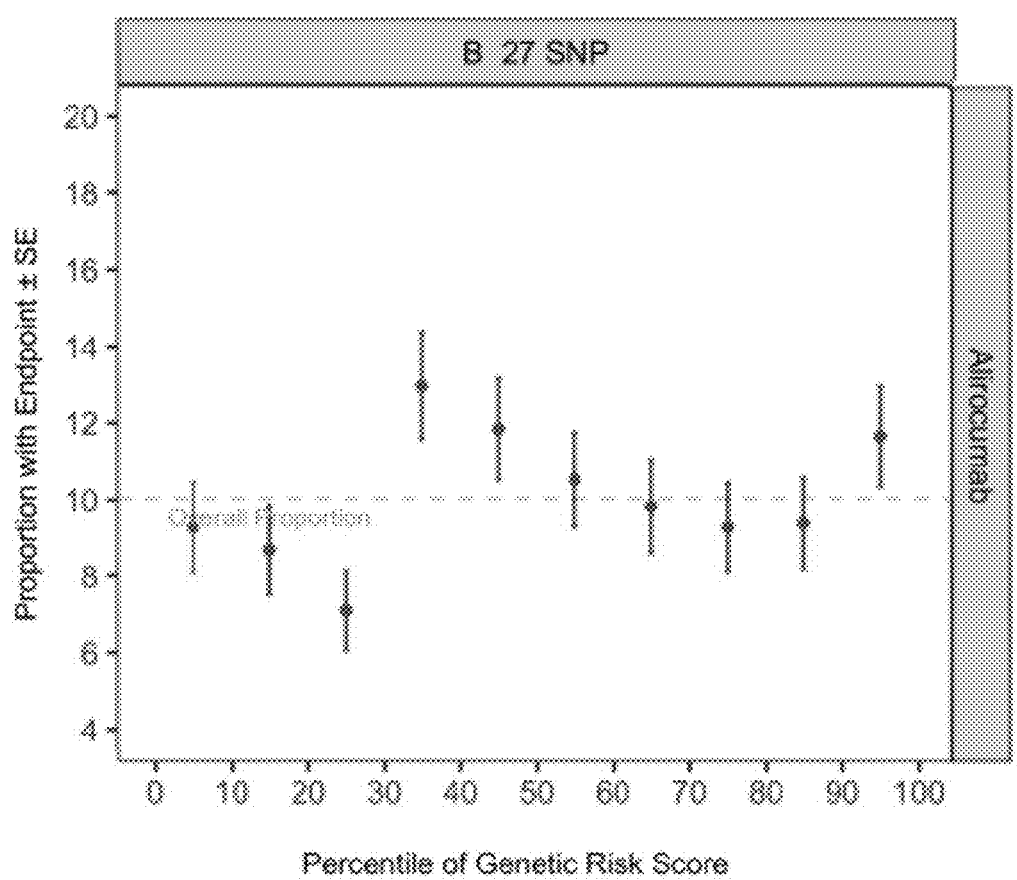
Figure 30:
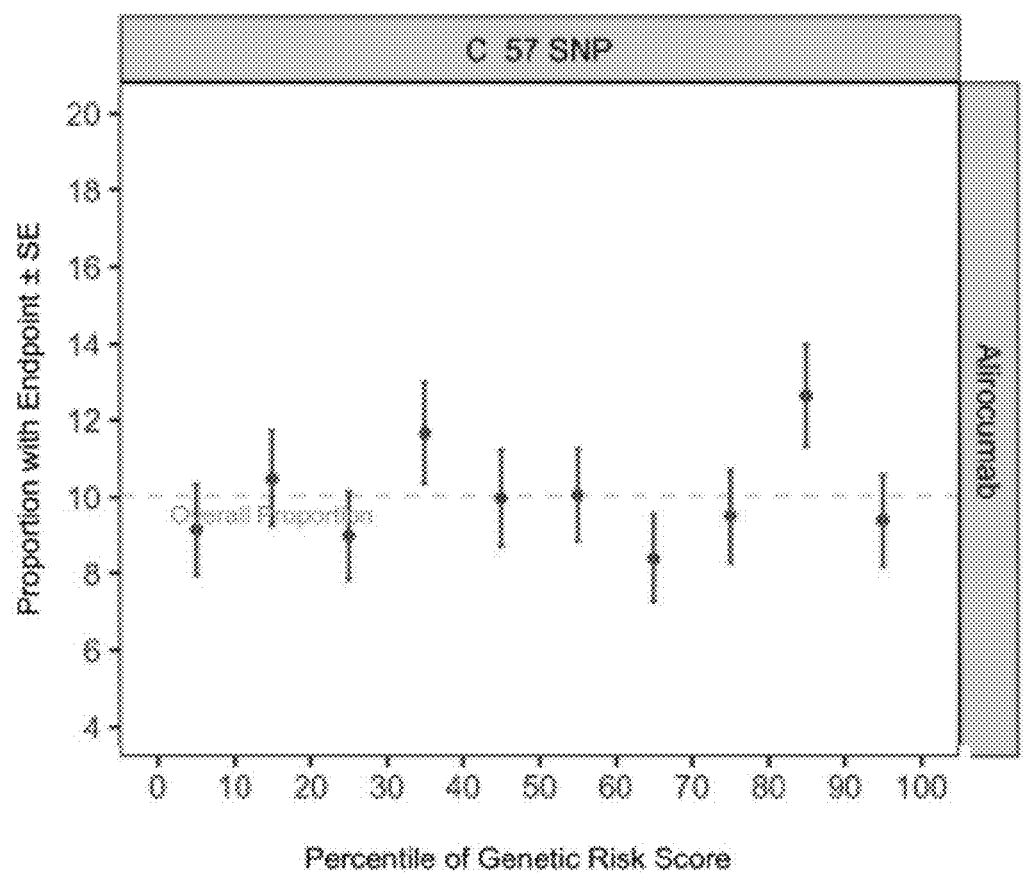
Figure 30:
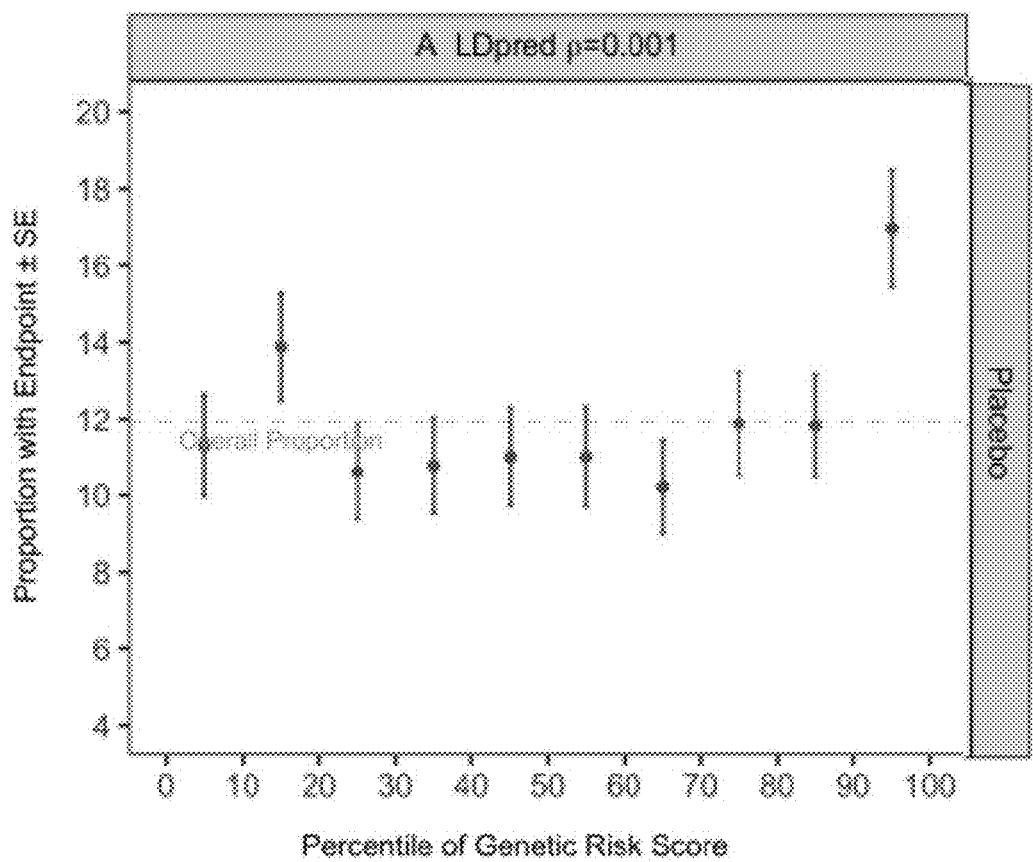
Figure 30:
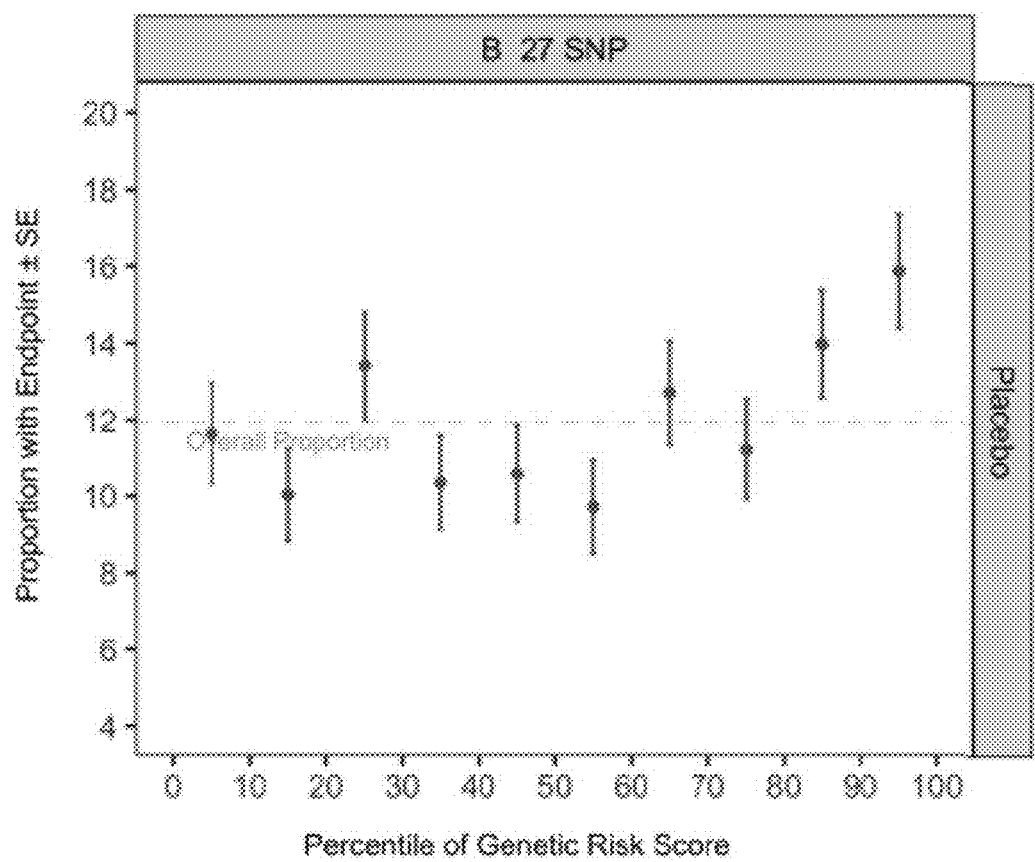
Figure 30:
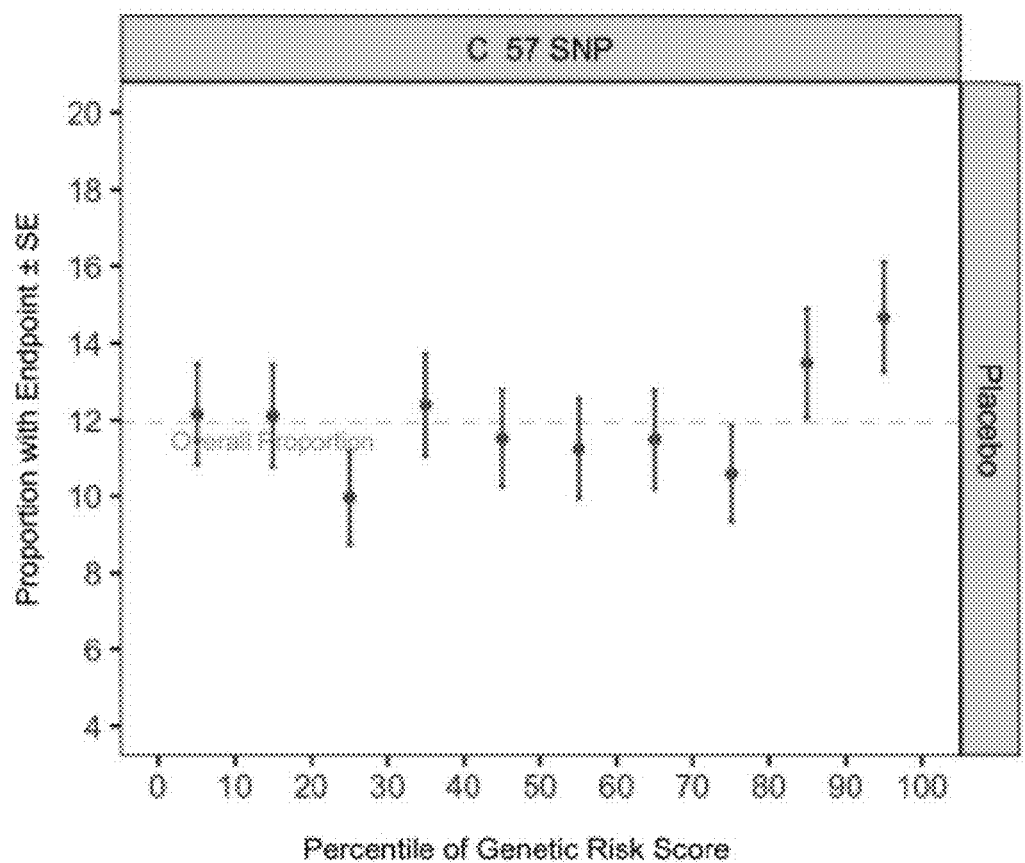

An assessment of alirocumab treatment benefit for the selected LDPred model (ρ=0.001) and the 27 and 57 candidate PRS models was also conducted. These analyses were performed using Cox proportional hazards models and adjusted for the covariates described above. Results by decile for each of the 3 models are shown in FIG. 30. In the 27 SNP model, the high genetic risk group and low genetic risk group HR and p-values were HR=0.68, p=0.008 and HR=0.85, p=0.016, respectively. In the 57 SNP model, the high genetic risk HR was 0.65, p=0.010 and the low genetic risk was HR=0.86, p=0.010. These results are similar to findings for LDPred (FIG. 4), with HRs of 0.63 (p=0.004) and 0.87 (p=0.022), and in contrast to the UK Biobank and DiscovEHR results shown in FIGS. 9 and 10. In UK Biobank, the MACE OR at the 90th percentile was 2.33, in contrast to the 27 SNP model, with an OR of 1.65. The differences between ODYSSEY findings and these larger EHR datasets may be due to either differences in study size, or difference in populations, in translating primary CAD risk to assessing treatment benefit of PCSK9 inhibition for recurrent events in high risk populations. The similarity in results for the high genetic risk group in ODYSSEY was not due to strong correlation across genetic risk scores. The $r^2$ between the LDpred and the 27- and 57-variant PRS was $r^2$=31.3% and $r^2$=31.4%, respectively; and between the 27- and 57-variant PRS, $r^2$=40.1%. Regardless, the consistency of the findings across models provides support for alirocumab treatment benefit in high genetic risk populations.

These findings support that genetic risk scores can greatly contribute to precision medicine, in particular by providing an independent and additive tool (that can be combined with more traditional risk measures) for enhancing risk assessment as well as predicting potential benefit from treatment. Such tools can better direct limited healthcare resources to target the patients at greatest risk, as well as those most likely to respond to therapies with limited access. In particular, this study shows that the PRS for CAD, which was previously developed to assess heart disease prevalence in large populations, is also very useful for predicting risk of recurrence in high genetic risk patients in the post-ACS setting. Furthermore, this study shows that the ability of the PRS is independent and additive with more traditional risk factors, such as LDL-C levels and FHS risk scores. Importantly, it also shows that the PRS can be combined with LDL-C levels and other risk measures to predict patients most likely to benefit from treatment (in this case, from the ability of the PCSK9-antibody alirocumab to prevent recurrent MACE).

In this pharmacogenomic analysis of nearly 12,000 post-ACS patients from the ODYSSEY OUTCOMES trial, patients with high PRS were at substantially higher risk of recurrent MACE, despite intensive statin therapy, and even after adjustment for demographic and clinical characteristics capturing known and established risk factors for atherosclerotic cardiovascular disease. While the overall incidence for MACE in the placebo arm was 11.1% when including all patients in the study, the subgroup of high genetic risk patients in the top decile of PRS had an incidence of 17.0%. The subgroup with high baseline LDL-C (≥100 mg/dL) had an incidence of 16.1%, and the subgroup of patients who had both high genetic risk and high baseline LDL-C had the highest incidence of 22.7%. These data suggest that both LDL-C and PRS are independent and important risk factors for identifying post-ACS patients at highest risk for MACE, despite intensive statin treatment. These analyses also demonstrated that the PRS was an independent risk factor compared to a composite score of established risk factors, the Framingham Heart Study risk score for recurrent coronary heart disease.

The PRS also identified a group of high genetic risk patients who had greater benefit from treatment. The high genetic risk patients had greater benefit from alirocumab treatment in terms of both absolute and relative reduction of MACE (as well as secondary endpoints) (6.0% absolute risk reduction in MACE compared to 1.5% for the lower genetic risk group, and 37% relative risk reduction in MACE compared to 13% for the lower genetic risk group). Furthermore, the present study shows that the PRS can be combined with traditional lipid biomarkers to not only identify individuals at highest risk for MACE, but where the greatest risk reduction may be achieved from treatment. Patients with high PRS and high LDL-C were not only at greatest risk of recurrent MACE (22.7%) despite intensive statin treatment, but had the greatest absolute and relative risk reduction from addition of alirocumab to statin treatment (9.2% absolute risk reduction, with 45% relative risk reduction); patients with high PRS and low LDL-C, or lower PRS and high LDL-C, had both intermediate risk and intermediate benefit. Patients with lower PRS and low LDL-C had lowest risk, and also had least benefit from alirocumab treatment. These findings have clear implications in terms of targeting access to such therapies for those at highest risk and most likely to benefit. This study also provides additional evidence from a different class of lipid lowering therapies, specifically from the PCSK9 inhibitor, alirocumab, when added to patients already receiving intensive statin treatment. These results suggest that the improved clinical outcomes for the high genetic risk patients is not being mediated by greater reductions in LDL-C after treatment, or by higher levels of LDL-C at baseline, for either statins or for alirocumab.

Lp(a) has been recognized as a major risk factor for coronary artery disease, Lp(a) levels are primarily determined genetically, and inhibition of PCSK9 is currently one of the few therapeutic approaches for lowering Lp(a). Overall in the ODYSSEY study, alirocumab treatment decreased Lp(a) levels by 23.4%. A strong association between high genetic risk and baseline Lp(a) levels was observed in this study at baseline (FIG. 1). Several lines of evidence demonstrate that the greater benefit with respect to MACE, observed in high genetic risk patients, is not due to either baseline Lp(a) levels or degree of Lp(a) lowering with alirocumab alone: 1) even though the PRS is significantly associated with elevated serum Lp(a) levels, the proportion of variance in serum Lp(a) levels explained by the PRS is only 3.1%; 2) the PRS and high genetic risk remained associated with a higher incidence of MACE and greater reduction in MACE with alirocumab even after adjustment for baseline Lp(a) and reduction in Lp(a); and 3) stratified analysis in patients with low and high Lp(a) baseline levels demonstrated that high genetic risk was associated with higher incidence and greater reduction in events, to a similar degree in Lp(a) subgroups and, thus, not fully explained by Lp(a) levels (FIGS. 26-27). Taken together, these results suggest that Lp(a) may be a strong contributor, but not the only driving mechanism for the PRS results in the present study.

The PRS in this study was developed using GWAS data from individuals of European ancestry. This analysis of the ODYSSEY OUTCOMES trial applied this PRS to patients from all ancestry groups combined (FIG. 1). Additional subgroup analysis was also performed in patients with European ancestry (FIG. 24) and the results were consistent with the larger analysis that included patients of all ancestries. While the sample sizes are small for some of the ancestry groups, it was also observed that the reduction in MACE after alirocumab treatment was directionally consistent in high genetic risk patients across all ancestry groups tested (FIG. 12). As GWAS data becomes available in more diverse populations, polygenic risk scores will likely improve over time for non-European populations as well.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of treating a patient who has received or is currently receiving an intensive statin therapy treatment, and who has a high genetic risk of recurrent major adverse cardiovascular event (MACE) despite intensive statin therapy, comprising administering a proprotein convertase subtilisin-kexin type 9 (PCSK9) inhibitor to the patient, wherein the patient:
   - does not have elevated levels of lipoprotein(a) (LPA or LP(a)) or LDL-C; and
   - has a coronary artery disease polygenic risk score (CAD-PRS) greater than the $90^{th}$ percentile determined from a reference population, wherein the CAD-PRS comprises a weighted sum of a plurality of genetic variants associated with coronary artery disease;

wherein the patient receiving the PCSK9 inhibitor demonstrates reduced absolute and relative risk of developing recurring MACE compared to a patient with the same CAD-PRS receiving placebo treatment.

2. The method according to claim 1, wherein the CAD-PRS threshold score is the top 95% within a reference population.

3. The method according to claim 1, wherein the reference population comprises at least 100 patients.

4. The method according to claim 1, wherein the plurality of genetic variants is determined by calculating genetic variant performance in the reference population and selecting the highest performing genetic variants.

5. The method according to claim 4, wherein genetic variant performance is calculated with respect to coronary artery disease risk based on statistical significance, strength of association, and/or a probability distribution.

6. The method according to claim 5, wherein the CAD-PRS is calculated using LDPred method.

7. The method according to claim 5, wherein the CAD-PRS is calculated using pruning and thresholding method.

* * * * *

SEQUENCE LISTING

<160> NUMBER OF SEQ ID NOS: 2

<210> SEQ ID NO 1
<211> LENGTH: 3731

```
<212> TYPE: DNA
<213> ORGANISM: homo sapien

<400> SEQUENCE: 1
gtccgatggg gctctggtgg cgtgatctgc gcgccccagg cgtcaagcac ccacaccta      60 gaaggtttcc gcagcgacgt cgaggcgctc atggttgcag gcgggcgccg ccgttcagtt    120
cagggtctga gcctggagga gtgagccagg cagtgagact ggctcgggcg ggccgggacg    180
cgtcgttgca gcagcggctc ccagctccca gccaggattc cgcgcgcccc ttcacgcgcc    240
ctgctcctga acttcagctc ctgcacagtc ctcccaccg caaggctcaa ggcgccgccg    300
gcgtggaccg cgcacggcct ctaggtctcc tcgccaggac agcaacctct cccctggccc    360
tcatgggcac cgtcagctcc aggcggtcct ggtggccgct gccactgctg ctgctgctgc    420
tgctgctcct gggtcccgcg gcgcccgtg cgcaggagga cgaggacggc gactacgagg     480
agctggtgct agccttgcgt tccgaggagg acggcctggc cgaagcaccc gagcacggaa    540
ccacagccac cttccaccgc tgcgccaagg atccgtggag gttgcctggc acctacgtgg    600
tggtgctgaa ggaggagacc cacctctcgc agtcagagcg cactgcccgc cgcctgcagg    660
cccaggctgc ccgccgggga tacctcacca agatcctgca tgtcttccat ggccttcttc    720
ctggcttcct ggtgaagatg agtggcgacc tgctggagct ggcctttgaag ttgccccatg   780 tcgactacat cgaggaggac tcctctgtct ttgcccagag catcccgtgg aacctggagc    840
ggattacccc tccacggtac cgggcggatg aataccagcc ccccgacgga ggcagcctgg    900
tggaggtgta tctcctagac accagcatac agagtgacca ccgggaaatc gagggcaggg    960
tcatggtcac cgacttcgag aatgtgcccg aggaggacgg gacccgcttc cacagacagg   1020
ccagcaagtg tgacagtcat ggcacccacc tggcaggggt ggtcagcggc cgggatgccg   1080
gcgtggccaa gggtgccagc atgcgcagcc tgcgcgtgct caactgccaa gggaagggca   1140
cggttagcgg caccctcata ggcctggagt ttattcggaa aagccagctg gtccagcctg   1200
tggggccact ggtggtgctg ctgccctgg cgggtgggta cagccgcgtc ctcaacgccg    1260
cctgccagcg cctggcgagg gctggggtcg tgctggtcac cgctgccggc aacttccggg   1320
acgatgcctg cctctactcc ccagcctcag ctcccgaggt catcacagtt ggggccacca   1380
atgcccaaga ccagccggtg accctgggga cttttgggac caactttggc cgctgtgtgg   1440
acctctttgc ccaggggag acatcattg gtgcctccag cgactgcagc acctgctttg    1500
tgtcacagag tgggacatca caggctgctg cccacgtggc tggcattgca gccatgatgc   1560
tgtctgccga gccggagctc acccctggccg agttgaggca gagactgatc cacttctctg   1620
ccaaagatgt catcaatgag gcctggttcc ctgaggacca gcgggtactg acccccaacc   1680
tggtggccgc cctgcccccc agcacccatg gggcaggttg gcagctgttt tgcaggactg   1740
tatggtcagc acactcgggg cctacacgga tggccacagc cgtcgcccgc tgcgccccag   1800
atgaggagct gctgagctgc tccagttttct ccaggagtgg gaagcggcgg ggcgagcgca   1860
tggaggccca aggggggcaag ctggtctgcc gggcccacaa cgcttttggg ggtgagggtg   1920
tctacgccat tgccaggtgc tgcctgctac cccaggccaa ctgcagcgtc cacacagctc   1980
caccagctga ggcagcatg gggacccgtg tccactgcca caacagggc cacgtcctca    2040 caggctgcag ctcccactgg gaggtggagg accttggcac ccacaagccg cctgtgctga   2100
ggccacgagg tcagcccaac cagtgcgtgg ccacagggg ggccagcatc cacgcttcct   2160
gctgccatgc cccaggtctg gaatgcaaag tcaaggagca tggaatcccg gccccctcagg   2220
```

```
agcaggtgac cgtggcctgc gaggagggct ggaccctgac tggctgcagt gccctccctg    2280
ggacctccca cgtcctgggg gcctacgccg tagacaacac gtgtgtagtc aggagccggg    2340
acgtcagcac tacaggcagc accagcgaag gggccgtgac agccgttgcc atctgctgcc    2400
ggagccggca cctggcgcag gcctcccagg agctccagtg acagccccat cccaggatgg    2460
gtgtctgggg agggtcaagg gctggggctg agctttaaaa tggttccgac ttgtccctct    2520
ctcagccctc catggcctgg cacgagggga tggggatgct tccgcctttc cggggctgct    2580
ggcctggccc ttgagtgggg cagcctcctt gcctggaact cactcactct gggtgcctcc    2640
tccccaggtg gaggtgccag gaagctccct ccctcactgt ggggcatttc accattcaaa    2700
caggtcgagc tgtgctcggg tgctgccagc tgctcccaat gtgccgatgt ccgtgggcag    2760
aatgactttt attgagctct tgttccgtgc caggcattca atcctcaggt ctccaccaag    2820
gaggcaggat tcttcccatg gatagggag ggggcggtag gggctgcagg acaaacatc     2880 gttgggggt gagtgtgaaa ggtgctgatg gccctcatct ccagctaact gtggagaagc    2940
ccctgggggc tccctgatta atggaggctt agctttctgg atggcatcta gccagaggct    3000
ggagacaggt gcgcccctgg tggtcacagg ctgtgccttg gtttcctgag ccacctttac    3060
tctgctctat gccaggctgt gctagcaaca cccaaaggtg gcctgcgggg agccatcacc    3120
taggactgac tcggcagtgt gcagtggtgc atgcactgtc tcagccaacc cgctccacta    3180
cccggcaggg tacacattcg caccctact tcacagagga agaaacctgg aaccagaggg    3240
ggcgtgcctg ccaagctcac acagcaggaa ctgagccaga aacgcagatt gggctggctc    3300
tgaagccaag cctcttctta cttcacccgg ctgggtcct cattttacg ggtaacagtg      3360 aggctgggaa ggggaacaca gaccaggaag ctcggtgagt gatggcagaa cgatgcctgc    3420
aggcatggaa cttttttccgt tatcacccag gcctgattca ctggcctggc ggagatgctt    3480
ctaaggcatg gtcgggggag agggccaaca actgtccctc cttgagcacc agccccaccc    3540
aagcaagcag acatttatct tttgggtctg tcctctctgt tgccttttta cagccaactt    3600
ttctagacct gttttgcttt tgtaacttga agatatttat tctgggtttt gtagcatttt    3660
tattaatatg gtgactttt aaaataaaaa caaacaaacg ttgtcctaac aaaaaaaaaa    3720
aaaaaaaaaa a                                                        3731
```

<210> SEQ ID NO 2
<211> LENGTH: 635
<212> TYPE: PRT
<213> ORGANISM: homo sapien

<400> SEQUENCE: 2

```
Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
```

```
                100             105             110
His Val Phe His Gly Leu Leu Pro Gly Phe Leu Val Lys Met Ser Gly
            115             120             125
Asp Leu Leu Glu Leu Ala Leu Lys Leu Pro His Val Asp Tyr Ile Glu
130             135             140
Glu Asp Ser Ser Val Phe Ala Gln Ser Ile Pro Trp Asn Leu Glu Arg
145             150             155             160
Ile Thr Pro Pro Arg Tyr Arg Ala Asp Glu Tyr Gln Pro Pro Asp Gly
            165             170             175
Gly Ser Leu Val Glu Val Tyr Leu Leu Asp Thr Ser Ile Gln Ser Asp
            180             185             190
His Arg Glu Ile Glu Gly Arg Val Met Val Thr Asp Phe Glu Asn Val
            195             200             205
Pro Glu Glu Asp Gly Thr Arg Phe His Arg Gln Ala Ser Lys Cys Asp
            210             215             220
Ser His Gly Thr His Leu Ala Gly Val Val Ser Gly Arg Asp Ala Gly
225             230             235             240
Val Ala Lys Gly Ala Ser Met Arg Ser Leu Arg Val Leu Asn Cys Gln
            245             250             255
Gly Lys Gly Thr Val Ser Gly Thr Leu Ile Gly Leu Glu Phe Ile Arg
            260             265             270
Lys Ser Gln Leu Val Gln Pro Val Gly Pro Leu Val Val Leu Leu Pro
            275             280             285
Leu Ala Gly Gly Tyr Ser Arg Val Leu Asn Ala Ala Cys Gln Arg Leu
            290             295             300
Ala Arg Ala Gly Val Val Leu Val Thr Ala Ala Gly Asn Phe Arg Asp
305             310             315             320
Asp Ala Cys Leu Tyr Ser Pro Ala Ser Ala Pro Glu Val Ile Thr Val
            325             330             335
Gly Ala Thr Asn Ala Gln Asp Gln Pro Val Thr Leu Gly Thr Leu Gly
            340             345             350
Thr Asn Phe Gly Arg Cys Val Asp Leu Phe Ala Pro Gly Glu Asp Ile
            355             360             365
Ile Gly Ala Ser Ser Asp Cys Ser Thr Cys Phe Val Ser Gln Ser Gly
            370             375             380
Thr Ser Gln Ala Ala Ala His Val Ala Gly Ile Ala Ala Met Met Leu
385             390             395             400
Ser Ala Glu Pro Glu Leu Thr Leu Ala Glu Leu Arg Gln Arg Leu Ile
            405             410             415
His Phe Ser Ala Lys Asp Val Ile Asn Glu Ala Trp Phe Pro Glu Asp
            420             425             430
Gln Arg Val Leu Thr Pro Asn Leu Val Ala Ala Leu Pro Pro Ser Thr
            435             440             445
His Gly Ala Gly Trp Gln Leu Phe Cys Arg Thr Val Trp Ser Ala His
            450             455             460
Ser Gly Pro Thr Arg Met Ala Thr Ala Val Ala Arg Cys Ala Pro Asp
465             470             475             480
Glu Glu Leu Leu Ser Cys Ser Ser Phe Ser Arg Ser Gly Lys Arg Arg
            485             490             495
Gly Glu Arg Met Glu Ala Gln Gly Gly Lys Leu Val Cys Arg Ala His
            500             505             510
Asn Ala Phe Gly Gly Glu Gly Val Tyr Ala Ile Ala Arg Cys Cys Leu
            515             520             525
```

```
-continued

Leu Pro Gln Ala Asn Cys Ser Val His Thr Ala Pro Pro Ala Glu Ala
    530             535             540

Ser Met Gly Thr Arg Val His Cys His Gln Gln Gly His Val Leu Thr
545                 550             555                     560

Gly Cys Ser Ser His Trp Glu Val Glu Asp Leu Gly Thr His Lys Pro
            565                 570                 575

Pro Val Leu Arg Pro Arg Gly Gln Pro Asn Gln Cys Val Gly His Arg
            580             585                 590

Glu Ala Ser Ile His Ala Ser Cys Cys His Ala Pro Gly Leu Glu Cys
        595             600             605

Lys Val Lys Glu His Gly Ile Pro Ala Pro Gln Glu Gln Val Thr Val
    610             615             620

Ala Cys Glu Glu Gly Trp Thr Leu Thr Gly Cys
625             630             635
```